United States Patent
Donohoue et al.

(10) Patent No.: US 10,590,415 B2
(45) Date of Patent: Mar. 17, 2020

(54) ENGINEERED NUCLEIC ACID-TARGETING NUCLEIC ACIDS

(71) Applicant: Caribou Biosciences, Inc., Berkeley, CA (US)

(72) Inventors: Paul Daniel Donohoue, Berkeley, CA (US); Andrew Paul May, San Francisco, CA (US)

(73) Assignee: Ceribou Biosciences, Inc., Berkeley, CA (US)

( * ) Notice: Subject to any disclaimer, the term of this patent is extended or adjusted under 35 U.S.C. 154(b) by 0 days.

(21) Appl. No.: 15/787,630

(22) Filed: Oct. 18, 2017

(65) Prior Publication Data
US 2018/0155720 A1  Jun. 7, 2018

Related U.S. Application Data

(63) Continuation of application No. 15/371,188, filed on Dec. 6, 2016, now Pat. No. 9,816,093.

(51) Int. Cl.
  *C12N 15/11* (2006.01)
  *C12N 15/09* (2006.01)
  *C12N 15/113* (2010.01)
  *C12N 9/22* (2006.01)
  *C12N 15/10* (2006.01)

(52) U.S. Cl.
  CPC .............. *C12N 15/113* (2013.01); *C12N 9/22* (2013.01); *C12N 15/102* (2013.01); *C12N 15/111* (2013.01); *C07K 2319/00* (2013.01); *C12N 2310/20* (2017.05); *C12N 2320/11* (2013.01); *C12N 2320/33* (2013.01)

(58) Field of Classification Search
None
See application file for complete search history.

(56) References Cited

U.S. PATENT DOCUMENTS

| 8,697,359 B1 | 4/2014 | Zhang |
| 8,771,945 B1 | 7/2014 | Zhang |

(Continued)

FOREIGN PATENT DOCUMENTS

| WO | WO 2015/071474 | 5/2015 |
| WO | WO 2016/123230 | 8/2016 |
| WO | WO 2016/161380 | 10/2016 |

OTHER PUBLICATIONS

Jinek, M., et al., "A programmable dual-RNA-guided DNA endonuclease in adaptive bacterial immunity," Science 337 (6096):816-21 (2012).

(Continued)

*Primary Examiner* — Rebecca E Prouty
(74) *Attorney, Agent, or Firm* — Barbara G. McClung; Katharina F. S. Stengel

(57) ABSTRACT

The present disclosure provides engineered Class 2 CRISPR-Cas-associated discontinuous first-stem nucleic-acid targeting nucleic acids, nucleoprotein complexes comprising these nucleic acids, and compositions thereof. Nucleic acid sequences encoding the Class 2 CRISPR-Cas-associated discontinuous first-stem nucleic-acid targeting nucleic acids, as well as expression cassettes, vectors and cells comprising such nucleic acid sequences, are described. Also, methods are disclosed for making and using the Class 2 CRISPR-Cas-associated discontinuous first-stem nucleic-acid targeting nucleic acids, nucleoprotein complexes comprising such nucleic acids, and compositions thereof.

20 Claims, 19 Drawing Sheets

Specification includes a Sequence Listing.

(56) References Cited

U.S. PATENT DOCUMENTS

| | | |
|---|---|---|
| 8,795,965 B2 | 8/2014 | Zhang |
| 8,841,260 B2 | 9/2014 | Miller et al. |
| 8,865,406 B2 | 10/2014 | Zhang et al. |
| 8,871,445 B2 | 10/2014 | Cong et al. |
| 8,889,356 B2 | 11/2014 | Zhang et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2011/0223638 A1 | 9/2011 | Wiedenheft et al. |
| 2013/0130248 A1 | 5/2013 | Haurwitz et al. |
| 2014/0068797 A1 | 3/2014 | Doudna et al. |
| 2014/0294773 A1 | 10/2014 | Brouns et al. |
| 2014/0302563 A1 | 10/2014 | Doudna et al. |
| 2014/0315985 A1 | 10/2014 | May et al. |
| 2015/0024499 A1 | 1/2015 | Brouns et al. |
| 2015/0045546 A1 | 2/2015 | Siksnys et al. |
| 2015/0050699 A1 | 2/2015 | Siksnys et al. |
| 2015/0059010 A1 | 2/2015 | Cigan et al. |
| 2015/0082478 A1 | 3/2015 | Cigan et al. |
| 2015/0152398 A1 | 6/2015 | Doudna et al. |
| 2016/0362667 A1 | 12/2016 | Caribou |

OTHER PUBLICATIONS

Jinek, M., et al., "A programmable dual-RNA-guided DNA endonuclease in adaptive bacterial immunity," Science 337 (6096):816-21 (2012); Supplemental Materials.
Briner, A., et al., "Guide RNA Functional Modules Direct Cas9 Activity and Orthogonality," Molecular Cell 56(2)333-339 (2014).
Wright, A. V., et al., "Rational design of a split-Cas9 enzyme complex," PNAS 112(10):2984-2989 (2015).
Nishimasu, H., et al., "Crystal Structure of Cas9 in Complex with Guide RNA and Target DNA," Cell 156(5):935-49 (2014).
U.S. Appl. No. 14/997,474, filed Jan. 15, 2016.
U.S. Appl. No. 14/416,338, filed Jan. 22, 2015, U.S. Pat. No. 9,260,752, Feb. 16, 2016.
U.S. Appl. No. 14/751,055, filed Jun. 25, 2015, U.S. Pat. No. 9,410,198, Aug. 9, 2016.
U.S. Appl. No. 14/751,058, filed Jun. 25, 2015.
U.S. Appl. No. 14/751,070, filed Jun. 25, 2015.
U.S. Appl. No. 15/344,487, filed Nov. 4, 2016.
U.S. Appl. No. 14/977, 514, filed Dec. 21, 2015.
U.S. Appl. No. 15/159,619, filed May 19, 2016, U.S. Pat. No. 9,725,714, Aug. 8, 2017.
U.S. Appl. No. 15/159,776, filed May 19, 2016.
U.S. Appl. No. 15/202,518, filed Jul. 5, 2016.
U.S. Appl. No. 15/660,906, filed Jul. 26, 2017.
U.S. Appl. No. 14/250,224, filed Apr. 10, 2014.
U.S. Appl. No. 15/390,584, filed Dec. 26, 2016.
U.S. Appl. No. 14/836,753, filed Aug. 26, 2015.
U.S. Appl. No. 14/835,675, filed Aug. 25, 2015, U.S. Pat. No. 9,580,727, Feb. 28, 2017.
U.S. Appl. No. 15/339,633, filed Oct. 31, 2016, U.S. Pat. No. 9,745,600, Aug. 29, 2017.
U.S. Appl. No. 15/665,155, filed Jul. 31, 2017.
U.S. Appl. No. 15/665,201, filed Jul. 31, 2017.
U.S. Appl. No. 15/253,725, filed Aug. 31, 2016.
U.S. Appl. No. 15/331,676, filed Oct. 21, 2016, U.S. Pat. No. 9,677,090, Jun. 13, 2017.
U.S. Appl. No. 15/460,642, filed Mar. 16, 2017, U.S. Pat. No. 9,745,562, Aug. 29, 2017.
U.S. Appl. No. 15/675,677, filed Aug. 11, 2017.
U.S. Appl. No. 15/368,570, filed Dec. 2, 2016, U.S. Pat. No. 9,771,600, Sep. 26, 2017.
U.S. Appl. No. 15/703,992, filed Sep. 14, 2017.
U.S. Appl. No. 15/371,188, filed Dec. 6, 2016.
International Search Report from PCT International Application No. PCT/US2017/064771, which corresponds to the present application, dated Feb. 28, 2018.

ENGINEERED NUCLEIC ACID-TARGETING NUCLEIC ACIDS

CROSS-REFERENCE TO RELATED APPLICATIONS

This application is a continuation of U.S. patent application Ser. No. 15/371,188, filed 6 Dec. 2016, now allowed, which application is herein incorporated by reference in its entirety.

STATEMENT REGARDING FEDERALLY SPONSORED RESEARCH OR DEVELOPMENT

Not applicable.

SEQUENCE LISTING

The present application contains a Sequence Listing that has been submitted electronically in ASCII format and is hereby incorporated by reference in its entirety. The ASCII copy, created on 9 Jan. 2018, is named CBI024-11 ST25.txt and is 18 KB in size.

TECHNICAL FIELD

The present disclosure relates generally to engineered nucleic-acid targeting nucleic acids and nucleoprotein complexes comprising such engineered nucleic-acid targeting nucleic acids and one or more Cas proteins. The disclosure also relates to compositions and methods for making and using the engineered nucleic-acid targeting nucleic acids and nucleoprotein complexes of the present invention.

BACKGROUND

Clustered regularly interspaced short palindromic repeats (CRISPR) and CRISPR-associated proteins (Cas) constitute the CRISPR-Cas system. The CRISPR-Cas system provides adaptive immunity against foreign DNA in bacteria (see, e.g., Barrangou, R., et al., Science 315:1709-1712 (2007); Makarova, K. S., et al., Nature Reviews Microbiology 9:467-477 (2011); Garneau, J. E., et al., Nature 468:67-71 (2010); Sapranauskas, R., et al., Nucleic Acids Research 39:9275-9282 (2011)).

CRISPR-Cas systems have recently been reclassified into two classes, comprising five types and sixteen subtypes (see Makarova, K., et al., Nature Reviews Microbiology 13:1-15 (2015)). This classification is based upon identifying all Cas genes in a CRISPR-Cas locus and determining the signature genes in each CRISPR-Cas locus, ultimately placing the CRISPR-Cas systems in either Class 1 or Class 2 based upon the genes encoding the effector module, i.e., the proteins involved in the interference stage. Recently a sixth CRISPR-Cas system (Type VI) has been identified (see Abudayyeh O., et al., Science 353(6299):aaf5573 (2016)). Certain bacteria possess more than one type of CRISPR-Cas system.

Class 1 systems have a multi-subunit crRNA-effector complex, whereas Class 2 systems have a single protein, such as Cas9, Cpf1, C2c1, C2c2, C2c3, or a crRNA-effector complex. Class 1 systems comprise Type I, Type III, and Type IV systems. Class 2 systems comprise Type II, Type V, and Type VI systems.

Type II systems have cas1, cas2, and cas9 genes. The cas9 gene encodes a multi-domain protein that combines the functions of the crRNA-effector complex with DNA target sequence cleavage. Type II systems are further divided into three subtypes, subtypes II-A, II-B, and II-C. Subtype II-A contains an additional gene, csn2. Examples of organisms with a subtype II-A systems include, but are not limited to, *Streptococcus pyogenes*, *Streptococcus thermophilus*, and *Staphylococcus aureus*. Subtype II-B lacks the csn2 protein, but has the cas4 protein. An example of an organism with a subtype II-B system is *Legionella pneumophila*. Subtype II-C is the most common Type II system found in bacteria and has only three proteins, Cas1, Cas2, and Cas9. An example of an organism with a subtype II-C system is *Neisseria lactamica*.

Type V systems have a cpf1 gene and cas1 and cas2 genes (see Zetsche, B., et al., Cell 163:1-13 (2015)). The cpf1 gene encodes a protein, Cpf1, that has a RuvC-like nuclease domain that is homologous to the respective domain of Cas9, but lacks the HNH nuclease domain that is present in Cas9 proteins. Type V systems have been identified in several bacteria including, but not limited to, *Parcubacteria bacterium, Lachnospiraceae bacterium, Butyrivibrio proteoclasticus, Peregrinibacteria bacterium, Acidaminococcus* spp., *Porphyromonas macacae, Porphyromonas crevioricanis, Prevotella disiens, Moraxella bovoculi, Smithella* spp., *Leptospira inadai, Franciscella tularensis, Franciscella novicida, Candidatus methanoplasma termitum,* and *Eubacterium eligens*. Recently it has been demonstrated that Cpf1 also has RNase activity and is responsible for pre-crRNA processing (see Fonfara, I., et al., Nature 532(7600):517-521 (2016)).

In Class 2 systems, the crRNA is associated with a single protein and achieves interference by combining nuclease activity with RNA-binding domains and base-pair formation between the crRNA and a nucleic acid target sequence.

In Type II systems, nucleic acid target sequence binding involves Cas9 and the crRNA, as does the nucleic acid target sequence cleavage. In Type II systems, the RuvC-like nuclease (RNase H fold) domain and the HNH (McrA-like) nuclease domain of Cas9 each cleave one of the strands of the double-stranded nucleic acid target sequence. The Cas9 cleavage activity of Type II systems also requires hybridization of crRNA to a tracrRNA to form a duplex that facilitates the crRNA and nucleic acid target sequence binding by the Cas9 protein.

In Type V systems, nucleic acid target sequence binding involves Cpf1 and the crRNA, as does the nucleic acid target sequence cleavage. In Type V systems, the RuvC-like nuclease domain of Cpf1 cleaves one strand of the double-stranded nucleic acid target sequence, and a putative nuclease domain cleaves the other strand of the double-stranded nucleic acid target sequence in a staggered configuration, producing 5' overhangs, which is in contrast to the blunt ends generated by Cas9 cleavage. These 5' overhangs may facilitate insertion of DNA.

The Cpf1 cleavage activity of Type V systems does not require hybridization of crRNA to tracrRNA to form a duplex, rather the crRNA of Type V systems uses a single crRNA that has a stem-loop structure forming an internal duplex. Cpf1 binds the crRNA in a sequence and structure specific manner that recognizes the stem loop and sequences adjacent to the stem loop, most notably the nucleotides 5' of the spacer sequences that hybridizes to the nucleic acid target sequence. This stem-loop structure is typically in the range of 15 to 19 nucleotides in length. Substitutions that disrupt this stem-loop duplex abolish cleavage activity, whereas other substitutions that do not disrupt the stem-loop duplex and do not abolish cleavage activity. Nucleotides 5' of the stem loop adopt a pseudo-knot structure further stabilizing the stem-loop structure with non-canonical Watson-Crick base pairing, triplex interaction, and reverse Hoogsteen base pairing (see Yamano, T., et al., Cell 165(4): 949-962 (2016)). In Type V systems, the crRNA forms a stem-loop structure in the 5'-end sequences, and the sequence of the 3'-end sequence is complementary to a sequence in a nucleic acid target sequence.

Other proteins associated with Type V crRNA and nucleic acid target sequence binding and cleavage include Class 2 candidate 1 (C2c1) and Class 2 candidate 3 (C2c3). C2c1 and C2c3 proteins are similar in length to Cas9 and Cpf1 proteins, ranging from approximately 1,100 amino acids to approximately 1,500 amino acids. C2c1 and C2c3 proteins also contain RuvC-like nuclease domains and have an architecture similar to Cpf1. C2c1 proteins are similar to Cas9 proteins in requiring a crRNA and a tracrRNA for nucleic acid target sequence binding and cleavage but have an optimal cleavage temperature of 50° C. C2c1 proteins target an AT-rich protospacer adjacent motif (PAM), similar to the PAM of Cpf1, which is 5' of the nucleic acid target sequence (see, e.g., Shmakov, S., et al., Molecular Cell 60(3):385-397 (2015)).

Class 2 candidate 2 (C2c2) does not share sequence similarity with other CRISPR effector proteins and was recently identified as a Type VI system (see Abudayyeh, O., et al., Science 353(6299):aaf5573 (2016)). C2c2 proteins have two HEPN domains and demonstrate single-stranded RNA cleavage activity. C2c2 proteins are similar to Cpf1 proteins in requiring a crRNA for nucleic acid target sequence binding and cleavage, although not requiring tracrRNA. Also, similar to Cpf1, the crRNA for C2c2 proteins forms a stable hairpin, or stem-loop structure, that aids in association with the C2c2 protein. Type VI systems have a single polypeptide RNA endonuclease that utilizes a single crRNA to direct site-specific cleavage. Additionally, after hybridizing to the target RNA complementary to the spacer, C2c2 becomes a promiscuous RNA endonuclease exhibiting non-specific endonuclease activity toward any single-stranded RNA in a sequence independent manner (see East-Seletsky, A., et al., Nature 538(7624):270-273 (2016)).

Regarding Class 2 Type II CRISPR-Cas systems, a large number of Cas9 orthologs are known in the art as well as their associated polynucleotide components (tracrRNA and crRNA) (see, e.g., Fonfara, I., et al., Nucleic Acids Research 42(4):2577-2590 (2014), including all Supplemental Data; Chylinski K., et al., Nucleic Acids Research 42(10):6091-6105 (2014), including all Supplemental Data). In addition, Cas9-like synthetic proteins are known in the art (see U.S. Published Patent Application No. 2014-0315985, published 23 Oct. 2014).

Cas9 is an exemplary Type II CRISPR Cas protein. Cas9 is an endonuclease that can be programmed by the tracrRNA/crRNA to cleave, in a site-specific manner, a DNA target sequence using two distinct endonuclease domains (HNH and RuvC./RNase H-like domains) (see U.S. Published Patent Application No. 2014-0068797, published 6 March 2014; see also Jinek, M., et al., Science 337:816-821 (2012)).

Typically, each wild-type CRISPR-Cas9 system includes a crRNA and a tracrRNA. The crRNA has a region of complementarity to a potential DNA target sequence and a second region that forms base-pair hydrogen bonds with the tracrRNA to form a secondary structure, typically to form at least one stem structure. The region of complementarity to the DNA target sequence is the spacer. The tracrRNA and a crRNA interact through a number of base-pair hydrogen bonds to form secondary RNA structures. Complex formation between tracrRNA/crRNA and Cas9 protein results in conformational change of the Cas9 protein that facilitates binding to DNA, endonuclease activities of the Cas9 protein, and crRNA-guided site-specific DNA cleavage by the endonuclease Cas9. For a Cas9 protein/tracrRNA/crRNA complex to cleave a double-stranded DNA target sequence, the DNA target sequence is adjacent to a cognate PAM. By engineering a crRNA to have an appropriate spacer sequence, the complex can be targeted to cleave at a locus of interest, e.g., a locus at which sequence modification is desired.

A variety of Type II CRISPR-Cas system crRNA and tracrRNA sequences, as well as predicted secondary structures are known in the art (see, e.g., Ran, F. A., et al., Nature 520(7546):186-191 (2015), including all Supplemental Data, in particular Extended Data FIG. 1; Fonfara, I., et al., Nucleic Acids Research 42(4):2577-2590 (2014), including all Supplemental Data, in particular Supplemental Figure S11). Predicted tracrRNA secondary structures were based on the Constraint Generation RNA folding model (Zuker, M., Nucleic Acids Research 31:3406-3415 (2003). RNA duplex secondary structures were predicted using RNAcofold of the Vienna RNA package (Bernhart, S. H., et al., Algorithms for Molecular Biology 1(1):3 (2006); Hofacker, I. L., et al., Journal of Molecular Biology 319:1059-1066 (2002)) and RNAhybrid (bibiserv.techfak.uni-bielefeld.de/rnahybrid/). The structure predictions were visualized using VARNA (Darty, K., et al., Bioinformatics 25:1974-1975 (2009)). Fonfara, I., et al., show that the crRNA/tracrRNA complex for *Campylobacter jejuni* does not have the bulge region; however, the complex retains a stem structure located 3' of the spacer that is followed in the 3' direction with another stem structure.

The spacer of Class 2 CRISPR-Cas systems can hybridize to a nucleic acid target sequence that is located 5' or 3' of a PAM, depending upon the Cas protein to be used. A PAM can vary depending upon the Cas polypeptide to be used. For example, if Cas9 from *S. pyogenes* is used, the PAM can be a sequence in the nucleic acid target sequence that comprises the sequence 5'-NRR-3', wherein R can be either A or G, N is any nucleotide, and N is immediately 3' of the nucleic acid target sequence targeted by the nucleic acid target binding sequence. A Cas protein may be modified such that a PAM may be different compared with a PAM for an unmodified Cas protein. For example, if Cas9 from *S. pyogenes* is used, the Cas9 protein may be modified such that the PAM no longer comprises the sequence 5'-NRR-3', but instead comprises the sequence 5'-NNR-3', wherein R can be either A or G, N is any nucleotide, and N is immediately 3' of the nucleic acid target sequence targeted by the nucleic acid target sequence.

Other Cas proteins recognize other PAMs, and one of skill in the art is able to determine the PAM for any particular Cas protein. For example, Cpf1 has a thymine-rich PAM site that targets, for example, a TTTN sequence (see Fagerlund, R., et al., Genome Biology 16:251 (2015)).

The RNA-guided Cas9 endonuclease has been widely used for programmable genome editing in a variety of organisms and model systems (see, e.g., Jinek M., et al., Science 337:816-821 (2012); Jinek M., et al., eLife 2:e00471. doi: 10.7554/eLife.00471 (2013); U.S. Published Patent Application No. 2014-0068797, published 6 Mar. 2014).

Genome engineering includes altering the genome by deleting, inserting, mutating, or substituting specific nucleic acid sequences. The alteration can be gene- or location-specific. Genome engineering can use site-directed nucleases, such as Cas proteins and their cognate polynucleotides, to cut DNA, thereby generating a site for alteration. In certain cases, the cleavage can introduce a double-strand break (DSB) in the DNA target sequence. DSBs can be repaired, e.g., by non-homologous end joining (NHEJ), microhomology-mediated end joining (MMEJ), or homology-directed repair (HDR). HDR relies on the presence of a template for repair. In some examples of genome engineering, a donor polynucleotide or portion thereof can be inserted into the break.

SUMMARY OF THE INVENTION

The present invention generally relates to engineered Class 2 Type II CRISPR-Cas9-associated discontinuous nucleic-acid targeting nucleic acids, and nucleoprotein complexes comprising such nucleic acids, as well as compositions and methods of use thereof.

In one aspect the present invention relates to a Class 2 Type II CRISPR-Cas9-associated discontinuous first-stem nucleic-acid targeting nucleic acid (dfs-NATNA) composition comprising a first Class 2 Type II CRISPR-Cas9-associated discontinuous first-stem single-strand polynucleotide (dfs1-PN) and a second Class 2 Type II CRISPR-Cas9-associated discontinuous first-stem single-strand polynucleotide (dfs2-PN). The dfs1-PN comprises, in a 5' to 3' direction, a first stem element nucleotide sequence I, a nexus nucleotide sequence, and a 3' hairpin element. The dfs2-PN comprises, in a 5' to 3' direction, a nucleic acid target binding sequence and a first stem element nucleotide sequence II. The first stem element nucleotide sequence I and the first stem element nucleotide sequence II form a first stem element through hydrogen base-pair bonding, and a first stem-loop element nucleotide sequence covalently connects the first stem element nucleotide sequence I and the first stem element nucleotide sequence II to form a first stem-loop element. The first stem-loop element comprises a lower stem element 3' of the nucleic acid targeting sequence and 5' of the nexus nucleotide sequence, and the lower stem element is adjacent a bulge element, the bugle element is adjacent an upper stem element, and the upper stem element is adjacent a first stem-loop element. Embodiments of the present invention include, but are not limited to, the lower stem element comprising at least a pair of hydrogen-bonded nucleotides at a 5' terminus of the dfs1-PN and at least a pair of hydrogen-bonded nucleotides at a 3' terminus of the dfs2-PN; the upper stem element comprising at least a pair of hydrogen-bonded nucleotides at a 5' terminus of the dfs1-PN and at least a pair of hydrogen-bonded nucleotides at a 3' terminus of the dfs2-PN; the bulge element comprising at least a pair of hydrogen-bonded nucleotides at a 5' terminus of the dfs1-PN and at least a pair of hydrogen-bonded nucleotides at a 3' terminus of the dfs2-PN; and combinations thereof.

In a preferred embodiment, the lower stem element comprises at least a pair of hydrogen-bonded nucleotides at a 5' terminus of the dfs1-PN and at least a pair of hydrogen-bonded nucleotides at a 3' terminus of the dfs2-PN.

In some embodiments, the lower stem element further comprises a lower stem element nucleotide sequence I and a lower stem element nucleotide sequence II, wherein the lower stem element nucleotide sequence I or the lower stem element nucleotide sequence II comprises the 5' terminus of the dfs1-PN and the 3' terminus of the dfs2-PN. Furthermore, the lower stem element comprises at least the pair of hydrogen-bonded nucleotides at a 5' terminus of the dfs1-PN and at least the pair of hydrogen-bonded nucleotides at a 3' terminus of the dfs2-PN.

In additional embodiments, the first stem element nucleotide sequence I further comprises, in a 5' to 3' direction, an upper stem element nucleotide sequence I, a bulge element nucleotide sequence I, and an upper stem element nucleotide sequence I. The first stem element nucleotide sequence II further comprises, in a 5' to 3' direction, a lower stem element nucleotide sequence II, a bulge element nucleotide sequence II, and a lower stem element nucleotide sequence II. The upper stem element nucleotide sequence I and the upper stem element nucleotide sequence II form the upper stem element by base-pair hydrogen bonding between the upper stem element nucleotide sequence I and the upper stem element nucleotide sequence II, the bulge element nucleotide sequence I and the bulge element nucleotide sequence II form the bulge element, and the lower stem element nucleotide sequence I and the lower stem element nucleotide sequence II form the lower stem element by base-pair hydrogen bonding between the lower stem element nucleotide sequence I and the lower stem element nucleotide sequence II.

An example of a range of lengths for the lower stem nucleotide sequence I and the lower stem element nucleotide sequence II include, but is not limited, wherein each sequence is between 2 and 10 nucleotides in length.

In some embodiments, the lower stem nucleotide sequence I further comprises, in a 5' to 3' direction, a fragment nucleotide sequence 2 comprising at least one nucleotide and the 3' terminus of the dfs2-PN, and a fragment nucleotide sequence 1 comprising the 5' terminus of the dfs1-PN and at least one nucleotide. The lower stem element nucleotide sequence I and the lower stem element nucleotide sequence II form a stem element comprising at least 2 pairs of hydrogen-bonded nucleotides.

In further embodiments, the lower stem nucleotide sequence II further comprises, in a 5' to 3' direction, a fragment nucleotide sequence 2 comprising at least one nucleotide and the 3' terminus of the dfs2-PN, and a fragment nucleotide sequence 1 comprising the 5' terminus of the dfs1-PN and at least one nucleotide. The lower stem element nucleotide sequence I and the lower stem element nucleotide sequence II form a stem element comprising at least 2 pairs of hydrogen-bonded nucleotides.

In some embodiments of the present invention, the upper stem nucleotide sequence I and the upper stem element nucleotide sequence II are each between 2 and 22 nucleotides in length.

An example of ranges of sequence lengths for a dfs-NATNA composition is wherein the lower stem nucleotide sequence I and the lower stem element nucleotide sequence II are each 9 nucleotides in length, the bulge element nucleotide sequence I is 3 nucleotides in length, the bulge element nucleotide sequence II is 1 nucleotide in length, and the upper stem element nucleotide sequence I and the upper stem element nucleotide sequence II are each between 3-20 nucleotides in length. Another example of ranges of sequence lengths for a dfs-NATNA composition is wherein the lower stem nucleotide sequence I and the lower stem element nucleotide sequence II are each 6 nucleotides in length, the bulge element nucleotide sequence I is 4 nucleotides in length, the bulge element nucleotide sequence II is 2 nucleotide in length, and the upper stem element nucleotide sequence I and the upper stem element nucleotide sequence II are each between 4-20 nucleotides in length.

The component polynucleotides of dfs-NATNA compositions of the present invention can comprise additional elements and sequences. In some embodiments, the dfs1-PN further comprises a nexus 3' linker nucleotide sequence 5' to the 3' hairpin. In other embodiments, the dfs1-PN further comprises an additional hairpin element 3' of the 3' hairpin element.

The polynucleotide components of a dfs-NATNA composition (e.g., dfs1-PN, dfs2-PN, or dfs1-PN and dfs2-PN) can comprise DNA, RNA, or DNA and RNA.

In further embodiments, polynucleotide components of a dfs-NATNA composition (e.g., dfs1-PN, dfs2-PN, or dfs1-PN and dfs2-PN) can comprise one or more a thiol moieties.

Embodiments of the present invention include dfs-NATNA compositions wherein the pair of hydrogen-bonded nucleotides at the 5' terminus of the dfs1-PN is a pair of Watson-Crick-hydrogen-bonded nucleotides, and the pair of hydrogen-bonded nucleotides at the 3' terminus of the dfs2-PN is a pair of Watson-Crick-hydrogen-bonded nucleotides or wobble-hydrogen-bonded nucleotides. In some embodiments, the pair of hydrogen-bonded nucleotides at the 3' terminus of the dfs2-PN is a pair of Watson-Crick-hydrogen-bonded nucleotides.

In another aspect, the present invention includes a nucleoprotein composition comprising a dfs-NATNA composition and a Cas9 protein. In some embodiments the Cas9 protein is a *Streptococcus pyogenes* Cas9 protein, a *Staphylococcus aureus* Cas9 protein, or a *Streptococcus thermophilus* Cas9 protein. In further embodiments of the nucleoprotein composition, the dfs-NATNA composition is in a complex with the Cas9 protein. Embodiments of the present invention include an enzymatically inactive Cas9 protein.

In a further aspect, the present invention relates to kits comprising one or more components of a dfs-NATNA composition. In some embodiments, the dfs-NATNA composition comprises a dfs1-PN and a dfs2-PN, or one or more nucleic acid sequences encoding the dfs1-PN and the dfs2-PN, and a buffer. Kits can further comprise one or more Cas9 proteins or one or more nucleic acid sequences encoding the one or more Cas9 proteins. In further embodiments, a kit can comprise nucleoprotein complexes comprising a dfs-NATNA composition and a Cas9 protein.

In an additional aspect, the present invention relates to an expression vector comprising one or more nucleic acid sequences encoding one or more components of a dfs-NATNA composition.

In yet another aspect, the present invention relates to a recombinant cell comprising one or more nucleic acid sequences encoding one or more components of a dfs-NATNA composition.

Further aspects of the present invention include methods of using a dfs-NATNA composition including, but not limited to, a method of binding DNA. This method comprises contacting a first DNA target sequence in a DNA polynucleotide with a nucleoprotein complex comprising a dfs-NATNA composition and a Cas9 protein, thereby facilitating binding of the nucleoprotein complex to the first DNA target sequence in the DNA polynucleotide.

Another method of the present invention is a method of cutting DNA. The method comprises contacting a first DNA target sequence in the DNA polynucleotide with a nucleoprotein complex comprising a dfs-NATNA composition and a Cas9 protein, thereby facilitating binding of the nucleoprotein complex to the first DNA target sequence. Such binding results in cutting of the first DNA target sequence.

These aspects and other embodiments of the present invention using the dfs-NATNA compositions and nucleoprotein complexes comprising the dfs-NATNA compositions of the present invention will be readily apparent to those of ordinary skill in the art in view of the disclosure herein.

BRIEF DESCRIPTION OF THE FIGURES

The figures are not proportionally rendered, nor are they to scale. The locations of indicators are approximate.

INCORPORATION BY REFERENCE

Figure 1A:
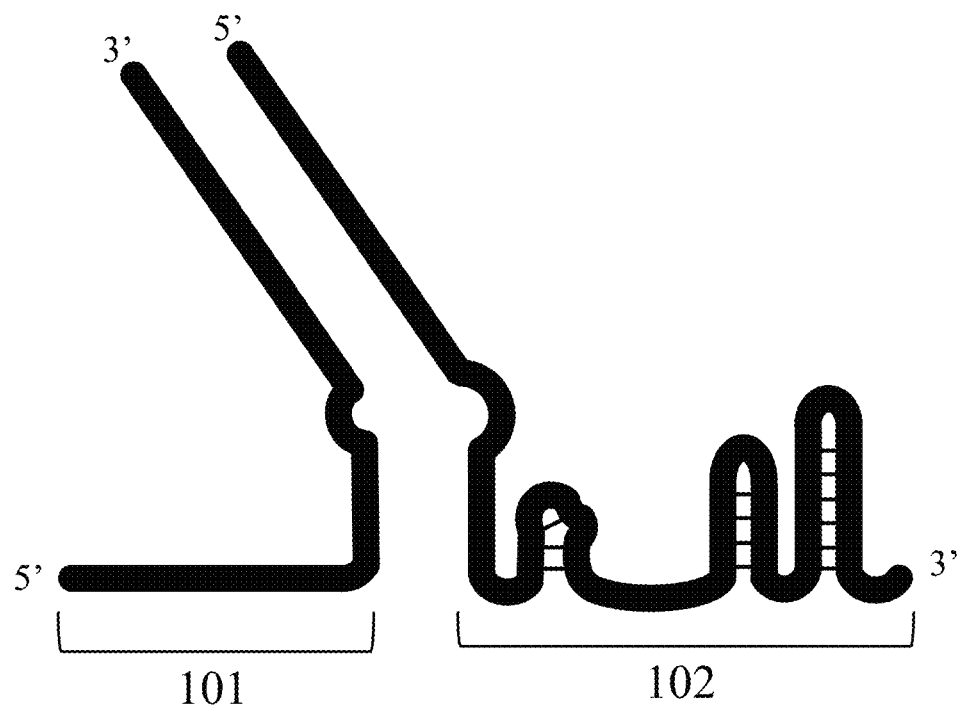
FIG. 1A and FIG. 1B present illustrative examples of dual-guide Class 2 Type II CRISPR-Cas9-associated guide RNAs.

All patents, publications, and patent applications cited in this specification are herein incorporated by reference as if each individual patent, publication, or patent application was specifically and individually indicated to be incorporated by reference in its entirety for all purposes.

DETAILED DESCRIPTION OF THE INVENTION

It is to be understood that the terminology used herein is for the purpose of describing particular embodiments only, and is not intended to be limiting. As used in this specification and the appended claims, the singular forms "a," "an"

and "the" include plural referents unless the context clearly dictates otherwise. Thus, for example, reference to "a polynucleotide" includes one or more polynucleotides, and reference to "a vector" includes one or more vectors.

Unless defined otherwise, all technical and scientific terms used herein have the same meaning as commonly understood by one of ordinary skill in the art to which the invention pertains. Although other methods and materials similar, or equivalent, to those described herein can be useful in the present invention, preferred materials and methods are described herein.

In view of the teachings of the present specification, one of ordinary skill in the art can employ conventional techniques of immunology, biochemistry, chemistry, molecular biology, microbiology, cell biology, genomics, and recombinant polynucleotides, as taught, for example, by the following standard texts: Antibodies: A Laboratory Manual., Second edition, E. A. Greenfield, Cold Spring Harbor Laboratory Press, ISBN 978-1-936113-81-1 (2014); Culture of Animal Cells: A Manual of Basic Technique and Specialized Applications, 6th Edition, R. I. Freshney, Wiley-Blackwell, ISBN 978-0-470-52812-9 (2010); Transgenic Animal Technology, Third Edition: A Laboratory Handbook, C. A. Pinkert, Elsevier, ISBN 978-0124104907 (2014); The Laboratory Mouse, Second Edition, H. Hedrich, Academic Press, ISBN 978-0123820082 (2012); Manipulating the Mouse Embryo: A Laboratory Manual., R. Behringer, et al., Cold Spring Harbor Laboratory Press, ISBN 978-1936113019 (2013); PCR 2: A Practical Approach, M. J. McPherson, et al., IRL Press, ISBN 978-0199634248 (1995); Methods in Molecular Biology (Series), J. M. Walker, ISSN 1064-3745, Humana Press; RNA: A Laboratory Manual., D. C. Rio, et al., Cold Spring Harbor Laboratory Press, ISBN 978-0879698911 (2010); Methods in Enzymology (Series), Academic Press; Molecular Cloning: A Laboratory Manual (Fourth Edition), M. R. Green, et al., Cold Spring Harbor Laboratory Press, ISBN 978-1605500560 (2012); Bioconjugate Techniques, Third Edition, G. T. Hermanson, Academic Press, ISBN 978-0123822390 (2013); Methods in Plant Biochemistry and Molecular Biology, W. V. Dashek, CRC Press, ISBN 978-0849394805 (1997); Plant Cell Culture Protocols (Methods in Molecular Biology), V. M. Loyola-Vargas, et al., Humana Press, ISBN 978-1617798177 (2012); Plant Transformation Technologies, C. N. Stewart, et al., Wiley-Blackwell, ISBN 978-0813821955 (2011); Recombinant Proteins from Plants (Methods in Biotechnology), C. Cunningham, et al., Humana Press, ISBN 978-1617370212 (2010); Plant Genomics: Methods and Protocols (Methods in Molecular Biology), D. J. Somers, et al., Humana Press, ISBN 978-1588299970 (2009); Plant Biotechnology: Methods in Tissue Culture and Gene Transfer, R. Keshavachandran, et al., Orient Blackswan, ISBN 978-8173716164 (2008).

Clustered regularly interspaced short palindromic repeats (CRISPR) and related CRISPR-associated proteins (Cas proteins) constitute CRISPR-Cas systems (see, e.g., Barrangou, R., et al., Science 315:1709-1712 (2007)).

As used herein, "Cas protein" and "CRISPR-Cas protein" refer to Cas proteins including, but not limited to, Class 1 Type I Cas proteins, Class 1 Type III Cas proteins, Class 1 Type IV Cas proteins, Class 2 Type II Cas proteins, Class 2 Type V Cas proteins, and Class 2 Type VI Cas proteins. Class 2 Cas proteins include Cas9 proteins, Cas9-like proteins encoded by Cas9 orthologs, Cas9-like synthetic proteins, Cpf1 proteins, proteins encoded by Cpf1 orthologs, Cpf1-like synthetic proteins, C2c1 proteins, C2c2 proteins, C2c3 proteins, and variants and modifications thereof. In some embodiments, Cas proteins are Class 2 Cas proteins, for example one or more Class 2 Type II Cas proteins, such as Cas9, one or more Class 2 Type V Cas proteins, such as Cpf1, or one or more Class 2 Type VI Cas proteins, such as C2c2. In preferred embodiments, Cas proteins are one or more Class 2 Type II Cas proteins, such as Cas9, and one or more Class 2 Type V Cas proteins, such as Cpf1. Typically, for use in aspects of the present invention, a Cas protein is capable of interacting with one or more cognate polynucleotides (most typically, RNA) to form a nucleoprotein complex (most typically, a ribonucleoprotein complex).

"Cas9 protein," as used herein, refers to a Cas9 wild-type protein derived from Class 2 Type II CRISPR-Cas9 systems, modifications of Cas9 proteins, variants of Cas9 proteins, Cas9 orthologs, and combinations thereof. Cas9 proteins include, but not limited to, Cas9 from *Streptococcus pyogenes* (UniProtKB-Q99ZW2 (CAS9_STRP1)), *Streptococcus thermophilus* (UniProtKB-G3ECR1 (CAS9_STRTR)), and *Staphylococcus aureus* (UniProtKB-J7RUA5 (CAS9_STAAU)). Cas9 homologs can be identified using sequence similarity search methods known to one skilled in the art. "dCas9," as used herein, refers to variants of Cas9 protein that are nuclease-deactivated Cas9 proteins, also termed "catalytically inactive Cas9 protein," "enzymatically inactive Cas9," "catalytically dead Cas9" or "dead Cas9." Such molecules lack all or a portion of endonuclease activity and can therefore be used to regulate genes in an RNA-guided manner (see Jinek M., et al., Science 337:816-821 (2012)). This is accomplished by introducing mutations to catalytic residues, such as D10A in the RuvC-1 domain and H840A in the HNH domain (numbered relative to *S. pyogenes* Cas9 protein), that inactivate Cas9 nuclease function. It is understood that mutation of other catalytic residues to reduce activity of either or both of the nuclease domains can also be carried out by one skilled in the art. The resultant dCas9 is unable to cleave double-stranded DNA but retains the ability to complex with a guide nucleic acid and bind a DNA target sequence. The Cas9 double mutant with changes at amino acid positions D10A and H840A inactivates both the nuclease and nickase activities. Targeting specificity is determined by Cas9 protein binding to the PAM sequence, and by complementary base pairing of guide RNA (typically, a single guide RNA) to the genomic locus. Cas9 is the signature protein characteristic for Class 2 Type II CRISPR systems.

"Nucleic-acid targeting nucleic acid" (NATNA), as used herein, refers to one or more polynucleotides that guide a protein, such as a Cas protein (preferably a Cas9 protein), to preferentially bind a nucleic acid target sequence in a polynucleotide (relative to a polynucleotide that does not comprise the nucleic acid target sequence). NATNAs can comprise ribonucleotide bases (e.g., RNA), deoxyribonucleotide bases (e.g., DNA), combinations of ribonucleotide bases and deoxyribonucleotide bases (e.g., RNA/DNA), nucleotides, nucleotide analogs, modified nucleotides, and the like, as well as synthetic, naturally occurring, and non-naturally occurring modified backbone residues or linkages, for example, as described herein.

Figure 1B:
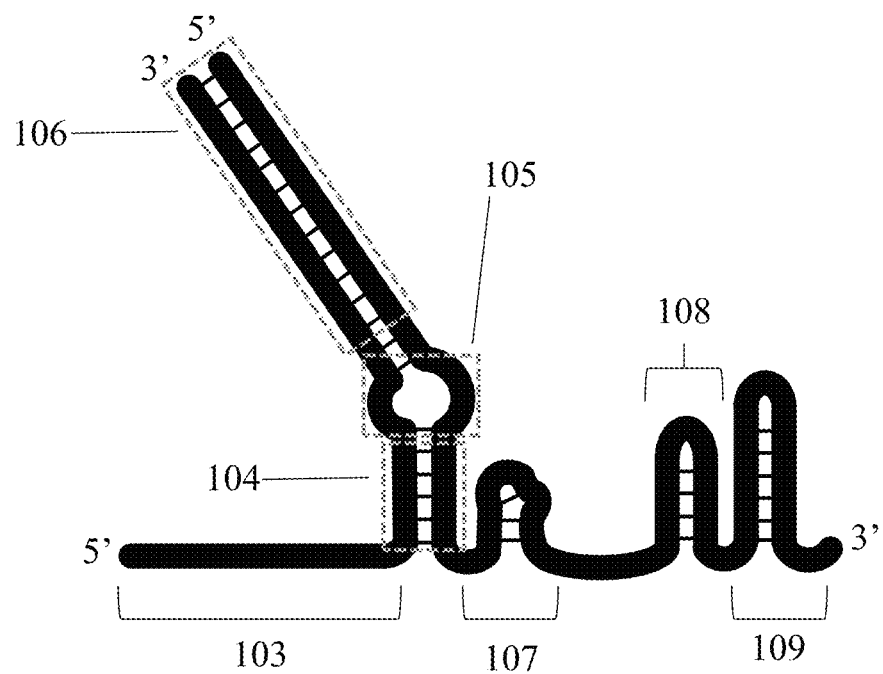

As used herein, "dual-guide RNA" and "Cas9-dual-guide RNA" refer to a two-component RNA system for a polynucleotide component capable of associating with a cognate Cas9 protein, as further described herein. FIG. 1A and FIG. 1B present illustrative examples of Class 2 Type II CRISPR-Cas9-associated dual-guide RNAs. FIG. 1A illustrates a Type II CRISPR-Cas9 system two-component RNA comprising a Cas9-crRNA (FIG. 1A, 101) and a Cas9-tracrRNA (FIG. 1A, 102). FIG. 1B illustrates the formation of base-pair hydrogen bonds between the Cas9-crRNA and the Cas9-tracrRNA to form secondary structure (see U.S. Published Patent Application No. 2014-0068797, published 6 Mar. 2014; see also Jinek M., et al., Science 337:816-21 (2012)). FIG. 1B presents an overview of and nomenclature for secondary structural elements of the Cas9-crRNA and Cas9-tracrRNA of the S. pyogenes Cas9 including the following: a spacer element (FIG. 1B, 103) comprising a spacer sequence (also referred to herein as a nucleic acid target binding sequence); a first stem element (FIG. 1B, 104, 105, 106) comprising a lower stem element (FIG. 1B, 104), a bulge element comprising unpaired nucleotides (FIG. 1B, 105), and an upper stem element (FIG. 1B, 106); a nexus element (FIG. 1B, 107) comprising a second stem element; a first 3' hairpin element (FIG. 1B, 108) comprising a third stem element; and a second 3' hairpin element (FIG. 1B, 109) comprising a fourth stem element. In some Class 2 Type II CRISPR-Cas9 systems, the first stem element does not have a bulge element (e.g., C. jejuni). A Cas9-dual-guide RNA is capable of forming a nucleoprotein complex with a cognate Cas9 protein, wherein the complex is capable of targeting a nucleic acid target sequence complementary to the spacer sequence. Modifications of Cas9-dual-guides are known in the art, including, deletion of one or more 3' hairpin elements (FIG. 1B, 108, 109) and modifications of the upper stem, bulge, and lower stem (FIG. 1B, 106, 105, 104, respectively) (see, e.g., U.S. Patent Publication No. 2014-0315985, published 23 Oct. 2014; U.S. Patent Publication No. 2015-0376586, published 31 Dec. 2015). As used herein, a "dual-guide Cas9 polynucleotide" refers to a two-component system having a polynucleotide with the same structural elements as a crRNA (FIG. 1A, 101) and a polynucleotide with the same structural elements as a tracrRNA (FIG. 1A 102).

Figure 2:
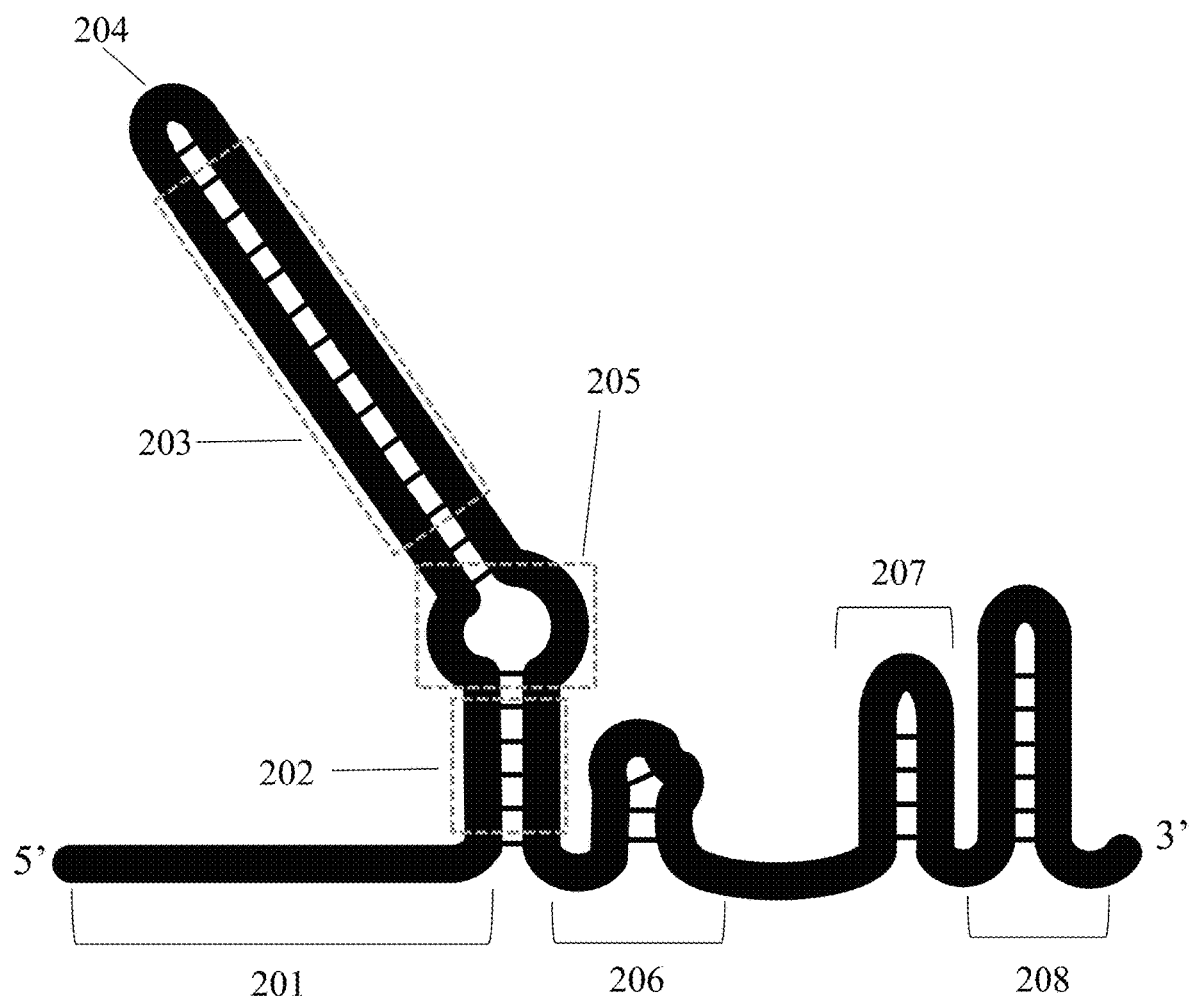
FIG. 2 presents an illustrative example of single-guide Class 2 Type II CRISPR-Cas9-associated guide RNA.

As used herein, "single-guide RNA" (sgRNA) and "Cas9-sgRNA" refer to a one-component RNA system as further described herein, wherein the system is capable of associating with a cognate Cas9 protein. FIG. 2 shows an example of a Class 2 Type II CRISPR-Cas9-associated sgRNA. The figure illustrates a Cas9 single-guide RNA (Cas9-sgRNA) wherein the Cas9-crRNA is covalently joined to the Cas9-tracrRNA, often through a tetraloop, and forms a RNA polynucleotide secondary structure through base-pair hydrogen bonding (see U.S. Published Patent Application No. 2014-0068797, published 6 Mar. 2014). FIG. 2 presents an overview of and nomenclature for secondary structural elements of a Cas9-sgRNA for S. pyogenes including the following: a spacer element (FIG. 2, 201) comprising a spacer sequence (also referred to herein as a nucleic acid targeting nucleic acid sequence); a first stem-loop element (FIG. 2A, 202, 205, 203, 204) comprising a lower stem element (FIG. 2, 202), a bulge element comprising unpaired nucleotides (FIG. 2, 205), an upper stem element (FIG. 2, 203), and a loop element (FIG. 2, 204) comprising unpaired nucleotides; a nexus element (FIG. 2, 206) comprising a second stem-loop element; a first 3' hairpin element (FIG. 2, 207) comprising a third stem-loop element; and a second 3' hairpin element comprising a third stem element (FIG. 2, 208) comprising a fourth stem-loop element (see, e.g., FIGS. 1 and 3 of Briner, A. E., et al., Molecular Cell 56(2):333-339 (2014)). In Class 2 Type II CRISPR-Cas9 systems wherein the first stem element does not have a bulge element, the crRNA can be connected to the tracrRNA to form a sgRNA. A Cas9-sgRNA is capable of forming a nucleoprotein complex with a cognate Cas9 protein, wherein the complex is capable of targeting a nucleic acid sequence complementary to the spacer sequence. Modifications of Cas9 single-guides are known in the art including, but not limited to, deletion of one or more 3' hairpin elements (FIG. 2, 207, 208), modifications of the first stem element and modifications of the upper stem, bulge, and lower stem (FIG. 2, 203, 205, 202, respectively) (see, e.g., U.S. Patent Publication No. 2014-0315985, published 23 Oct. 2014; U.S. Patent Publication No. 2015-0376586, published 31 Dec. 2015). As used herein, a "Cas9 single-guide polynucleotide" refers to a one-component system having the same structural elements as a sgRNA (FIG. 2).

As used herein, the term "cognate" typically refers to a Cas protein (e.g., Cas9 protein) and one or more Cas polynucleotides (e.g., Class 2 Type II CRISPR-Cas9-associated NATNAs) that are capable of forming a nucleoprotein complex capable of site-directed binding to a nucleic acid target sequence complementary to the nucleic acid target binding sequence present in one of the one or more Cas polynucleotides.

The terms "wild-type," "naturally occurring," and "unmodified" are used herein to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in, and can be isolated from, a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," "non-naturally occurring," "non-natural.," and "non-native" are interchangeable and indicate intentional human manipulation.

As used herein, "interrupted," "broken," and "discontinuous" are used interchangeably to mean a break in continuity, e.g., in covalent bonds of a polynucleotide backbone. For example, a first polynucleotide and a second polynucleotide that are discontinuous each have a 5' terminus and a 3' terminus (5' terminus-first polynucleotide-3' terminus and 5' terminus-second polynucleotide-3' terminus, respectively). Examples of termini include, but are not limited to, termini wherein the 5' terminus of a DNA or RNA molecule is the fifth carbon in the sugar ring and the 3' terminus is the hydroxyl group on the third carbon in the sugar ring. Two polynucleotides, each having a 5' terminus and a 3' terminus, are formed when the backbone of a single polynucleotide is broken at one site. A 5' and/or 3' terminus can be covalently modified, for example, by addition of a moiety (e.g., a moiety providing resistance to the degradative effects of exonucleases).

"Covalent bond," "covalently attached," "covalently bound," "covalently linked," "covalently connected," and "molecular bond" are used interchangeably herein, and refer to a chemical bond that involves the sharing of electron pairs between atoms. Examples of covalent bonds include, but are not limited to, phosphodiester bonds and phosphorothioate bonds.

"Non-covalent bond," "non-covalently attached," "non-covalently bound," "non-covalently linked," "non-covalent interaction," and "non-covalently connected" are used interchangeably herein, and refer to any relatively weak chemical bond that does not involve sharing of a pair of electrons. Multiple non-covalent bonds often stabilize the conformation of macromolecules and mediate specific interactions between molecules. Examples of non-covalent bonds include, but are not limited to hydrogen bonding, ionic interactions (e.g., Na⁺Cl⁻), van der Waals interactions, and hydrophobic bonds.

As used herein, "hydrogen bonding," "hydrogen base pairing," and "hydrogen bonded" are used interchangeably and refer to canonical hydrogen bonding and non-canonical hydrogen bonding including, but not limited to, "Watson-Crick-hydrogen-bonded base pairs" (W-C-hydrogen-bonded base pairs or W-C hydrogen bonding); "Hoogsteen-hydrogen-bonded base pairs" (Hoogsteen hydrogen bonding); and "wobble-hydrogen-bonded base pairs" (wobble hydrogen bonding). W-C hydrogen bonding, including reverse W-C hydrogen bonding, refers to purine-pyrimidine base pairing, that is, adenine:thymine, guanine:cytosine, and uracil:adenine. Hoogsteen hydrogen bonding, including reverse Hoogsteen hydrogen bonding, refers to a variation of base pairing in nucleic acids wherein two nucleobases, one on each strand, are held together by hydrogen bonds in the major groove. This non-W-C hydrogen bonding can allow a third strand to wind around a duplex and form triple-stranded helices. Wobble hydrogen bonding, including reverse wobble hydrogen bonding, refers to a pairing between two nucleotides in RNA molecules that does not follow Watson-Crick base pair rules. There are four major wobble base pairs: guanine:uracil, inosine (hypoxanthine):uracil, inosine-adenine, and inosine-cytosine. Rules for canonical hydrogen bonding and non-canonical hydrogen bonding are known to those of ordinary skill in the art (see, e.g., The RNA World, Third Edition (Cold Spring Harbor Monograph Series), R. F. Gesteland, Cold Spring Harbor Laboratory Press, ISBN 978-0879697396 (2005); The RNA World, Second Edition (Cold Spring Harbor Monograph Series), R. F. Gesteland, et al., Cold Spring Harbor Laboratory Press, ISBN 978-0879695613 (1999); The RNA World (Cold Spring Harbor Monograph Series), R. F. Gesteland, et al., Cold Spring Harbor Laboratory Press, ISBN 978-0879694562 (1993) (see, e.g., Appendix 1: Structures of Base Pairs Involving at Least Two Hydrogen Bonds, I. Tinoco); Principles of Nucleic Acid Structure, W. Saenger, Springer International Publishing AG, ISBN 978-0-387-90761-1 (1988); Principles of Nucleic Acid Structure, First Edition, S. Neidle, Academic Press, ISBN 978-01236950791 (2007)).

"Connect," "connected," and "connecting" are used interchangeably herein, and refer to a covalent bond or a non-covalent bond between two macromolecules (e.g., polynucleotides, proteins, and the like).

As used herein, the term "a Class 2 Type II CRISPR-Cas9-associated discontinuous first-stem nucleic-acid targeting nucleic acid (dfs-NATNA)" composition refers to engineered Cas-associated NATNAs (e.g., Cas9-associated NATNAs) wherein the first stem element (see, e.g., FIG. 1B, 104, 105, 106; and FIG. 2, 202, 203, 205) comprises an engineered break in the nucleic acid backbone resulting in at least one non-native 5' terminus and one non-native 3' terminus in the first stem element. In some embodiments, a first stem-loop element comprises the first stem element and a loop element. The first stem element comprises: a lower stem element 3' of the nucleic acid targeting sequence and 5' of the nexus nucleotide sequence; the lower stem element is adjacent to a bulge element; the bugle element is adjacent to an upper stem element; and the upper stem element is adjacent to a loop element (see, e.g., FIG. 2, 202, 205, 203, 204). A dfs-NATNA (or dfs-NATNA composition) comprises at least a first Class 2 Type II CRISPR-Cas9-associated discontinuous first-stem single-strand polynucleotide (dfs1-PN) comprising, in a 5' to 3' direction, a non-native 5' terminus and a nexus nucleotide sequence, and a second Class 2 Type II CRISPR-Cas9-associated discontinuous first-stem single-strand polynucleotide (dfs2-PN) comprising, in a 5' to 3' direction, a nucleic acid target binding sequence and a non-native 3' terminus. A dfs-NATNA generically comprises two or more dfs polynucleotides (dfs-PNs; one polynucleotide component of a dfs-NATNA is referred to as a dfs-PN). In one embodiment, a dfs-NATNA comprises a dfs1-PN and a dfs1-PN. The terms "nucleic acid target binding sequence" and "spacer sequence" are used interchangeably herein.

As used herein, "complementarity" refers to the ability of a nucleic acid sequence to form hydrogen bond(s) with another nucleic acid sequence (e.g., through canonical Watson-Crick base pairing). A percent complementarity indicates the percentage of residues in a nucleic acid molecule that can form hydrogen bonds with a second nucleic acid sequence. If two polynucleotide sequences have 100% complementarity, the two sequences are perfectly complementary, i.e., all of the contiguous residues of a first polynucleotide hydrogen bond with the same number of contiguous residues in a second polynucleotide.

As used herein, "binding" refers to a non-covalent interaction between macromolecules (e.g., between a protein and a polynucleotide, between a polynucleotide and a polynucleotide, or between a protein and a protein, and the like). Such non-covalent interaction is also referred to as "associating" or "interacting" (e.g., if a first macromolecule interacts with a second macromolecule, the first macromolecule binds to second macromolecule in a non-covalent manner). Some portions of a binding interaction may be sequence-specific (the terms "sequence-specific binding," "sequence-specifically bind," "site-specific binding," and "site specifically binds" are used interchangeably herein). Sequence-specific binding, as used herein, typically refers to one or more NATNAs capable of forming a complex with a protein (e.g., a Cas9 protein) to cause the protein to bind a nucleic acid sequence (e.g., a DNA sequence) comprising a nucleic acid target sequence (e.g., a DNA target sequence) preferentially relative to a second nucleic acid sequence (e.g., a second DNA sequence) without the nucleic acid target binding sequence (e.g., the DNA target binding sequence). All components of a binding interaction do not need to be sequence-specific, such as contacts of a protein with phosphate residues in a DNA backbone. Binding interactions can be characterized by a dissociation constant (Kd). "Binding affinity" refers to the strength of the binding interaction. An increased binding affinity is correlated with a lower Kd.

As used herein, a Cas protein (e.g., a Cas9 protein) is said to "target" a polynucleotide if a Cas protein/NATNA nucleoprotein complex binds or cleaves a polynucleotide at the nucleic acid target sequence within the polynucleotide.

As used herein, "double-strand break" (DSB) refers to both strands of a double-stranded segment of DNA being severed. In some instances, if such a break occurs, one strand can be said to have a "sticky end" wherein nucleotides are exposed and not hydrogen bonded to nucleotides on the other strand. In other instances, a "blunt end" can occur wherein both strands remain fully base paired with each other.

"Donor polynucleotide," "donor oligonucleotide," and "donor template" are used interchangeably herein and can be a double-strand polynucleotide (e.g., DNA), a single-stranded polynucleotide (e.g., DNA oligonucleotides), or a combination thereof. Donor polynucleotides comprise homology arms flanking the insertion sequence (e.g., DSBs in the DNA). The homology arms on each side can vary in length. Parameters for the design and construction of donor polynucleotides are well-known in the art (see, e.g., Ran, F., et al., Nature Protocols 8(11):2281-2308 (2013); Smithies, O., et al., Nature 317:230-234 (1985); Thomas, K., et al., Cell 44:419-428 (1986); Wu, S., et al., Nature Protocols 3:1056-1076 (2008); Singer, B., et al., Cell 31:25-33 (1982); Shen, P., et al., Genetics 112:441-457 (1986); Watt, V., et al., Proceedings of the National Academy of Sciences of the United States of America 82:4768-4772 (1985); Sugawara, N., et al., Journal of Molecular Cell Biology 12(2):563-575 (1992); Rubnitz, J., et al., Journal of Molecular Cell Biology 4(11):2253-2258 (1984); Ayares, D., et al., Proceedings of the National Academy of Sciences of the United States of America 83(14):5199-5203 (1986); Liskay, R, et al., Genetics 115(1):161-167 (1987)).

As used herein, "homology-directed repair" (HDR) refers to DNA repair that takes place in cells, for example, during repair of a DSB in DNA. HDR requires nucleotide sequence homology and uses a donor polynucleotide to repair the sequence wherein the DSB (e.g., within a DNA target sequence) occurred. The donor polynucleotide generally has the requisite sequence homology with the sequence flanking the DSB so that the donor polynucleotide can serve as a suitable template for repair. HDR results in the transfer of genetic information from, for example, the donor polynucleotide to the DNA target sequence. HDR may result in alteration of the DNA target sequence (e.g., insertion, deletion, or mutation) if the donor polynucleotide sequence differs from the DNA target sequence and part or all of the donor polynucleotide is incorporated into the DNA target sequence. In some embodiments, an entire donor polynucleotide, a portion of the donor polynucleotide, or a copy of the donor polynucleotide is integrated at the site of the DNA target sequence. For example, a donor polynucleotide can be used for repair of the break in the DNA target sequence, wherein the repair results in the transfer of genetic information (i.e., polynucleotide sequences) from the donor polynucleotide at the site or in close proximity of the break in the DNA. Accordingly, new genetic information (i.e., polynucleotide sequences) may be inserted or copied at a DNA target sequence.

A "genomic region" is a segment of a chromosome in the genome of a host cell that is present on either side of the nucleic acid target sequence site or, alternatively, also includes a portion of the nucleic acid target sequence site. The homology arms of the donor polynucleotide have sufficient homology to undergo homologous recombination with the corresponding genomic regions. In some embodiments, the homology arms of the donor polynucleotide share significant sequence homology to the genomic region immediately flanking the nucleic acid target sequence site; it is recognized that the homology arms can be designed to have sufficient homology to genomic regions farther from the nucleic acid target sequence site.

As used herein, "non-homologous end joining" (NHEJ) refers to the repair of a DSB in DNA by direct ligation of one terminus of the break to the other terminus of the break without a requirement for a donor polynucleotide. NHEJ is a DNA repair pathway available to cells to repair DNA without the use of a repair template. NHEJ in the absence of a donor polynucleotide often results in nucleotides being randomly inserted or deleted at the site of the DSB.

"Microhomology-mediated end joining" (MMEJ) is pathway for repairing a DSB in DNA. MMEJ involves deletions flanking a DSB and alignment of microhomologous sequences internal to the break site before joining. MMEJ is genetically defined and requires the activity of, for example, CtIP, Poly(ADP-Ribose) Polymerase 1 (PARP1), DNA polymerase theta (Pol 0), DNA Ligase 1 (Lig 1), or DNA Ligase 3 (Lig 3). Additional genetic components are known in the art (see, e.g., Sfeir, A., et al., Trends in Biochemical Sciences 40:701-714 (2015)).

As used herein, "DNA repair" encompasses any process whereby cellular machinery repairs damage to a DNA molecule contained in the cell. The damage repaired can include single-strand breaks or double-strand breaks. At least three mechanisms exist to repair DSBs: HDR, NHEJ, and MMEJ. "DNA repair" is also used herein to refer to DNA repair resulting from human manipulation, wherein a target locus is modified, e.g., by inserting, deleting, or substituting nucleotides, all of which represent forms of genome editing.

As used herein, "recombination" refers to a process of exchange of genetic information between two polynucleotides.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, transcription start sites, repressor binding sequences, stem-loop structures, translational initiation sequences, internal ribosome entry sites (IRES), translation leader sequences, transcription termination sequences (e.g., polyadenylation signals and poly-U sequences), translation termination sequences, primer binding sites, and the like.

Regulatory elements include those that direct constitutive, inducible, and repressible expression of a nucleotide sequence in many types of host cells and those that direct expression of the nucleotide sequence only in certain host cells (e.g., tissue-specific regulatory sequences). In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart, M., et al., Cell 41:521-530 (1985)), the SV40 promoter, the dihydrofolate reductase promoter, the β-actin promoter, the phosphoglycerol kinase (PGK) promoter, and the EF1α promoter. It will be appreciated by those skilled in the art that the design of an expression vector may depend on such factors as the choice of the host cell to be transformed, the level of expression desired, and the like. A vector can be introduced into host cells to thereby produce transcripts, proteins, or peptides, including fusion proteins or peptides, encoded by nucleic acids as described herein.

"Gene," as used herein, refers to a polynucleotide sequence comprising exon(s) and related regulatory sequences. A gene may further comprise intron(s) and/or untranslated region(s) (UTR(s)).

As used herein, the term "operably linked" refers to polynucleotide sequences or amino acid sequences placed into a functional relationship with one another. For example, regulatory sequences (e.g., a promoter or enhancer) are "operably linked" to a polynucleotide encoding a gene product if the regulatory sequences regulate or contribute to the modulation of the transcription of the polynucleotide. Operably linked regulatory elements are typically contiguous with the coding sequence. However, enhancers can function if separated from a promoter by up to several kilobases or more. Accordingly, some regulatory elements may be operably linked to a polynucleotide sequence but not contiguous with the polynucleotide sequence. Similarly, translational regulatory elements contribute to the modulation of protein expression from a polynucleotide.

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product(s)." Expression may include splicing the mRNA in a eukaryotic cell, if the polynucleotide is derived from genomic DNA.

As used herein, the term "modulate" refers to a change in the quantity, degree or amount of a function. For example, a dfs-NATNA/Cas9 protein complex, as disclosed herein, may modulate the activity of a promoter sequence by binding to a nucleic acid target sequence at or near the promoter. Depending on the action occurring after binding, the dfs-NATNA/Cas9 protein complex can induce, enhance, suppress, or inhibit transcription of a gene operatively linked to the promoter sequence. Thus, "modulation" of gene expression includes both gene activation and gene repression.

Modulation can be assayed by determining any characteristic directly or indirectly affected by the expression of the target gene. Such characteristics include, e.g., changes in RNA or protein levels, protein activity, product levels, expression of the gene, or activity level of reporter genes. Accordingly, the terms "modulating expression," "inhibiting expression," and "activating expression" of a gene can refer to the ability of a dfs-NATNA/Cas9 protein complex to change, activate, or inhibit transcription of a gene.

"Vector" and "plasmid," as used herein, refer to a polynucleotide vehicle to introduce genetic material into a cell. Vectors can be linear or circular. Vectors can contain a replication sequence capable of effecting replication of the vector in a suitable host cell (i.e., an origin of replication). Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art. The four major types of vectors are plasmids, viral vectors, cosmids, and artificial chromosomes. Typically, vectors comprise an origin of replication, a multicloning site, and/or a selectable marker. An expression vector typically comprises an expression cassette.

As used herein, "expression cassette" refers to a polynucleotide construct generated using recombinant methods or by synthetic means and comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in a vector to form an expression vector.

As used herein, a "targeting vector" is a recombinant DNA construct typically comprising tailored DNA arms, homologous to genomic DNA, that flank elements of a target gene or nucleic acid target sequence (e.g., a DSB). A targeting vector comprises a donor polynucleotide. Elements of the target gene can be modified in a number of ways including deletions and/or insertions. A defective target gene can be replaced by a functional target gene, or in the alternative a functional gene can be knocked out. Optionally, the donor polynucleotide of a targeting vector comprises a selection cassette comprising a selectable marker that is introduced into the target gene. Targeting regions (i.e., nucleic acid target sequences) adjacent or within a target gene can be used to affect regulation of gene expression.

As used herein, the terms "nucleic acid," "nucleic acid sequence," "nucleotide sequence," "oligonucleotide," and "polynucleotide" are interchangeable and refer to a polymeric form of nucleotides. The nucleotides may be deoxyribonucleotides (DNA), ribonucleotides (RNA), analogs thereof, or combinations thereof, and may be of any length. Polynucleotides may perform any function and may have any secondary and tertiary structures. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. The terms also encompass nucleic acids comprising modified backbone residues or linkages, that are synthetic, naturally occurring, and non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (LNA™) (Exiqon, Inc., Woburn, Mass.) nucleosides, glycol nucleic acid, bridged nucleic acids, and morpholino structures.

Peptide-nucleic acids (PNAs) are synthetic homologs of nucleic acids wherein the polynucleotide phosphate-sugar backbone is replaced by a flexible pseudo-peptide polymer. Nucleobases are linked to the polymer. PNAs have the capacity to hybridize with high affinity and specificity to complementary sequences of RNA and DNA.

In phosphorothioate nucleic acids, the phosphorothioate (PS) bond substitutes a sulfur atom for a non-bridging oxygen in the polynucleotide phosphate backbone. This modification makes the internucleotide linkage resistant to nuclease degradation. In some embodiments, phosphorothioate bonds are introduced between the last 3 to 5 nucleotides at the 5'-end or 3'-end sequences of a polynucleotide sequence to inhibit exonuclease degradation. Placement of phosphorothioate bonds throughout an entire oligonucleotide helps reduce degradation by endonucleases as well.

Threose nucleic acid (TNA) is an artificial genetic polymer. The backbone structure of TNA comprises repeating threose sugars linked by phosphodiester bonds. TNA polymers are resistant to nuclease degradation. TNA can self-assemble by base-pair hydrogen bonding into duplex structures.

Linkage inversions can be introduced into polynucleotides through use of "reversed phosphoramidites" (see, e.g., www.ucalgary.ca/dnalab/synthesis/-modifications/linkages). A 3'-3' linkage at a terminus of a polynucleotide stabilizes the polynucleotide to exonuclease degradation by creating an oligonucleotide having two 5'-OH termini but lacking a 3'-OH terminus. Typically, such polynucleotides have phosphoramidite groups on the 5'-OH position and a dimethoxytrityl (DMT) protecting group on the 3'-OH position. Normally, the DMT protecting group is on the 5'-OH and the phosphoramidite is on the 3'-OH.

Polynucleotide sequences are displayed herein in the conventional 5' to 3' orientation unless otherwise indicated.

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., BLAST, CS-BLAST, FASTA, HMMER, L-ALIGN, and the like) available through the worldwide web at sites including, but not limited to, GENBANK (www.ncbi.nlm.nih.gov/genbank/) and EMBL-EBI (www.e-bi.ac.uk.). Sequence identity between two polynucleotides or two polypeptide sequences is generally calculated using the standard default parameters of the various methods or computer programs. A high degree of sequence identity, as used herein, between two polynucleotides or two polypeptides is typically between about 90% identity and 100% identity, for example, about 90% identity or higher, preferably about 95% identity or higher, more preferably about 98% identity or higher. A moderate degree of sequence identity, as used herein, between two polynucleotides or two polypeptides is typically between about 80% identity to about 85% identity, for example, about 80% identity or higher, preferably about 85% identity. A low degree of sequence identity, as used herein, between two polynucleotides or two polypeptides is typically between about 50% identity and 75% identity, for example, about 50% identity, preferably about 60% identity, more preferably about 75% identity. For example, a Cas protein (e.g., a Cas9 comprising amino acid substitutions) can have a low degree of sequence identity, a moderate degree of sequence identity, or a high degree of sequence identity, over its length to a reference Cas protein (e.g., a wild-type Cas9). As another example, a NATNA can have a low degree of sequence identity, a moderate degree of sequence identity, or a high degree of sequence identity, over its length compared to a reference wild-type polynucleotide that complexes with the reference Cas protein (e.g., an sgRNA that forms a complex with Cas9).

As used herein, "hybridization" or "hybridize" or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5° C. to 10° C. below $T_m$; moderate stringency, approximately 0.16M to approximately 0.33M salt, hybridization temperature 20° C. to 29° C. below $T_m$; and low stringency, approximately 0.33M to approximately 0.82M salt, hybridization temperature 40° C. to 48° C. below $T_m$. $T_m$ of duplex nucleic acids is calculated by standard methods well-known in the art (see, e.g., Maniatis, T., et al., Molecular Cloning: A Laboratory Manual., Cold Spring Harbor Laboratory Press: New York (1982); Casey, J., et al., Nucleic Acids Research 4:1539-1552 (1977); Bodkin, D. K., et al., Journal of Virological Methods 10(1): 45-52 (1985); Wallace, R. B., et al., Nucleic Acids Research 9(4):879-894 (1981)). Algorithm prediction tools to estimate $T_m$ are also widely available. High stringency conditions for hybridization typically refer to conditions under which a polynucleotide complementary to a target sequence predominantly hybridizes with the target sequence, and substantially does not hybridize to non-target sequences. Typically, hybridization conditions are of moderate stringency, preferably high stringency.

As used herein, a "stem element" or "stem structure" refers to a polynucleotide comprising two strands that are known or predicted to form a double-stranded region (the "stem element"). A "stem-loop element" or "stem-loop structure" refers to a stem structure wherein 3-end sequences of one strand are covalently bonded to 5'-end sequences of the second strand by a nucleotide sequence of typically single-stranded nucleotides ("a stem-loop element nucleotide sequence"). In some embodiments, the loop element comprises a loop element nucleotide sequence of between about 3 and about 20 nucleotides in length, preferably between about 4 and about 10 nucleotides in length. In preferred embodiments, a loop element nucleotide sequence is a single-stranded nucleotide sequence of unpaired nucleic acid bases that do not interact through hydrogen bond formation to create a stem element within the loop element nucleotide sequence. The term "hairpin element" is also used herein to refer to stem-loop structures. Such structures are well known in the art. The base pairing may be exact; however, as is known in the art, a stem element does not require exact base pairing. Thus, the stem element may include one or more base mismatches or non-paired bases.

A "linker element nucleotide sequence" and "linker nucleotide sequence" are used interchangeable herein and refer to a single-stranded sequence of one or more nucleotides covalently attached to a first polynucleotide sequence (e.g., in a 5' to 3' direction, 5'-linker nucleotide sequence-first polynucleotide-3',5'-first polynucleotide-linker nucleotide sequence-3',5'-linker nucleotide sequence-first polynucleotide-linker nucleotide sequence-3') and typically refer to a single-stranded nucleic acid sequence connecting a first polynucleotide sequence with a second polynucleotide sequence. In some embodiments, the linker element nucleotide sequence can be a single-stranded nucleotide sequence of unpaired nucleic acid bases that do not interact through hydrogen bond formation to create a stem element within the linker element nucleotide sequence. In additional embodiments, a linker element nucleotide sequence can be between about 1 and about 50 nucleotides in length, preferably between about 2 and about 15 nucleotides in length.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms also refer to an amino acid polymer that has been modified through, for example, acetylation, disulfide bond formation, glycosylation, lipidation, phosphorylation, pegylation, biotinylation, cross-linking, and/or conjugation (e.g., with a labeling component or ligand). Polypeptide sequences are displayed herein in the conventional N-terminal to C-terminal orientation, unless otherwise indicated.

Polypeptides and polynucleotides can be made using routine techniques in the field of molecular biology (see, e.g., standard texts discussed above). Furthermore, essentially any polypeptide or polynucleotide is available from commercial sources.

The terms "fusion protein" and "chimeric protein," as used herein, refer to a single protein created by joining two or more proteins, protein domains, or protein fragments that do not naturally occur together in a single protein. For example, a fusion protein can contain a first domain from a Cas9 protein and a second domain a Csy4 protein. The modification to include such domains in fusion protein may confer additional activity on the modified site-directed polypeptides. Such activities can include nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity) that modifies a polypeptide associated with nucleic acid target sequence (e.g., a histone). A fusion protein can also comprise epitope tags (e.g., histidine tags, FLAG® (Sigma Aldrich, St. Louis, Mo.) tags, Myc tags), reporter protein sequences (e.g., glutathione-S-transferase, beta-galactosidase, luciferase, green fluorescent protein, cyan fluorescent protein, yellow fluorescent protein), and/or nucleic acid binding domains (e.g., a DNA binding domain, an RNA binding domain). A fusion protein can also comprise activator domains (e.g., heat shock transcription factors, NFKB activators) or repressor domains (e.g., a KRAB domain). As described by Lupo, A., et al., Current Genomics 14(4): 268-278 (2013), the KRAB domain is a potent transcriptional repression module and is located in the amino-terminal sequence of most C2H2 zinc finger proteins (see, e.g., Margolin, J., et al., Proceedings of the National Academy of Sciences of the United States of America 91:4509-4513 (1994); Witzgall, R., et al., Proceedings of the National Academy of Sciences of the United States of America 91:4514-4518 (1994)). The KRAB domain typically binds to co-repressor proteins and/or transcription factors via protein-protein interactions, causing transcriptional repression of genes to which KRAB zinc finger proteins (KRAB-ZFPs) bind (see, e.g., Friedman J. R., et al., Genes & Development 10:2067-2678 (1996)). In some embodiments, linker nucleic acid sequences are used to join the two or more proteins, protein domains, or protein fragments.

A "moiety," as used herein, refers to a portion of a molecule. A moiety can be a functional group or describe a portion of a molecule with multiple functional groups (e.g., that share common structural aspects). The terms "moiety" and "functional group" are typically used interchangeably; however, a "functional group" can more specifically refer to a portion of a molecule that comprises some common chemical behavior. "Moiety" is often used as a structural description. In some embodiments, a 5' terminus, a 3' terminus, or a 5' terminus and a 3' terminus (e.g., a non-native 5' terminus and/or a non-native 3' terminus in a first stem element) can comprise one or more moieties.

The term "affinity tag," as used herein, typically refers to one or more moieties that increases the binding affinity of a dfs-PN to a Cas protein, for example, to facilitate formation of a dfs-NATNA/Cas9 protein complex. In a preferred embodiment, the dfs-PN that comprises a spacer sequence further comprises one or more moieties. In some embodiments, an affinity tag can be used to increase the binding affinity of any dfs-PN of a dfs-NATNA to a Cas protein (e.g., a Cas9 protein). Some embodiments of the present invention use an "affinity sequence," which is a polynucleotide sequence comprising one or more affinity tags. In some embodiments of the present invention, the dfs-PN comprising a spacer sequence further comprises an affinity sequence located 5' to the nucleic acid target binding sequence. In other embodiments, the dfs-PN comprising a spacer sequence further comprises an affinity sequence located 3' to the nucleic acid target binding sequence. In further embodiments, the dfs-PN comprising a spacer sequence further comprises an affinity sequence located 5' and 3' to the nucleic acid target binding sequence. Some embodiments of the present invention introduce one or more affinity tags to the N-terminal of a Cas protein sequence (e.g., a Cas9 protein sequence), to the C-terminal of a Cas protein sequence, to a position located between the N-terminal and C-terminal of a Cas protein sequence, or to combinations thereof. In some embodiments of the invention, the Cas-polypeptide is modified with an affinity tag or an affinity sequence. In some embodiments of the present invention, one or more dfs-PNs of a dfs-NATNA comprises an affinity sequence wherein the affinity sequence is located at the 5'-end sequences, at the 3'-end sequences, at both the 5'-end and 3' end sequences, or at a position between the 5'-end sequences and 3'-end sequences of a dfs-PN, as well as combinations thereof. A wide variety of affinity tags are disclosed in U.S. Published Patent Application No. 2014-0315985, published 23 Oct. 2014.

As used herein, a "cross-link" is a bond that links one polymer chain (e.g., a polynucleotide or polypeptide) to another. Such bonds can be covalent bonds or ionic bonds. In some embodiments, one polynucleotide can be bound to another polynucleotide by cross linking the polynucleotides. In other embodiments, a polynucleotide can be cross linked to a polypeptide. In additional embodiments, a polypeptide can be cross linked to a polypeptide.

The term "cross-linking moiety," as used herein, typically refers to a moiety suitable to provide cross linking between a dfs2-PN and a cognate Cas protein (e.g., a Cas9 protein), a dfs1-PN and a cognate Cas protein (e.g., a Cas9 protein), or both a dfs2-PN and a dfs1-PN to a cognate Cas protein (e.g., a Cas9 protein). A cross-linking moiety is another example of an affinity tag.

The terms "ligand" and "ligand-binding moiety," as used herein, refer to moieties that facilitate the binding of a dfs2-PN and a cognate Cas protein (e.g., a Cas9 protein), a dfs1-PN and a cognate Cas protein (e.g., a Cas9 protein), or both a dfs2-PN and a dfs1-PN to a cognate Cas protein (e.g., a Cas9 protein). Ligands and ligand-binding moieties are paired affinity tags.

As used herein, a "host cell" generally refers to a biological cell. A cell is the basic structural, functional and/or biological unit of an organism. A cell can originate from any organism having one or more cells. Examples of host cells include, but are not limited to: a prokaryotic cell, eukaryotic cell, a bacterial cell, an archaeal cell, a cell of a single-cell eukaryotic organism, a protozoal cell, a cell from a plant (e.g., cells from plant crops (such as soy, tomatoes, sugar beets, pumpkin, hay, cannabis, tobacco, plantains, yams, sweet potatoes, cassava, potatoes, wheat, sorghum, soybean, rice, corn, maize, oil-producing Brassica (e.g., oil-producing rapeseed and canola), cotton, sugar cane, sunflower, millet, and alfalfa), fruits, vegetables, grains, seeds, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. agardh*, and the like), seaweeds (e.g., kelp), a fungal cell (e.g., a yeast cell or a cell from a mushroom), an animal cell, a cell from an invertebrate animal (e.g., fruit fly, cnidarian, echinoderm, nematode, and the like), a cell from a vertebrate animal (e.g., fish, amphibian, reptile, bird, or mammal), a cell from a mammal (e.g., a pig, a cow, a goat, a sheep, a rodent, a rat, a mouse, a non-human primate, a human, and the like). Furthermore, a cell can be a stem cell or a progenitor cell.

As used herein, "stem cell" refers to a cell that has the capacity for self-renewal, i.e., the ability to go through numerous cycles of cell division while maintaining the undifferentiated state. Stem cells can be totipotent, pluripotent, multipotent, oligopotent, or unipotent. Stem cells can be embryonic, fetal, amniotic, adult, or induced pluripotent stem cells.

As used herein, "induced pluripotent stem cells" refers to a type of pluripotent stem cell that is artificially derived from a non-pluripotent cell, typically an adult somatic cell, by inducing expression of specific genes.

"Plant," as used herein, refers to whole plants, plant organs, plant tissues, germplasm, seeds, plant cells, and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. "Plant organ" refers to plant tissue or a group of tissues that constitute a morphologically and functionally distinct part of a plant.

"Subject," as used herein, refers to any member of the phylum Chordata, including, without limitation, humans and other primates, including non-human primates such as rhesus macaques, chimpanzees and other monkey and ape species; farm animals, such as cattle, sheep, pigs, goats and horses; domestic mammals, such as dogs and cats; laboratory animals, including rabbits, mice, rats and guinea pigs; birds, including domestic, wild, and game birds, such as chickens, turkeys and other gallinaceous birds, ducks, and geese; and the like. The term does not denote a particular age or gender. Thus, the term includes adult, young, and newborn individuals as well as male and female. In some embodiments, a host cell is derived from a subject (e.g., stem cells, progenitor cells, or tissue-specific cells). In some embodiments, the subject is a non-human subject.

As used herein, "transgenic organism" refers to an organism whose genome is genetically modified. The term includes the progeny (any generation) of a transgenic organism, provided that the progeny has the genetic modification.

As used herein, "isolated" can refer to a nucleic acid or polypeptide that, by human intervention, exists apart from its native environment and is therefore not a product of nature. An isolated nucleic acid or polypeptide can exist in a purified form and/or can exist in a non-native environment such as, for example, in a recombinant cell.

Aspects of the present invention relate to at least one engineered break in the nucleic acid backbone of a CRISPR-Cas-associated guide polynucleotide(s) (e.g., a Class 2 Type II CRISPR-Cas9-associated guide polynucleotide(s)). The engineered break results in one or more non-native 5' termini and one or more non-native 3' termini (non-native relative to the CRISPR-Cas-associated guide polynucleotide(s)). In one aspect, the present invention relates to a Class 2 CRISPR-Cas-associated guide polynucleotide composition comprising one or more non-native 5' termini and one or more non-native 3' termini. In a preferred aspect, the composition is capable of forming a complex with a cognate Cas protein (e.g., a Cas9 protein), and the complex preferentially binds a nucleic acid target sequence in a polynucleotide relative to a polynucleotide that does not comprise the nucleic acid target sequence.

In a first aspect, the present invention relates to Class 2 Type II CRISPR-Cas9-associated discontinuous first-stem nucleic-acid targeting nucleic acid (dfs-NATNA) compositions, which are exemplified herein. A dfs-NATNA composition comprises at least one engineered break resulting in one or more non-native 5' termini and one or more non-native 3' termini, preferably in the first stem element.

In some embodiments of the first aspect of the present invention, a first stem-loop element comprises the first stem element, and one strand of the first stem element comprises one or more non-native 5' termini and one or more non-native 3' termini. Typically, the first stem element comprises a lower stem element 3' of the nucleic acid targeting sequence and 5' of the nexus nucleotide sequence. The lower stem element is adjacent a bulge element. The bugle element is adjacent an upper stem element, and the upper stem element is adjacent a loop element (see, e.g., FIG. 3A and Table 1).

In one embodiment of the first aspect of the present invention, the lower stem element further comprises a lower stem element nucleotide sequence I and a lower stem element nucleotide sequence II. The lower stem element nucleotide sequence I or the lower stem element nucleotide sequence II comprises at least a pair of hydrogen-bonded nucleotides at a 5' terminus of the dfs1-PN and at least a pair of hydrogen-bonded nucleotides at a 3' terminus of the dfs2-PN.

In a further embodiment of the first aspect of the present invention, a dfs-NATNA composition comprises two polynucleotides: a first Class 2 Type II CRISPR-Cas9-associated discontinuous first-stem single-strand polynucleotide (dfs1-PN) comprising, in a 5' to 3' direction, a first stem element nucleotide sequence I, a nexus nucleotide sequence, and a 3' hairpin element; and a second Class 2 Type II CRISPR-Cas9-associated discontinuous first-stem single-strand polynucleotide (dfs2-PN) comprising, in a 5' to 3' direction, a nucleic acid target binding sequence and a first stem element nucleotide sequence II. The first stem element nucleotide sequence I and the first stem element nucleotide sequence II form a first stem-loop element by base-pair hydrogen bonding between the first stem element nucleotide sequence I and the first stem element nucleotide sequence II. In preferred embodiments, the first stem-loop element comprises a lower stem element 3' of the nucleic acid targeting sequence and 5' of the nexus nucleotide sequence, the lower stem element adjacent a bulge element, the bugle element adjacent an upper stem element, and the upper stem element adjacent a loop element. In some embodiments, the lower stem element comprises at least a pair of hydrogen-bonded nucleotides flanking the 5' terminus of the dfs1-PN and the 3' terminus of the dfs2-PN, the upper stem element comprises at least a pair of hydrogen-bonded nucleotides flanking the 5' terminus of the dfs1-PN and the 3' terminus of the dfs2-PN, or at least a pair of hydrogen-bonded nucleotides flanking the 5' terminus of the dfs1-PN and the 3' terminus of the dfs2-PN and the upper stem element comprises at least a pair of hydrogen-bonded nucleotides flanking the 5' terminus of the dfs1-PN and the 3' terminus of the dfs2-PN.

Types of hydrogen bonds are discussed above. Embodiments of the present invention include, but are not limited to, the following types of hydrogen bonds in pairs of hydrogen-bonded nucleotides: W-C hydrogen bonding, reverse W-C hydrogen bonding, Hoogsteen hydrogen bonding, reverse Hoogsteen hydrogen bonding, wobble hydrogen bonding, reverse wobble hydrogen bonding, or combinations thereof. In some embodiments, the pair of hydrogen-bonded nucleotides at the 5' terminus of the dfs1-PN is a pair of Watson-Crick-hydrogen-bonded nucleotides, and the pair of hydrogen-bonded nucleotides at the 3' terminus of the dfs2-PN is a pair of Watson-Crick-hydrogen-bonded nucleotides or wobble-hydrogen-bonded nucleotides. In additional embodiments, the pair of hydrogen-bonded nucleotides at the 3' terminus of the dfs2-PN is a pair of Watson-Crick-hydrogen-bonded nucleotides.

One method to determine the presence of hydrogen bonds in pairs of hydrogen-bonded nucleotides is prediction of the secondary structure of each polynucleotide (see, e.g., Ran, F. A., et al., Nature 520(7546):186-191 (2015); Zuker, M., Mfold web server for nucleic acid folding and hybridization prediction, Nucleic Acids Research 31:3406-3415 (2003)).

Methods are known to those of ordinary skill in the art to determine the presence of hydrogen bonds in pairs of hydrogen-bonded nucleotides. For example, experimental techniques include, but not limited to, X-ray crystallography, Nuclear Magnetic Resonance (NMR) spectroscopy, Cryo-electron microscopy (Cryo-EM), chemical/enzymatic probing, thermal denaturation (melting studies), and Mass Spectrometry. Predictive techniques can be employed, such as computational structure prediction for each dfs-NATNA polynucleotide (see, e.g., Ran, F. A., et al., Nature 520 (7546):186-191 (2015); Zuker, M., Mfold web server for nucleic acid folding and hybridization prediction, Nucleic Acids Research 31:3406-3415 (2003); "RNAfold web server" (rna.tbi.univie.ac.at/cgi-bin/RNAfold.cgi); Gruber A. R., et al., The Vienna RNA Wetsuit, Nucleic Acids Research 36(supplement 2):W70-W74 (2008); Lorenz, R., et "ViennaRNA Package 2.0," Algorithms for Molecular Biology 16:26 (2011). A preferred method to evaluate RNA secondary structure is to use the combined experimental and computational SHAPE method (Low J. T., et al., Methods 52(2):150-158 (2010).

An empirical method to determine whether there is secondary structure (created by base-pair hydrogen bonding) is analysis on non-denaturing gels (see, e.g., McGookin, R., Methods Molecular Biology 2:93-100 (1985)). In this method, dfs-NATNA polynucleotides are combined in equal molar concentrations in an annealing or hybridization buffer (e.g., 1.25 mM HEPES, 0.625 mM $MgCl_2$, 9.375 mM KCl at pH7.5; or 20 mM Tris-HCl pH 7.5, 100 mM KCl, 5 mM $MgCl_2$), incubated above the melting temperature of the dfs-NATNA polynucleotides and allowed to equilibrate at room temperature. This re-annealed mixture of polynucleotides is a "combined" dfs-NATNA. The same steps are applied to the individual dfs-NATNA polynucleotides. In separate reactions the same equal molar concentrations of each individual dfs-NATNA, as is used for the combined sample polynucleotides, are processed. After re-annealing the individual dfs-NATNAs are combined ("separate" dfs-NATNAs).The combined and separate samples are resolved side-by-side on non-denaturing gels. The banding patterns of the combined and separate samples are compared. Formation of secondary structure is indicated by differences in the banding patterns between the combined and separate samples.

In some embodiments of the first aspect of the present invention, a dfs1-PN comprises first and/or second adjunct polynucleotides. A dfs1-PN can further comprise, in a 5' to 3' direction, the nexus stem element nucleotide sequence, a nexus 3' linker nucleotide sequence, a 3' hairpin-1 stem element nucleotide sequence I, and a first adjunct polynucleotide comprises a 3' hairpin-1 stem element nucleotide sequence II. The 3' hairpin-1 stem element nucleotide sequence I and the 3' hairpin-1 stem element nucleotide sequence II are capable of forming a 3' hairpin-1 stem element by base-pair hydrogen bonding between the 3' hairpin-1 stem element nucleotide sequence I and the 3' hairpin-1 stem element nucleotide sequence II. In some embodiments, the first adjunct polynucleotide comprises, in a 5' to 3' direction, a 3' hairpin-1 loop element nucleotide sequence and a hairpin-1 stem element nucleotide sequence II, wherein 5'terminus of the 3' hairpin-1 loop element nucleotide sequence is covalently bonded to the 3' terminus of the 3' hairpin-1 stem element nucleotide sequence I, thus forming a 3' hairpin-1 element.

In yet further embodiments, the first adjunct polynucleotide comprises, in a 5' to 3' direction, a 3' hairpin-1 stem element nucleotide sequence II and a 3' hairpin-2 stem element nucleotide sequence I, and a second adjunct polynucleotide comprises, in a 5' to 3' direction, a 3' hairpin-2 stem element nucleotide sequence II. The 3' hairpin-2 stem element nucleotide sequence I and the 3' hairpin-2 stem element nucleotide sequence II are capable of forming a 3' hairpin-2 element by base-pair hydrogen bonding between the 3' hairpin-2 stem element nucleotide sequence I and the 3' hairpin-2 stem element nucleotide sequence II. In some embodiments, the second adjunct polynucleotide comprises, in a 5' to 3' direction, a 3' hairpin-2 loop element nucleotide sequence and the 3' hairpin-2 stem element nucleotide sequence II, wherein the 5' terminus of the 3' hairpin-2 loop element nucleotide sequence is covalently bonded to the 3' terminus of the 3' hairpin-2 stem element nucleotide sequence I, thus forming a 3' hairpin-2 element.

Figure 3A:
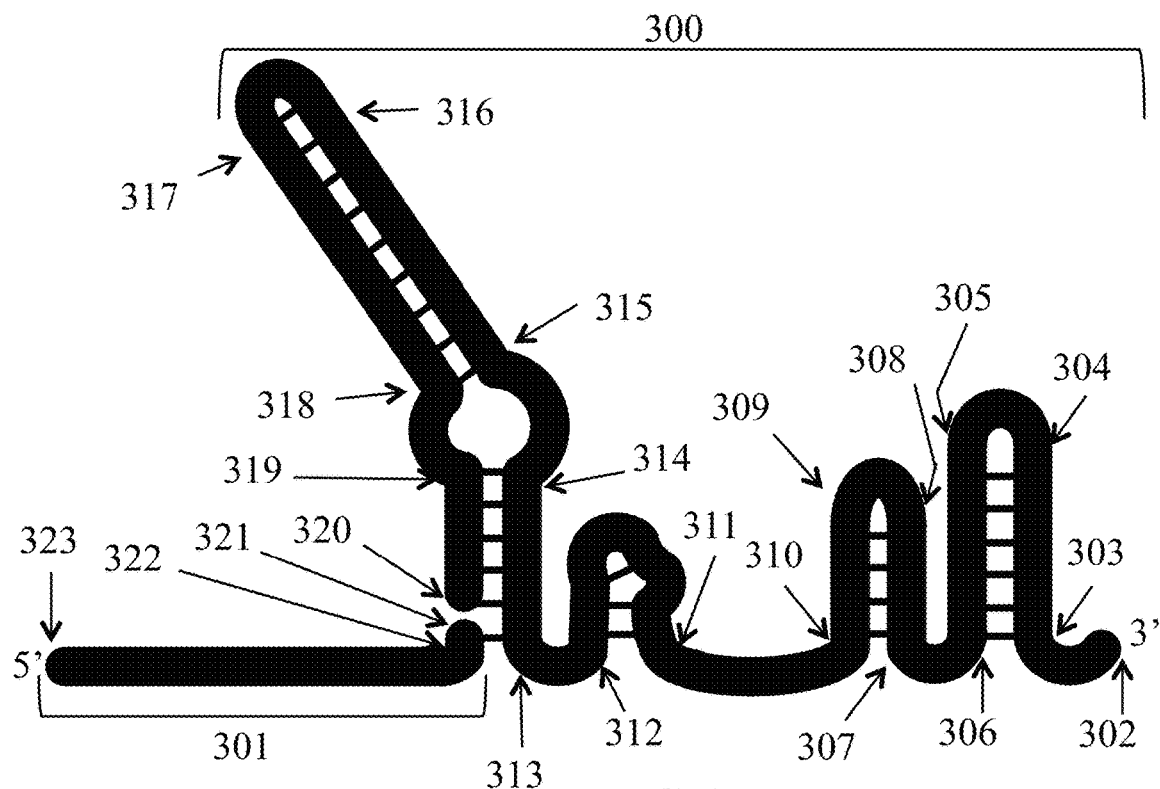
FIG. 3A, FIG. 3B, FIG. 3C, FIG. 3D, FIG. 3E, FIG. 3F, FIG. 3G, and FIG. 3H illustrate embodiments of Class 2 Type II CRISPR-Cas9-associated discontinuous first-stem nucleic-acid targeting nucleic acids of the present invention.

FIG. 3A presents an illustration of a dfs-NATNA having two components. FIG. 3A, 300 illustrates an example of a first Class 2 Type II CRISPR-Cas9-associated discontinuous first-stem single-strand polynucleotide (dfs1-PN) comprising, in a 5' to 3' direction, a non-native 5' terminus, a nexus nucleotide sequence, and a 3' terminus. FIG. 3A, 301 illustrates an example of a second Class 2 Type II CRISPR-Cas9-associated discontinuous first-stem single-strand polynucleotide (dfs2-PN) comprising, in a 5' to 3' direction, a 5' terminus, a nucleic acid target binding sequence, and a non-native 3' terminus. Table 1 presents a series of indicators applied consistently in FIG. 3A, FIG. 3B, FIG. 3C, FIG. 3D, FIG. 3E, FIG. 3F, FIG. 3G, and FIG. 3H. In Table 1, "–" is the equivalent of the term "comprising."

TABLE 1

Numerical Indicators Used to Illustrate Regions of Exemplary dfs-PN Nucleotide Sequences

Figure 3B:
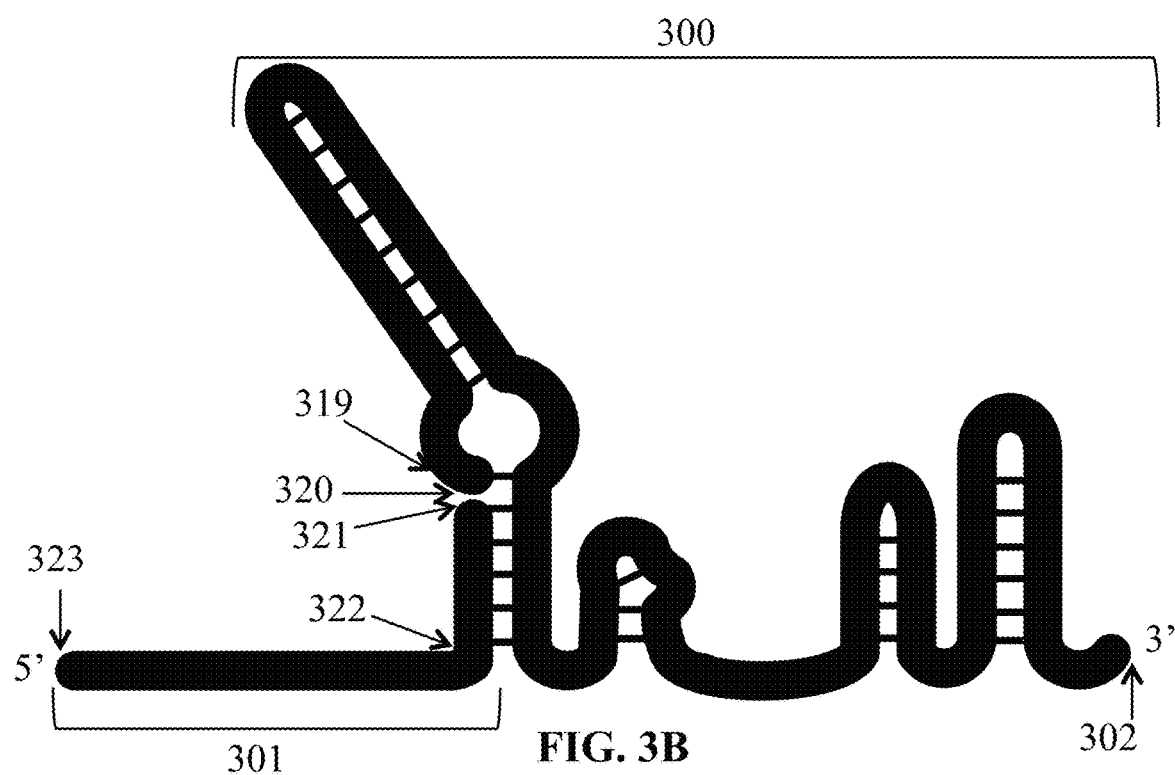
Figure 3C:
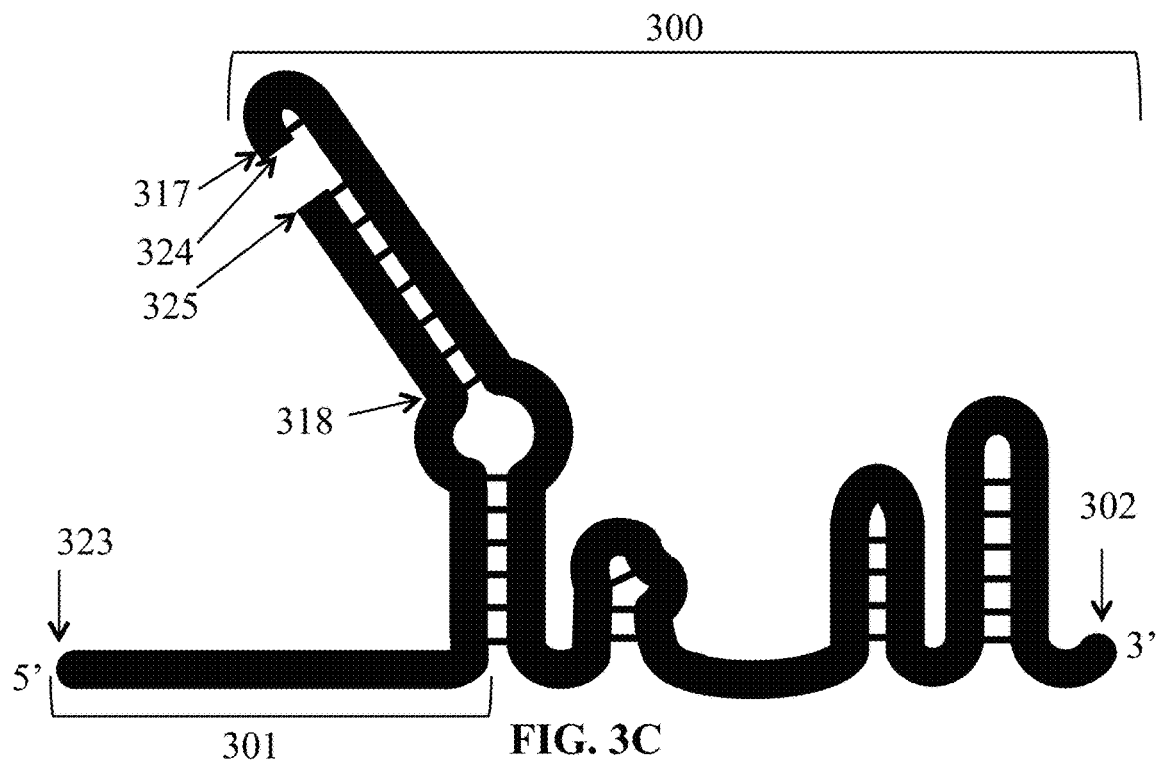
Figure 3D:
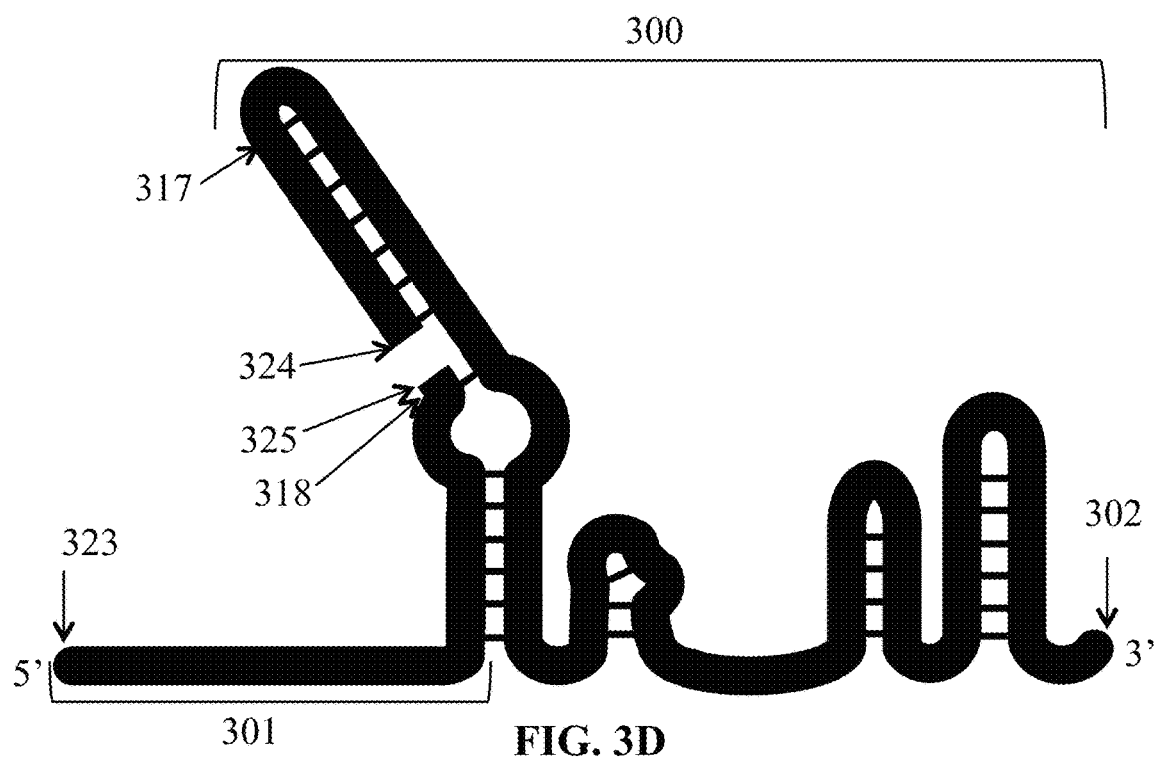
Figure 3E:
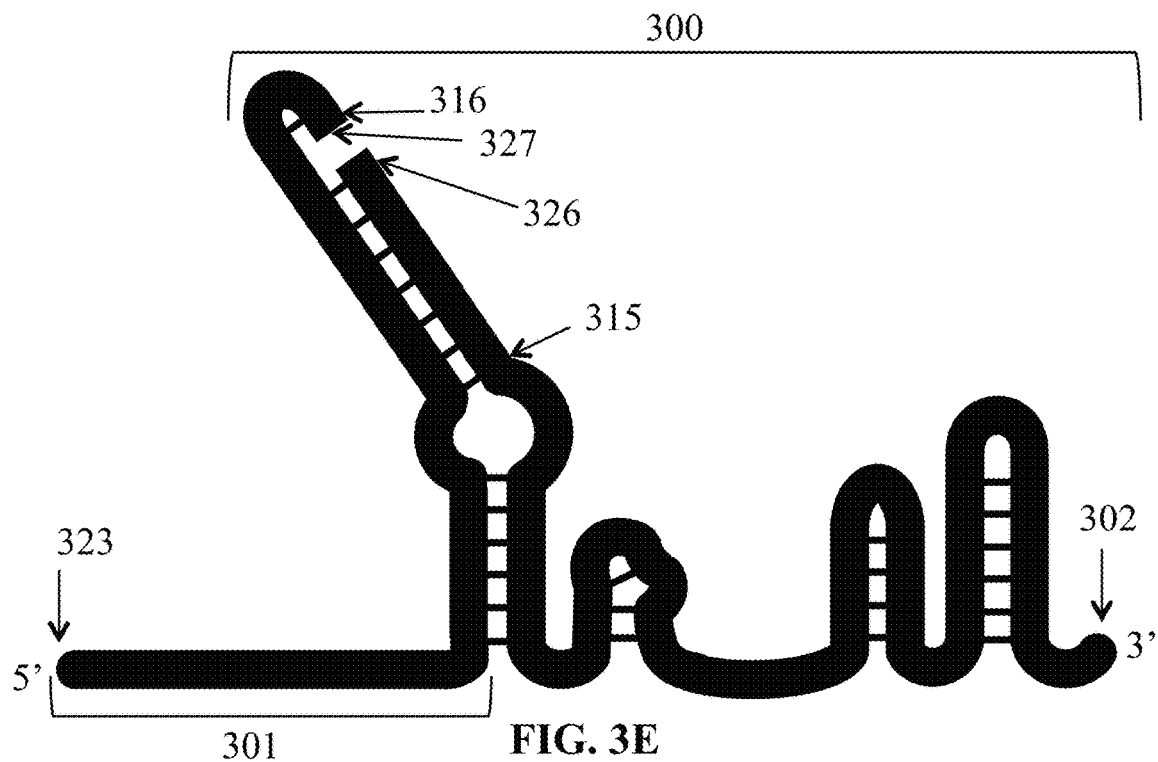
Figure 3F:
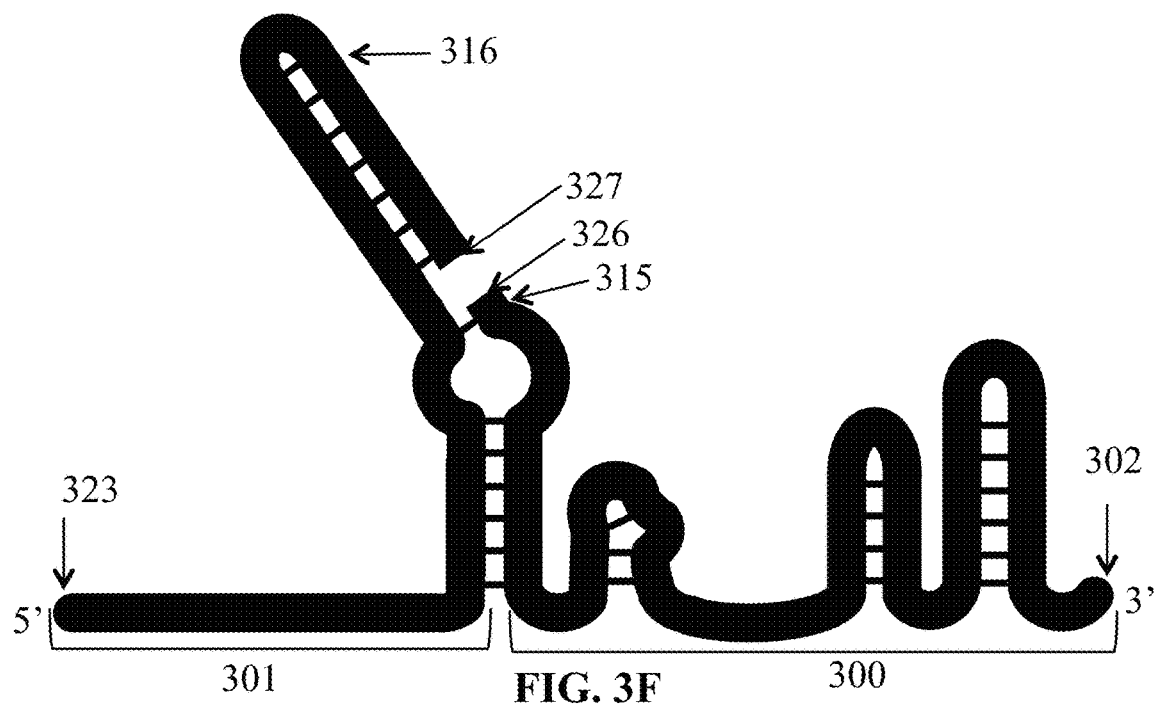
Figure 3G:
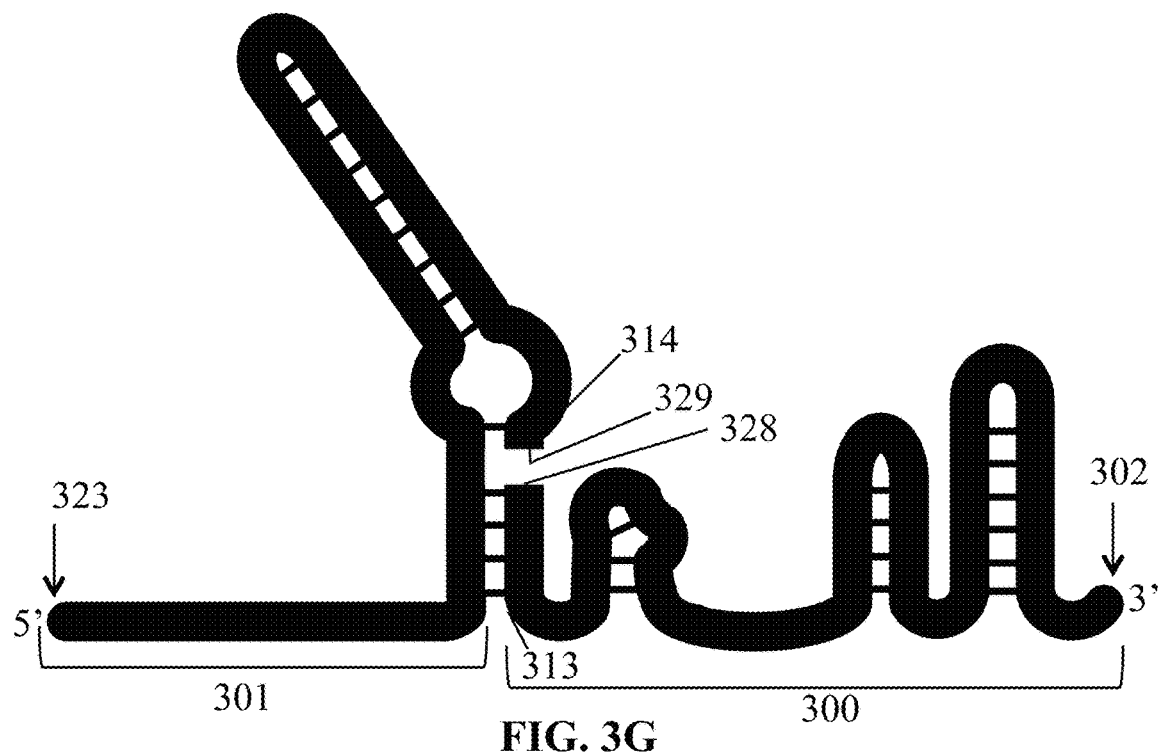
Figure 3H:
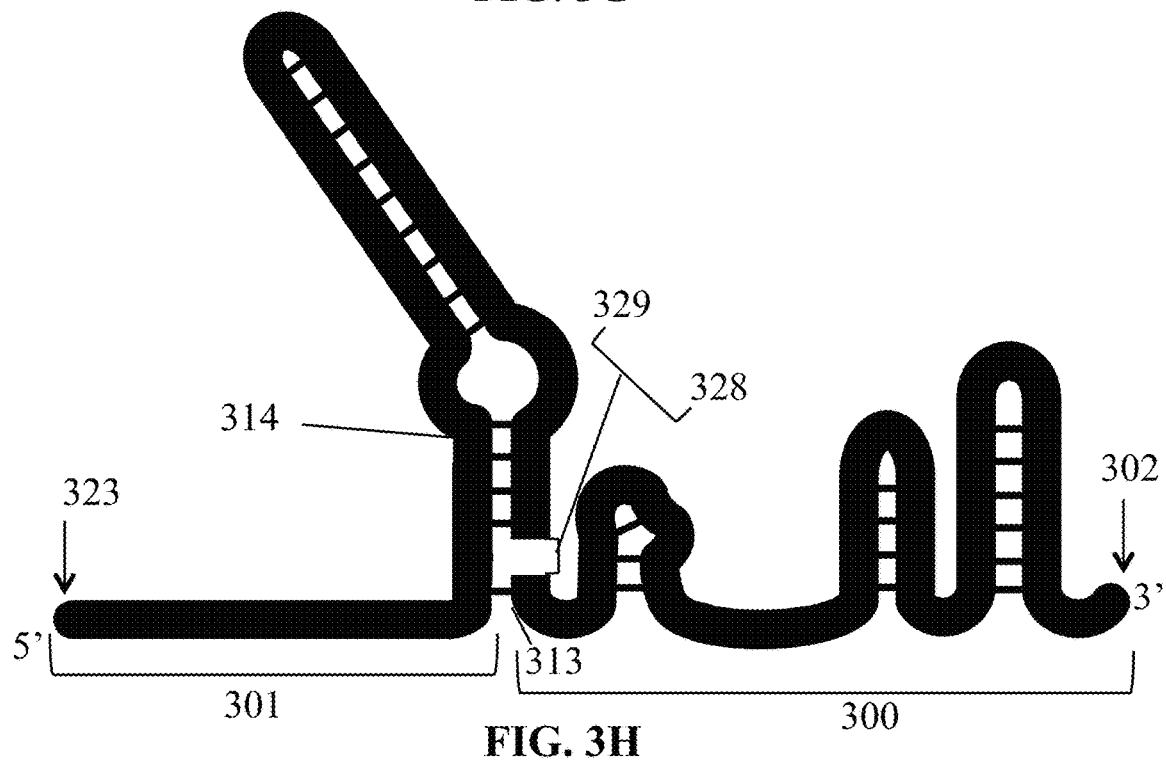

| Indicator | Description |
|---|---|
| | FIG. 3A to FIG. 3H (general) |
| 300 | a dfs1-PN |
| 301 | a dfs2-PN |
| 302 | a 3' terminus of the dfs1-PN |
| 302-303 | a 3' terminal nucleotide sequence |
| 303-304 | a second adjunct polynucleotide - a 3' hairpin-2 stem element nucleotide sequence II |
| 304-305 | a second adjunct polynucleotide - a 3' hairpin-2 loop element nucleotide sequence |
| 305-306 | a first adjunct polynucleotide - a 3' hairpin-2 stem element nucleotide sequence I |
| 306-307 | a first adjunct polynucleotide - a 3'-hairpin linker element nucleotide sequence |
| 307-308 | a first adjunct polynucleotide - a 3' hairpin-1 stem element nucleotide sequence II |
| 308-309 | a first adjunct polynucleotide - a 3' hairpin-1 loop element nucleotide sequence |
| 303-306 | a 3' hairpin-2 element |
| 310-307 | a 3' hairpin-1 element |
| 309-310 | a nexus nucleotide sequence - a 3' hairpin-1 stem element nucleotide sequence I |
| 310-311 | a nexus nucleotide sequence - a nexus 3' linker nucleotide sequence |
| 311-312 | a nexus element - a nexus nucleotide sequence - a nexus element nucleotide sequence |
| 312-313 | a nexus nucleotide sequence - a nexus 5' linker nucleotide sequence |
| 313-314 | a first stem element nucleotide sequence I - a lower stem element nucleotide sequence I |
| 314-315 | a first stem element nucleotide sequence I - a bulge element nucleotide sequence I |
| 315-316 | a first stem element nucleotide sequence I - an upper stem element nucleotide sequence I |
| 316-317 | a first stem-loop element nucleotide sequence |
| 317-318 | a first stem element nucleotide sequence II - an upper stem element nucleotide sequence II |
| 318-319 | a first stem element nucleotide sequence II - a bulge element nucleotide sequence II |
| 319-322 | a first stem element nucleotide sequence II - a lower stem element nucleotide sequence II |
| 318-317/ 315-316 | an upper stem element |
| 318-319/ 314-315 | a bulge element |
| 319-322/ 313-314 | a lower stem element |
| 322-323 | a nucleic acid target binding sequence |
| 323 | a 5' terminus of the dfs2-PN |
| | FIG. 3A and 3B (figure-specific) |
| 319-320 | a first stem element nucleotide sequence II - a lower stem element nucleotide sequence II - a fragment nucleotide sequence 1 |
| 320 | a 5' terminus of the dfs1-PN (a non-native terminus) |
| 321 | a 3' terminus of the dfs2-PN (a non-native terminus) |
| 321-322 | a first stem element nucleotide sequence II - a lower stem element nucleotide sequence II - a fragment nucleotide sequence 2 |
| | FIG. 3C and FIG. 3D (figure-specific) |
| 317-324 | a first stem element nucleotide sequence II - an upper stem element nucleotide sequence II - a fragment nucleotide sequence 1 |
| 324 | a 5' terminus of the dfs1-PN (a non-native terminus) |
| 325 | a 3' terminus of the dfs2-PN (a non-native terminus) |
| 325-318 | a first stem element nucleotide sequence II - an upper stem element nucleotide sequence II - a fragment nucleotide sequence 2 |
| | FIG. 3E and FIG. 3F (figure-specific) |
| 327-316 | a first stem element nucleotide sequence I - an upper stem element nucleotide sequence I - fragment nucleotide sequence 2 |
| 327 | a 3' terminus of the dfs2-PN (a non-native terminus) |
| 326 | a 5' terminus of the dfs1-PN (a non-native terminus) |
| 326-315 | a first stem element nucleotide sequence I - an upper stem element nucleotide sequence I - a fragment nucleotide sequence 1 |
| | FIG. 3G and FIG. 3H (figure-specific) |
| 329-314 | a first stem element nucleotide sequence I - a lower stem element nucleotide sequence I - a fragment nucleotide sequence 2 |
| 329 | a 3' terminus of the dfs2-PN (a non-native terminus) |
| 328 | a 5' terminus of the dfs1-PN (a non-native terminus) |

TABLE 1-continued

Numerical Indicators Used to Illustrate Regions of Exemplary dfs-PN Nucleotide Sequences

| Indicator | Description |
|---|---|
| 313-328 | a first stem element nucleotide sequence I - a lower stem element nucleotide sequence I - a fragment nucleotide sequence 1 |

A typical Class 2 Type II single guide polynucleotide comprises a 5'-S-LII-BII-UII-L-UI-BI-LI- . . . 3' polynucleotide; however, typical Class 2 Type II single guide polynucleotide does not comprise non-native termini.

Example 1 describes production of polynucleotide components of engineered Class 2 Type II CRISPR-Cas9-associated discontinuous first-stem nucleic-acid targeting nucleic acid ("dfs-NATNA") compositions, for example, as illustrated in FIG. 3A and FIG. 3B. Components of the dfs-NATNA compositions were assembled by PCR using 3' overlapping primers containing DNA sequences corresponding to each dfs-NATNA component. In vitro transcription of the DNA templates was carried out using a T7 promoter and a T7 RNA polymerase.

Figure 4A:
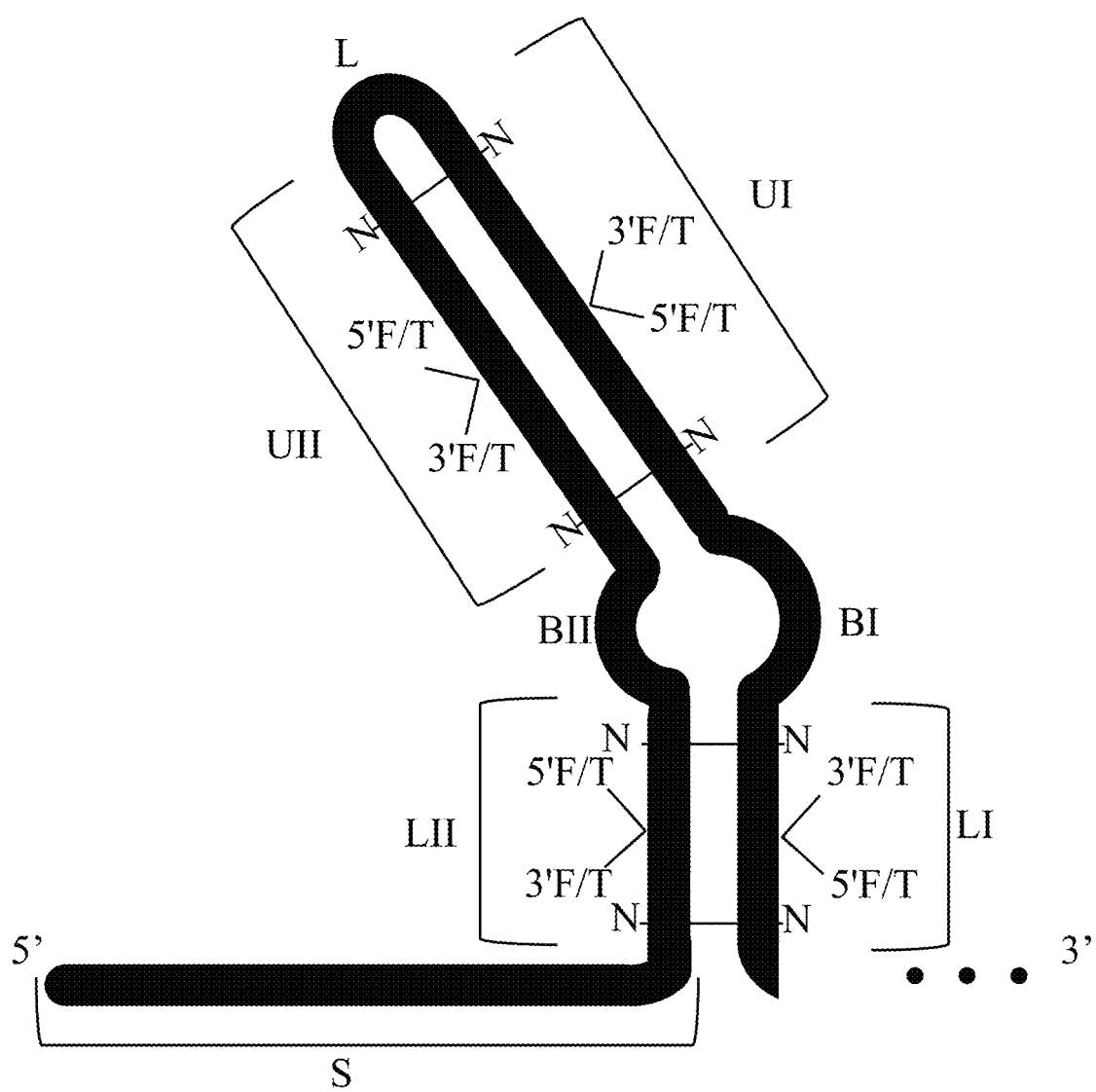
FIG. 4A, FIG. 4B, FIG. 4C, and FIG. 4D illustrate embodiments of the Class 2 Type II CRISPR-Cas9-associated discontinuous first-stem nucleic-acid targeting nucleic acids of the present invention.

FIG. 4A illustrates exemplary breakpoints for engineering dfs-NATNAs for some embodiments of the present invention. The indicators used in FIG. 4A are described in Table 2.

TABLE 2

Indicators Used to Illustrate Exemplary dfs-PNs

| Indicator | Description |
|---|---|
| 5' | 5' terminus of dfs2-PN |
| S | a nucleic acid target binding sequence |
| N | a nucleotide |
| N—N | a pair of hydrogen-bonded nucleotides |
| 3'F/T | a 3' terminus of dfs2-PN (non-native terminus) |
| 5'F/T | a 5' terminus of dfs1-PN (non-native terminus) |
| > | an exemplary engineered break in the nucleic acid backbone resulting in at least one non-native 5' terminus and one non-native 3' terminus |
| LII | a first stem element nucleotide sequence II |
| BII | a bulge element nucleotide sequence II |
| UII | an upper stem element nucleotide sequence I |
| L | a first stem-loop element nucleotide sequence |
| UI | an upper stem element nucleotide sequence I |
| BI | a bulge element nucleotide sequence I |
| LI | a first stem element nucleotide sequence I |
| . . . 3' | additional nucleotide sequences of dfs1-PN |

In some embodiments, the lower stem nucleotide sequence I and the lower stem element nucleotide sequence II are each between 2 and 10 nucleotides in length, the bulge element nucleotide sequence I and the bulge element nucleotide sequence II are each between 1 and 10 nucleotides in length, and the upper stem nucleotide sequence I and the upper stem element nucleotide sequence II are each between 2 and 22 nucleotides in length. Examples of these sequence lengths based on natural guide RNA sequences include the following: *S. pyogenes*, the lower stem nucleotide sequence I and the lower stem element nucleotide sequence II are each 6 nucleotides in length, the bulge element nucleotide sequence I is 4 nucleotides in length, the bulge element nucleotide sequence II is 2 nucleotides in length, and the upper stem element nucleotide sequence I and the upper stem element nucleotide sequence II are each between 4-20 nucleotides in length; *S. aureus*, the lower stem nucleotide sequence I and the lower stem element nucleotide sequence II are each 9 nucleotides in length, the bulge element nucleotide sequence I is 3 nucleotides in length, the bulge element nucleotide sequence II is 1 nucleotide in length, and the upper stem element nucleotide sequence I and the upper stem element nucleotide sequence II are each between 3-20 nucleotides in length.

Additional embodiments of the invention can include dfs-NATNAs comprising an engineered break in the nucleic acid backbone of bulge element nucleotide sequence I or II resulting in at least one 5' non-native terminus and one 3' non-native terminus.

Table 3 presents exemplary arrangements of elements within dfs-NATNAs comprising two polynucleotides: dfs1-PNs and dfs2-PNs. The elements are given with reference to Table 2. In Table 3, the indicator "N-3'F/T" refers to a fragment nucleotide sequence 2 comprising, in a 5' to 3' direction, at least one nucleotide and the 3' terminus of the dfs2-PN, and the indicator "5'F/T-N" refers to a fragment nucleotide sequence 1 comprising, in a 5' to 3' direction, the 5' terminus of the dfs1-PN and at least one nucleotide. The "Figure" column refers to the figure that illustrates the corresponding dfs-NATNA (dfs2-PN/dfs 1-PN).

TABLE 3

Indicators Used to Illustrate Exemplary dfs-PNs

| Second and first fragment nucleotide sequences of: | Exemplary dfs2-PN elements | Exemplary dfs1-PN elements | FIG. |
|---|---|---|---|
| a lower stem element nucleotide sequence II | 5'-S-LII-N-3'F/T | 5'F/T-N-LII-BII-UII-L-UI-BI-LI . . . 3' | 3A, 3B |
| a lower stem element nucleotide sequence I | 5'-S-LII-BII-UII-L-UI-BI-LI-N-3'F/T | 5'F/T-N-LI . . . 3' | 3G, 3H |
| an upper stem element nucleotide sequence I | 5'-S-LII-BII-UII-L-UI-N-3'F/T | 5'F/T-N-UI-BI-LI . . . 3' | 3E, 3F |
| an upper stem element nucleotide sequence II | 5'-S-LII-BII-UII-N-3'F/T | 5'T-N-UII-L-UI-BI-LI . . .3' | 3C, 3D |

Figure 4B:
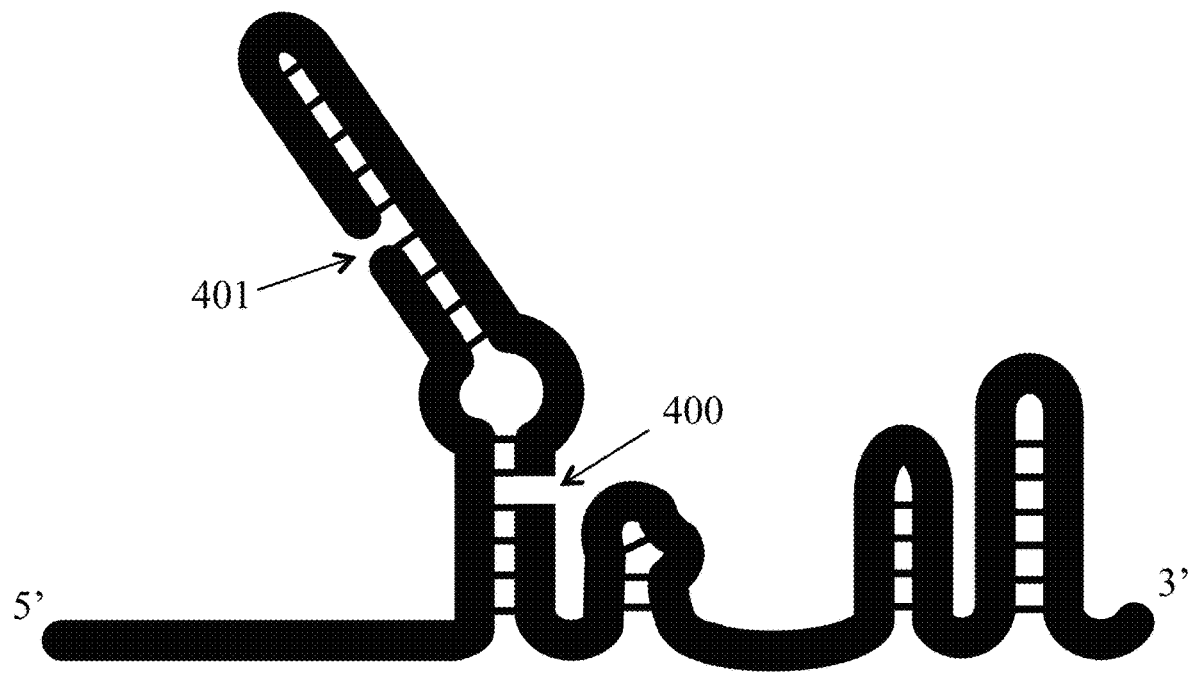
Figure 4C:
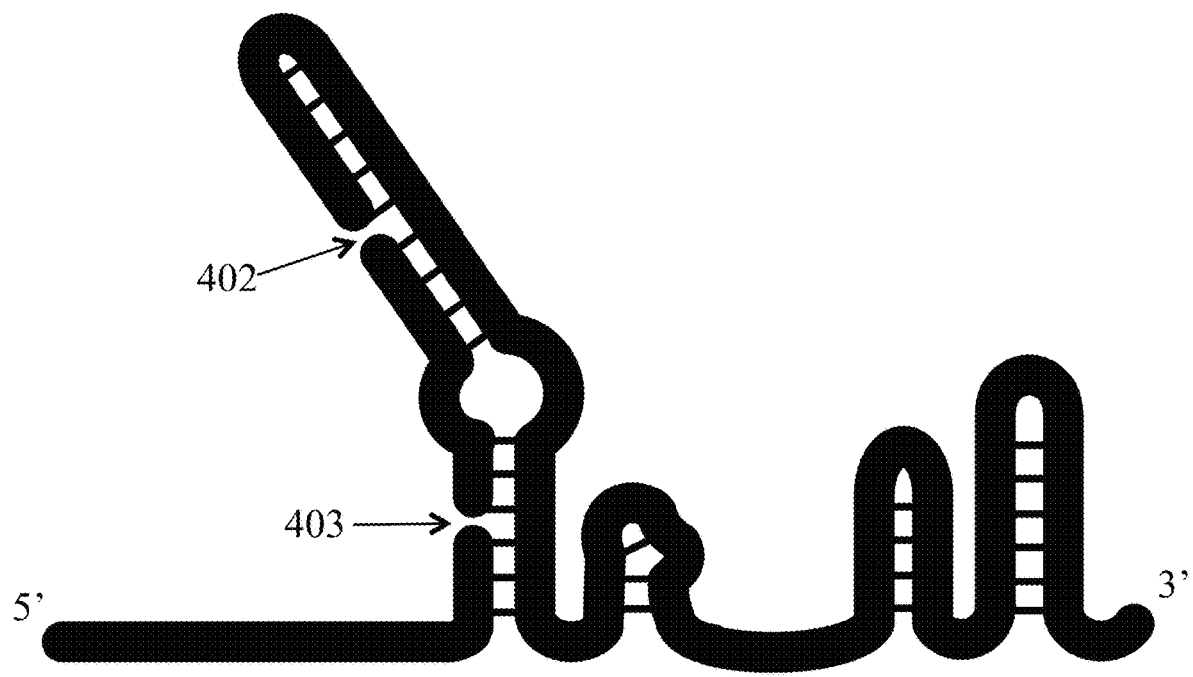
Figure 4D:
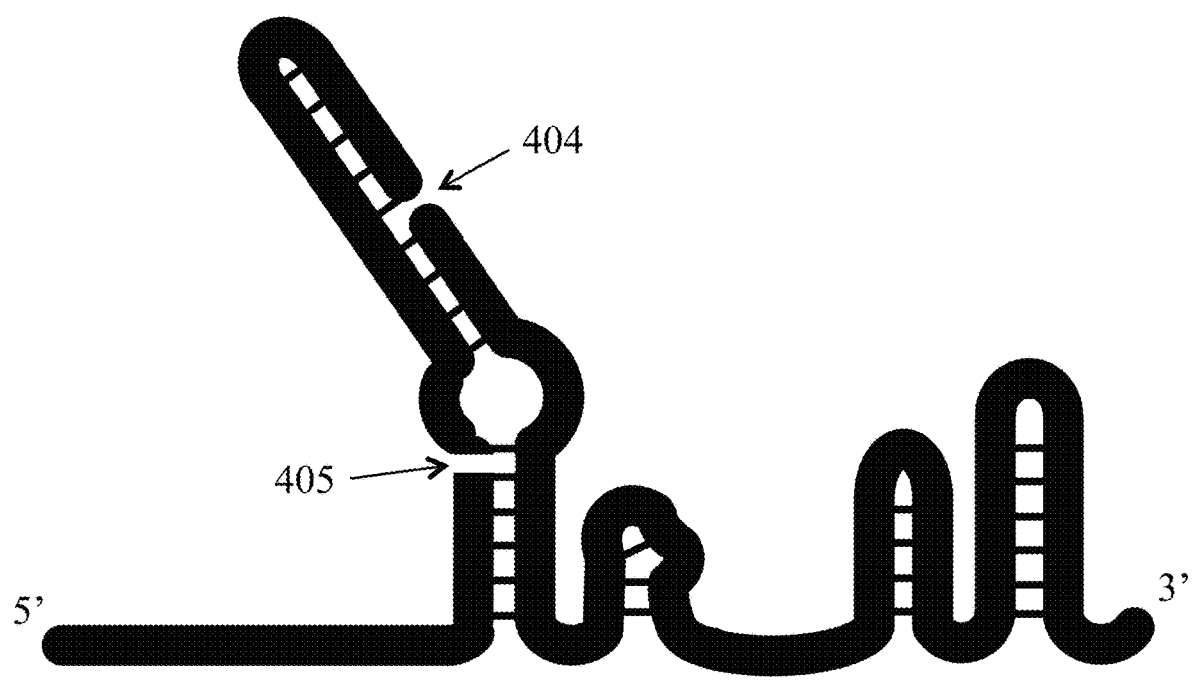

Table 4 is similar to Table 3 except that Table 4 illustrates dfs-NATNAs comprising three polynucleotides: dfs1-PNs, dfs2-PNs, and dfs3-PNs. In Table 4, the indicator "5'F/T-N- . . . N-3'F/T" refers to a third fragment nucleotide sequence comprising, in a 5' to 3' direction, at least one nucleotide and a 3' terminus of the dfs3-PN, at least one nucleotide, and a 5' terminus of the dfs3-PN and at least one nucleotide. The backbone-breakpoint indicators in FIG. 4B, FIG. 4C, and FIG. 4D are as follows: FIG. 4B, 400, dfs1-PN/dfs3-PN, and 401 dfs3-PN/dfs2-PN; FIG. 4C, 402, dfs1-PN/dfs3-PN, and 403, dfs3-PN/dfs2-PN; and FIG. 4D, 404, dfs1-PN/dfs3-PN, and 405, dfs3-PN/dfs2-PN.

TABLE 4

Indicators Used to Illustrate Exemplary dfs-PNs

| Exemplary dfs2-PN elements | Exemplary dfs3-PN elements | Exemplary dfs1-PN elements | FIG. |
|---|---|---|---|
| 5'-S-LII-BII-UII-N-3'F/T | 5'F/T-N-UII-L-UI-BI-LI-N-3'F/T | 5'F/T-N-LI . . . 3' | 4B |
| 5'-S-LII-N-3'F/T | 5'F/T-N-LII-BII-UII N-3'F/T | 5'T-N-UII-L-UI-BI-LI . . . 3' | 4C |
| 5'-S-LII-N-3'F/T | 5'F/T-N-LII-BII-UII-L-UI-N-3'F/T | 5'F/T-N-UI-BI-LI . . . 3' | 4D |

In view of the teachings of the present specification, one of ordinary skill in the art will readily understand how to engineer similar dfs-NATNAs comprising additional polynucleotides.

In other embodiments of this aspect of the present invention, the first stem element does not have a loop element, and one strand of the first stem element comprises one or more non-native 5' termini and one or more non-native 3' termini. Typically, the first stem element comprises a lower stem element 3' of the nucleic acid targeting sequence and 5' of the nexus nucleotide sequence. The lower stem element is adjacent a bulge element, and the bugle element is adjacent an upper stem element (see, e.g., FIG. 5A and Table 5).

Figure 5A:
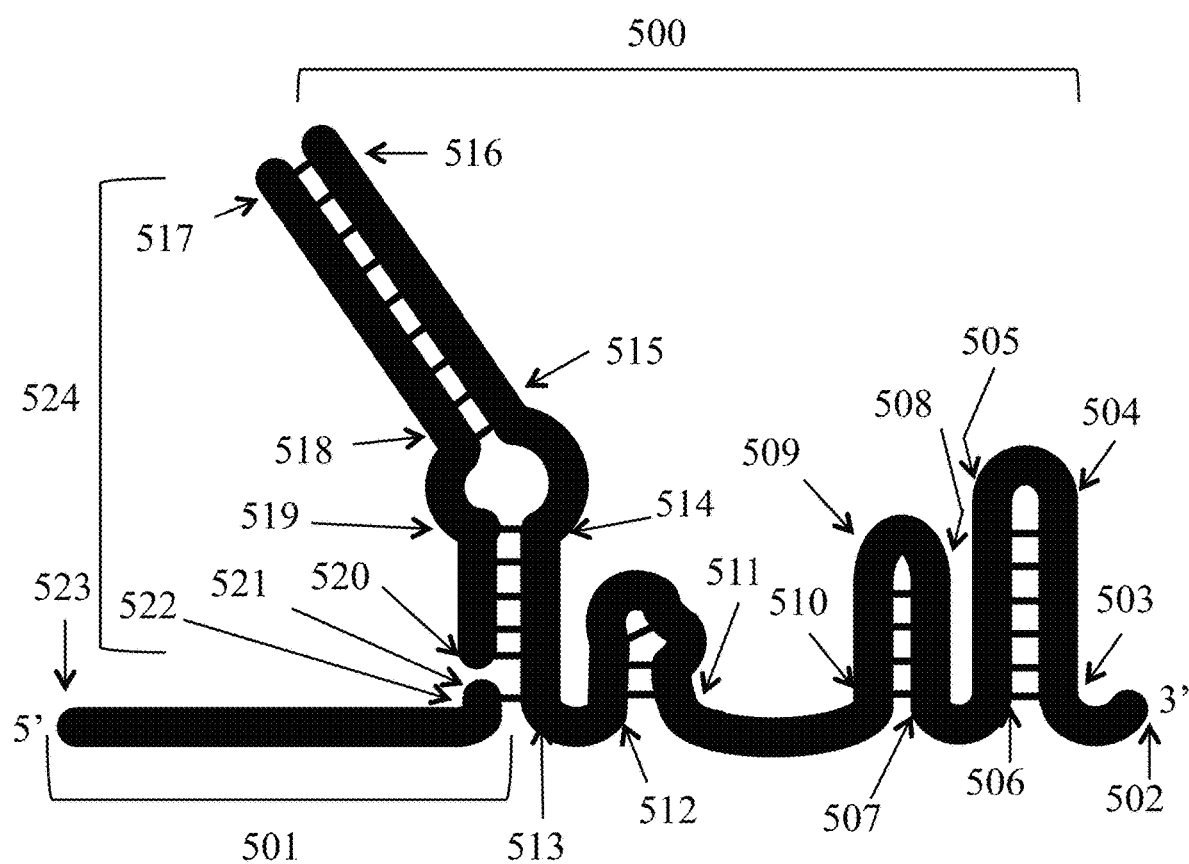
FIG. 5A, FIG. 5B, and FIG. 5C illustrate further embodiments of the Class 2 Type II CRISPR-Cas9-associated discontinuous first-stem nucleic-acid targeting nucleic acids of the present invention.
Figure 5B:
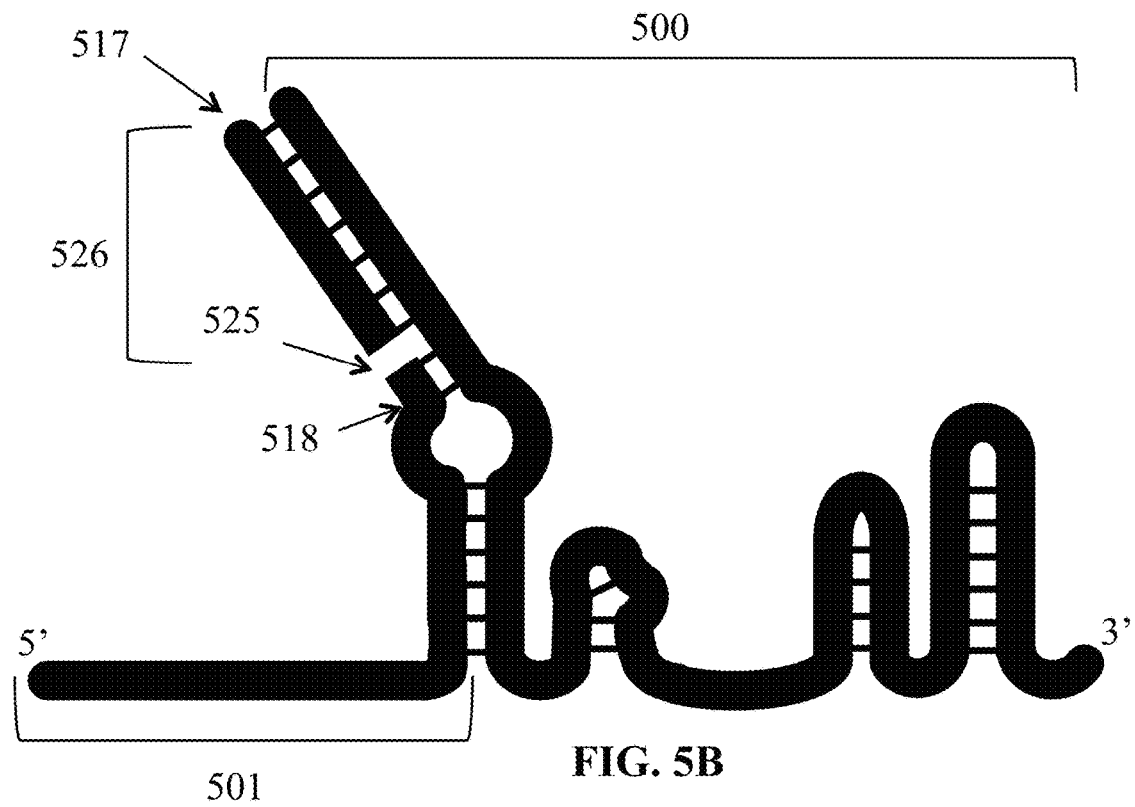
Figure 5C:
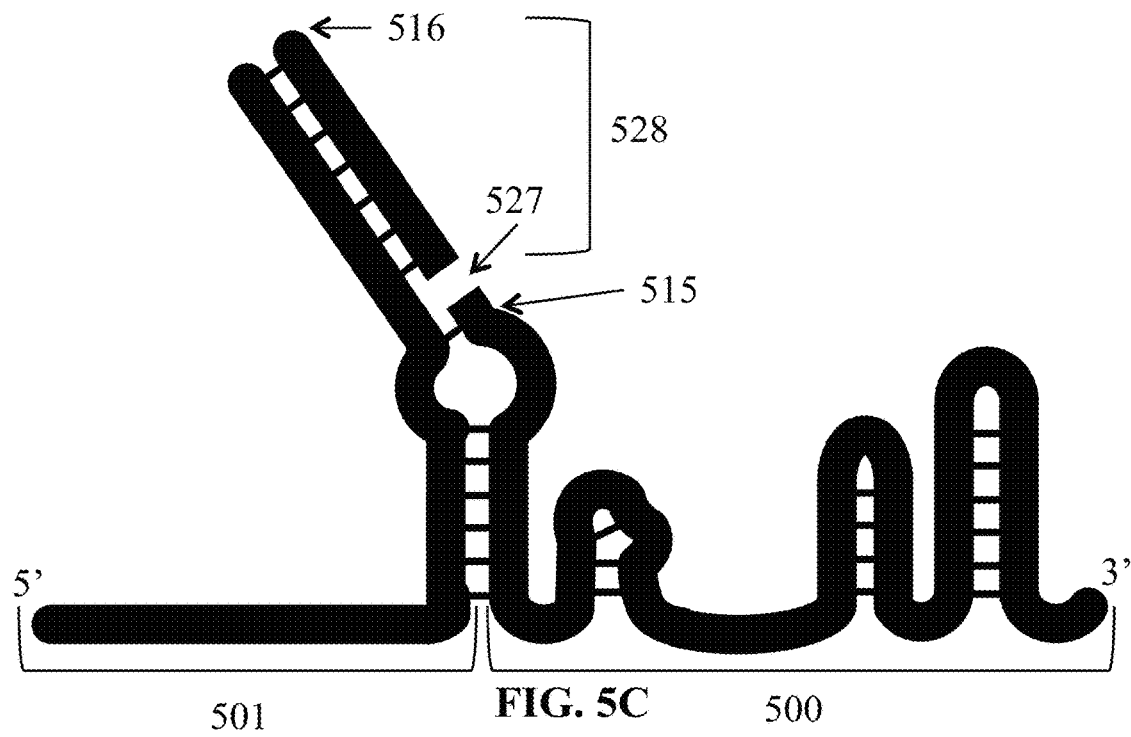

FIG. 5A presents an illustration of a dfs-NATNA having three components. FIG. 5A, 500 illustrates an example of a first Class 2 Type II CRISPR-Cas9-associated discontinuous first-stem single-strand polynucleotide (dfs1-PN) comprising, in a 5' to 3' direction, a 5' terminus, a nexus nucleotide sequence, and a 3' terminus. FIG. 5A, 501 illustrates an example of a second Class 2 Type II CRISPR-Cas9-associated discontinuous first-stem single-strand polynucleotide (dfs2-PN) comprising, in a 5' to 3' direction, a 5' terminus, a nucleic acid target binding sequence and a non-native 3' terminus. FIG. 5A, 524 illustrates an example of a third Class 2 Type II CRISPR-Cas9-associated discontinuous first-stem single-strand polynucleotide (dfs3-PN) comprising, in a 5' to 3' direction, a non-native 5' terminus, a fragment nucleotide sequence 1, a bulge element nucleotide sequence, an upper stem element nucleotide sequence, and a 3' terminus. Table 5 presents a series of indicators used in FIG. 5A, FIG. 5B, and FIG. 5C. In Table 5, "–" is the equivalent of the term "comprising."

TABLE 5

Numerical Indicators Used to Illustrate Regions of Exemplary dfs-PN Nucleotide Sequences

| Indicator | Description |
|---|---|
| FIG. 5A | |
| 500 | a dfs1-PN |
| 501 | a dfs2-PN |
| 524 | a dfs3-PN |
| 502 | a 3' terminus of the dfs1-PN |
| 502-503 | a 3' terminal nucleotide sequence |
| 503-504 | a second adjunct polynucleotide - a 3' hairpin-2 stem element nucleotide sequence II |
| 504-505 | a second adjunct polynucleotide - a 3' hairpin-2 loop element nucleotide sequence |
| 505-506 | a first adjunct polynucleotide - a 3' hairpin-2 stem element nucleotide sequence I |
| 506-507 | a first adjunct polynucleotide - a 3'-hairpin linker element nucleotide sequence |
| 507-508 | a first adjunct polynucleotide - a 3' hairpin-1 stem element nucleotide sequence II |
| 508-509 | a first adjunct polynucleotide - a 3' hairpin-1 loop element nucleotide sequence |
| 503-506 | a 3' hairpin-2 element |
| 510-507 | a 3' hairpin-1 element |
| 509-510 | a nexus nucleotide sequence - a 3' hairpin-1 stem element nucleotide sequence I |
| 510-511 | a nexus nucleotide sequence - a nexus 3' linker nucleotide sequence |
| 511-512 | a nexus element - a nexus nucleotide sequence - a nexus element nucleotide sequence |
| 512-513 | a nexus nucleotide sequence - a nexus 5' linker nucleotide sequence |
| 513-514 | a first stem element nucleotide sequence I - a lower stem element nucleotide sequence I |
| 514-515 | a first stem element nucleotide sequence I - a bulge element nucleotide sequence I |
| 515-516 | a first stem element nucleotide sequence I - an upper stem element nucleotide sequence I |
| 517-518 | a first stem element nucleotide sequence II - an upper stem element nucleotide sequence II |
| 518-519 | a first stem element nucleotide sequence II - a bulge element nucleotide sequence II |
| 519-522 | a first stem element nucleotide sequence II - a lower stem element nucleotide sequence II |
| 519-520 | a first stem element nucleotide sequence II - a lower stem element nucleotide sequence II - a fragment nucleotide sequence 1 |
| 521-522 | a first stem element nucleotide sequence II - a lower stem element nucleotide sequence II - a fragment nucleotide sequence 2 |
| 520 | a 5' terminus of the dfs3-PN (a non-native terminus) |
| 521 | a 3' terminus of the dfs2-PN (a non-native terminus) |
| 518-517/ | a upper stem element |

TABLE 5-continued

Numerical Indicators Used to Illustrate Regions of Exemplary dfs-PN Nucleotide Sequences

| Indicator | Description |
|---|---|
| 515-516 518-519/ 514-515 | a bulge element |
| 519-522/ 513-514 | a lower stem element |
| 522-523 | a nucleic acid target binding sequence |
| 516 | a 5' terminus of the dfs1-PN |
| 523 | a 5' terminus of the dfs2-PN |

FIG. 5B

| | |
|---|---|
| 500 | a dfs1-PN |
| 501 | a dfs2-PN |
| 517-518 | a first stem element nucleotide sequence II - an upper stem element nucleotide sequence II |
| 525 | an indicator of a breakpoint in an upper stem element nucleotide sequence II resulting in a non-native 3' terminus and a non-native 5' terminus |
| 526 | a dfs3-PN |

FIG. 5C

| | |
|---|---|
| 500 | a dfs1-PN |
| 501 | a dfs2-PN |
| 515-516 | a first stem element nucleotide sequence I - an upper stem element nucleotide sequence I |
| 527 | an indicator of a breakpoint in an upper stem element nucleotide sequence I resulting in a non-native 3' terminus and a non-native 5' terminus |
| 528 | a dfs3-PN |

Typical Class 2 Type II dual-guide polynucleotides comprise a 5'-S-LII-BII-UII-3' polynucleotide and a 5'-UI-BI-LI- . . . 3' polynucleotide; however, typical Class 2 Type II dual-guide polynucleotides do not comprise non-native termini.

Figure 6A:
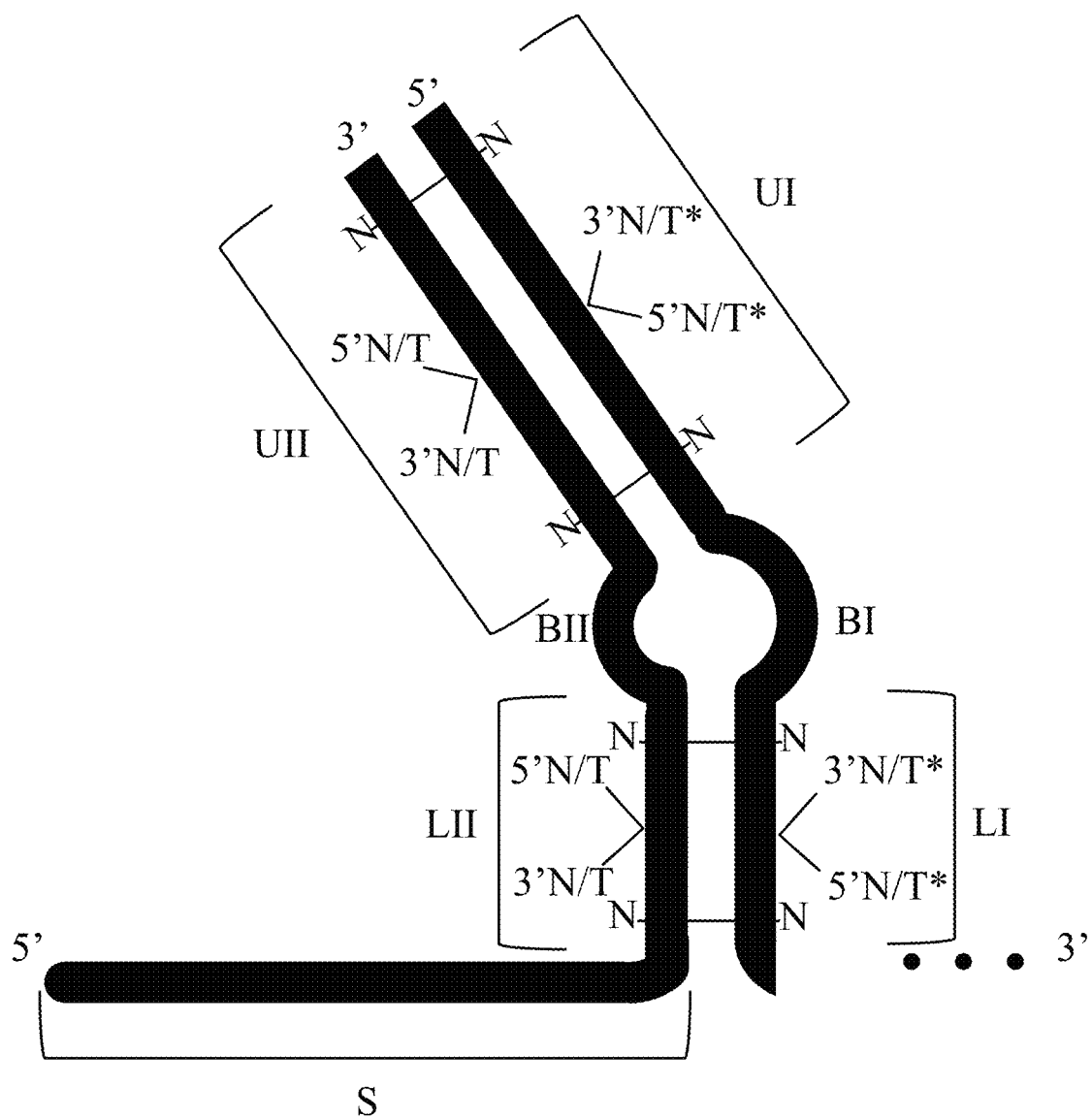
FIG. 6A, FIG. 6B, and FIG. 6C illustrate further embodiments of the Class 2 Type II CRISPR-Cas9-associated discontinuous first-stem nucleic-acid targeting nucleic acids of the present invention.
Figure 6B:
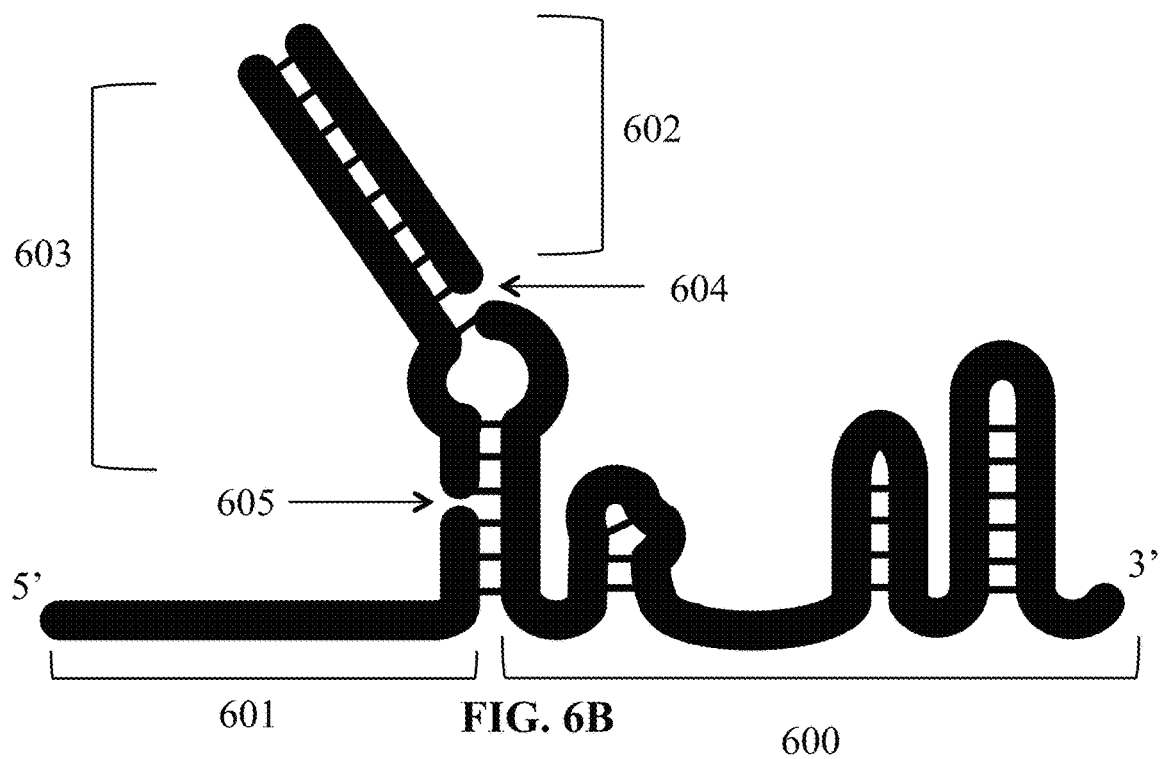
Figure 6C:
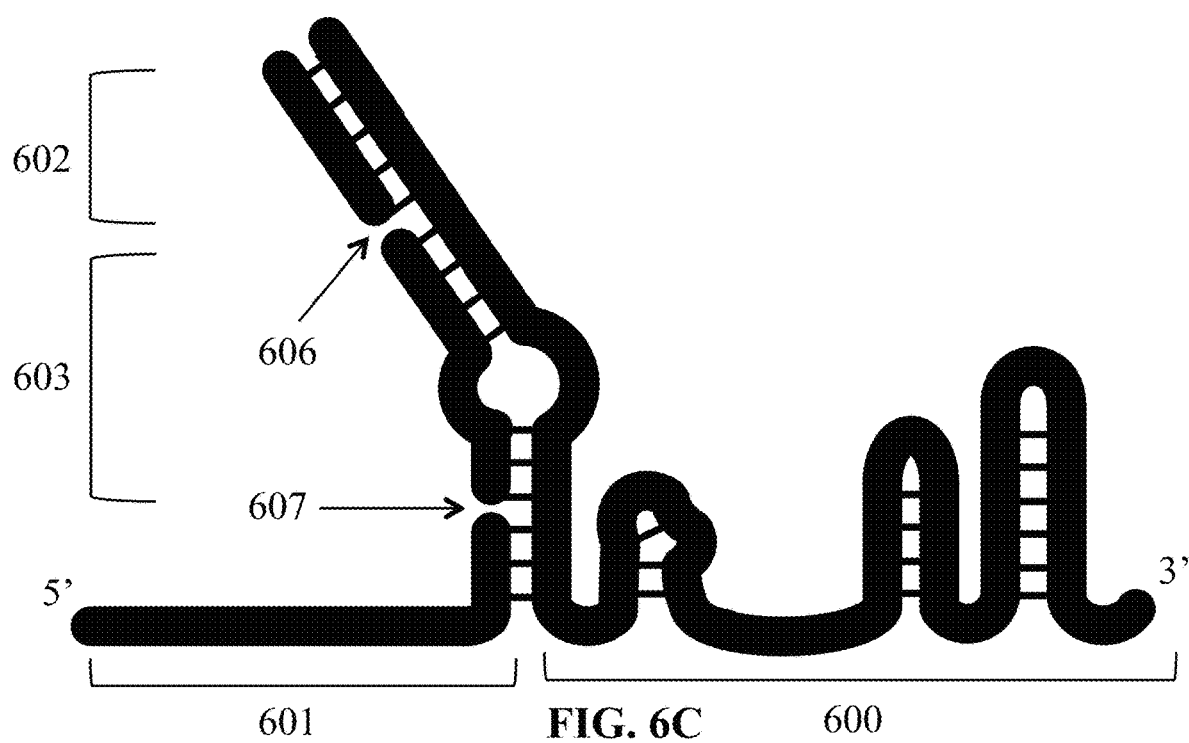

FIG. 6A illustrates exemplary breakpoints for engineering dfs-NATNAs of certain embodiments. The indicators used in FIG. 6A are described in Table 6.

TABLE 6

Indicators Used to Illustrate Exemplary dfs-PNs

| Indicator | Description |
|---|---|
| 5' | 5' terminus of dfs2-PN |
| S | a nucleic acid target binding sequence |
| N | a nucleotide |
| N—N | a pair of hydrogen-bonded nucleotides |
| 3'N/T | a 3' non-native terminus of dfs2-PN |
| 5'N/T | a 5' non-native terminus of dfs3-PN |
| 3'N/T* | a 3' non-native terminus of dfs3-PN |
| 5'N/T* | a 5' non-native terminus of dfs1-PN |
| > | an exemplary engineered break in the nucleic acid backbone resulting in at least one non-native 5' terminus and one non-native 3' terminus |
| LII | a first stem element nucleotide sequence II |
| BII | a bulge element nucleotide sequence II |
| UII | an upper stem element nucleotide sequence I |
| L | a first stem-loop element nucleotide sequence |
| BI | a bulge element nucleotide sequence I |
| LI | a first stem element nucleotide sequence I |
| 5' | a 5' terminus |
| 3' | a 3' terminus |
| . . . | additional nucleotide sequences of dfs1-PN |

Additional embodiments include an engineered break in the nucleic acid backbone of bulge element nucleotide sequence I or II resulting in at least one 5' non-native terminus and one 3' non-native terminus.

Table 7 presents exemplary arrangements of elements within dfs-NATNAs comprising four polynucleotides: dfs1-PNs, dfs2-PNs, dfs3-PN, and dfs4-PN. The elements are given with reference to Table 6.

TABLE 7

Indicators Used to Illustrate Exemplary dfs-PNs

| Indicator | Description |
|---|---|

FIG. 6B

| | |
|---|---|
| 600 | a dfs1-PN |
| 601 | a dfs2-PN |
| 604 | an indicator of a breakpoint in an upper stem element nucleotide sequence I resulting in a non-native 3' terminus and a non-native 5' terminus a dfs3-PN |
| 602 | |
| 605 | an indicator of a breakpoint in a lower stem element nucleotide sequence II resulting in a non-native 3' terminus and a non-native 5' terminus |
| 603 | a dfs4-PN |

FIG. 6C

| | |
|---|---|
| 600 | a dfs1-PN |
| 601 | a dfs2-PN |
| 606 | an indicator of a breakpoint in an upper stem element nucleotide sequence II resulting in a non-native 3' terminus and a non-native 5' terminus |
| 602 | a dfs3-PN |
| 607 | an indicator of a breakpoint in a lower stem element nucleotide sequence II resulting in a non-native 3' terminus and a non-native 5' terminus |
| 603 | a dfs4-PN |

In view of the teachings of the present specification, one of ordinary skill in the art will readily understand how to engineer similar dfs-NATNAs comprising additional polynucleotides.

Additional modifications of dfs-NATNAs will be understood by one of ordinary skill in the in view of the teachings of the present specification and known modifications of Cas9-dual guides and Cas9-single guides, including but not limited to, deletion of one or more 3' hairpin elements (e.g., FIG. 1B, 108, 109; FIG. 2, 208, 209) as well as modifications of the loop element, upper stem element, bulge element, and lower stem element (FIG. 1B, 106, 105, 104; FIG. 2, 204, 203, 205, 202) (see, e.g., U.S. Patent Publication No. 2014-0315985, published 23 Oct. 2014; U.S. Patent Publication No. 2015-0376586, published 31 Dec. 2015; Briner, A. E., et al., Molecular Cell 56(2):333-339 (2014)).

In some embodiments, dfs-NATNAs comprise DNA, RNA, or RNA and DNA.

In addition to known Class 2 crRNAs that can be employed, Example 5 describes a method by which crRNAs of species having a Class 2 CRISPR system can be identified, and Example 6 describes a method by which tracrRNAs of species having, for example, a Class 2 Type II CRISPR-Cas9 system can be identified.

Example 8 describes a method to probe for sites tolerant of modification in Class 2 Type II Cas9 guide polynucleotide backbones (e.g., introduction of a break in the polynucleotide backbone to generate non-native termini).

In a second aspect, the present invention is directed to nucleic acid/protein compositions comprising a dfs-NATNA (e.g., comprising a dfs1-NATNA and a dfs2-NATNA), and a Cas protein (e.g., Cas9 protein) with which the dfs-NATNA is capable of forming a complex. In some embodiments, the Cas protein is catalytically inactive for one or more of endonuclease activities.

In one embodiment of this second aspect of the present invention, a nucleic acid/protein composition comprises a dfs-NATNA as described herein and a Cas9 protein. In another embodiment, the dfs-NATNA is in a complex with the Cas9 protein (dfs-NATNA/Cas9 protein complex or dfs-NATNA/Cas9 nucleoprotein complex). The Cas9 protein can have combinations of the following endonuclease activities: both the RuvC-1 and HNH domains of the Cas9 protein can be catalytically inactive (dCas9), the RuvC-1 domain of the Cas9 protein can be catalytically inactive, or the HNH domain of the Cas9 protein can be catalytically inactive.

Mutations of the Cas9 protein that are enzymatically inactive for RuvC-1-related nuclease activity, HNH-related nuclease activity, or both RuvC-1-related nuclease activity and HNH-related nuclease activity (dCas9) are known in the art.

The site-specific binding of and/or cutting by a nucleoprotein complex comprising a dfs-NATNA and a Cas9 protein, as well as modifications thereof (e.g., introduction of an affinity tag) can be confirmed, if necessary, using the Cas cleavage assay described in Example 3, an electrophoretic mobility shift assay (see, e.g., Garner, M., et al., Nucleic Acids Research 9(13): 3047-3060 (1981); Fried, M., et al., Nucleic Acids Research 9(23):6505-6525 (1981); Fried, M., Electrophoresis 10:366-376 (1989); Gagnon, K., et al., Methods Molecular Biology 703:275-2791 (2011); Fillebeen, C., et al., Journal of Visualized Experiments 3(94) (2014), doi: 10.3791/51959).

Example 3 describes the use of dfs-NATNA/Cas9 protein complexes for in vitro biochemical cleavage assays. Example 2 provides a method for production of double-stranded DNA target sequences for use in the in vitro Cas9 protein cleavage assays. The data presented in Example 3, Table 14, demonstrate that dfs-NATNAs facilitated Cas9 protein mediated site-specific binding to, and subsequence cleavage of, double-stranded DNA target sequences.

To examine site-specific binding, and/or cutting in eukaryotic cells, deep sequencing analysis for detection of nucleic acid target sequence modifications (Example 4) and/or the T7E1 assay for detection of nucleic acid target sequence modifications (Example 7) can be employed.

Example 9 describes the use of dfs-NATNAs to modify nucleic acid target sequences present in human genomic DNA and to measure the level of cleavage activity and specificity of cleavage at such sites. Measurement of the level of cleavage percentage and/or cleavage specificity at a particular site can provide options to identify nucleic acid target sequences having a desired cleavage percentage and/or specificity.

Figure 7A:
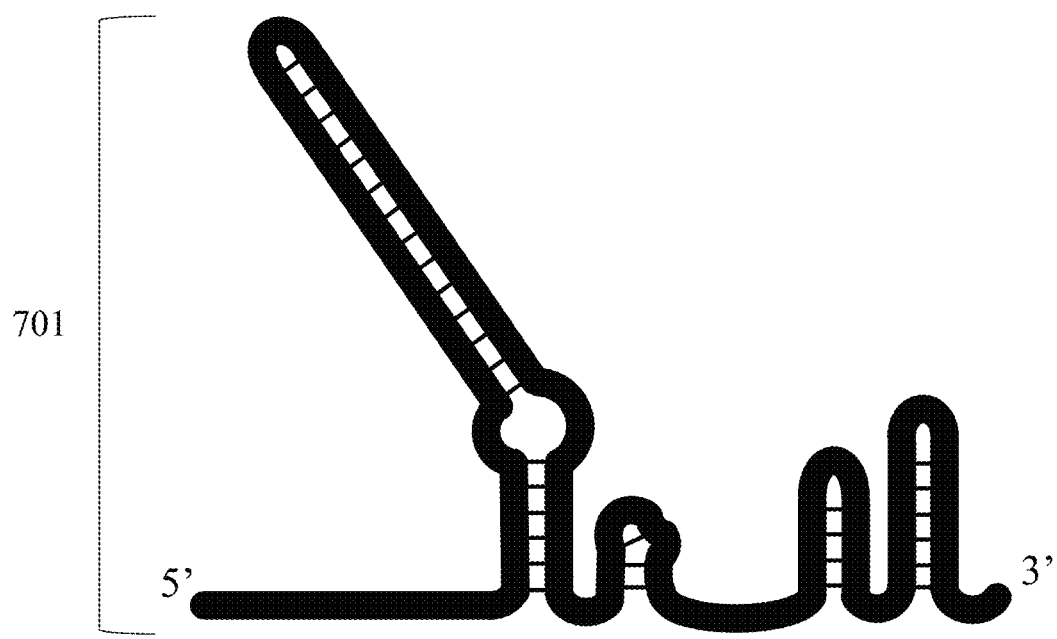
FIG. 7A illustrates a Class 2 Type II CRISPR-Cas sgRNA.
Figure 7B:
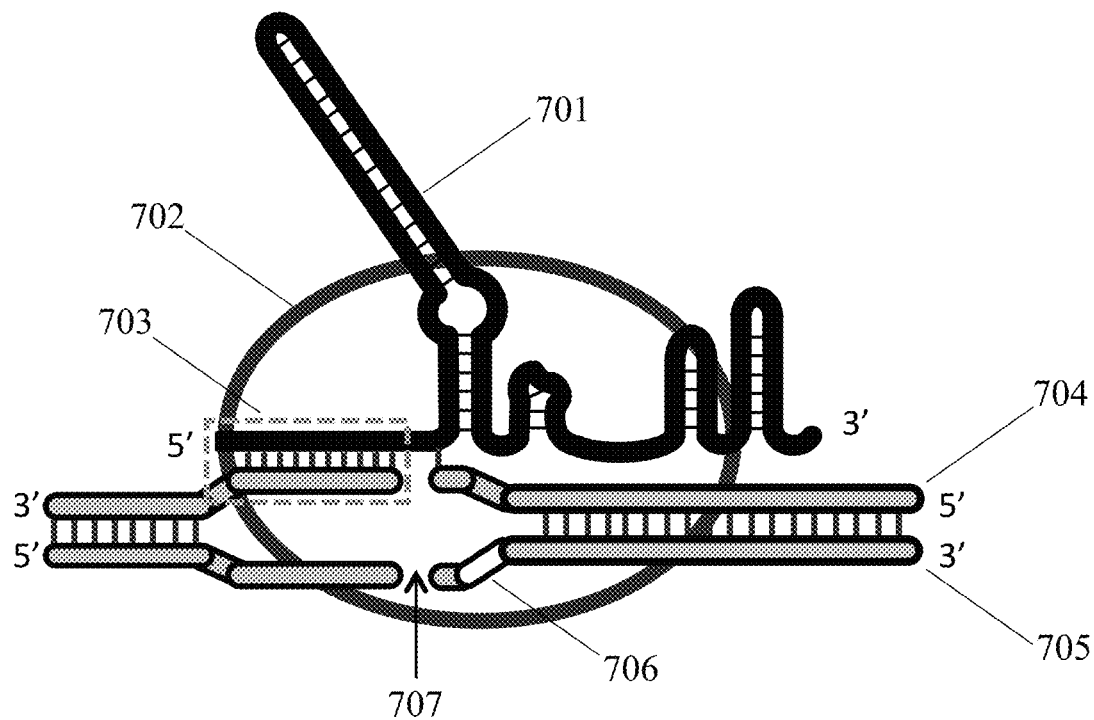
FIG. 7B illustrates an example of a Class 2 Type II CRISPR-Cas9 ribonucleoprotein complex bound to a double-stranded DNA comprising a DNA target sequence.

FIG. 7A illustrates a Class 2 Type II CRISPR-Cas9 sgRNA (FIG. 7A, 701) (compare FIG. 2). FIG. 7B illustrates a CRISPR-Cas9 sgRNA (FIG. 7A, 701)/Cas9 protein ribonucleoprotein complex bound to a double-stranded DNA comprising a DNA target sequence, wherein the ribonucleoprotein complex has cut both strands of the double-stranded DNA target sequence. In FIG. 7B, the sgRNA (FIG. 7B, 701) is complexed with a cognate Cas9 protein (FIG. 7B, 702). The box with dashed lines (FIG. 7B, 703) illustrates the nucleic acid target binding sequence of the sgRNA hybridized to the complementary DNA target sequence in the 3' to 5' DNA strand (FIG. 7B, 704). The location of the cut made by the Cas9 protein of the ribonucleoprotein complex is indicated by the arrow (FIG. 7B, 707). The PAM (FIG. 7B, 706) in the double-stranded DNA is present in the 5' to 3' DNA strand (FIG. 7B, 705).

Figure 8A:
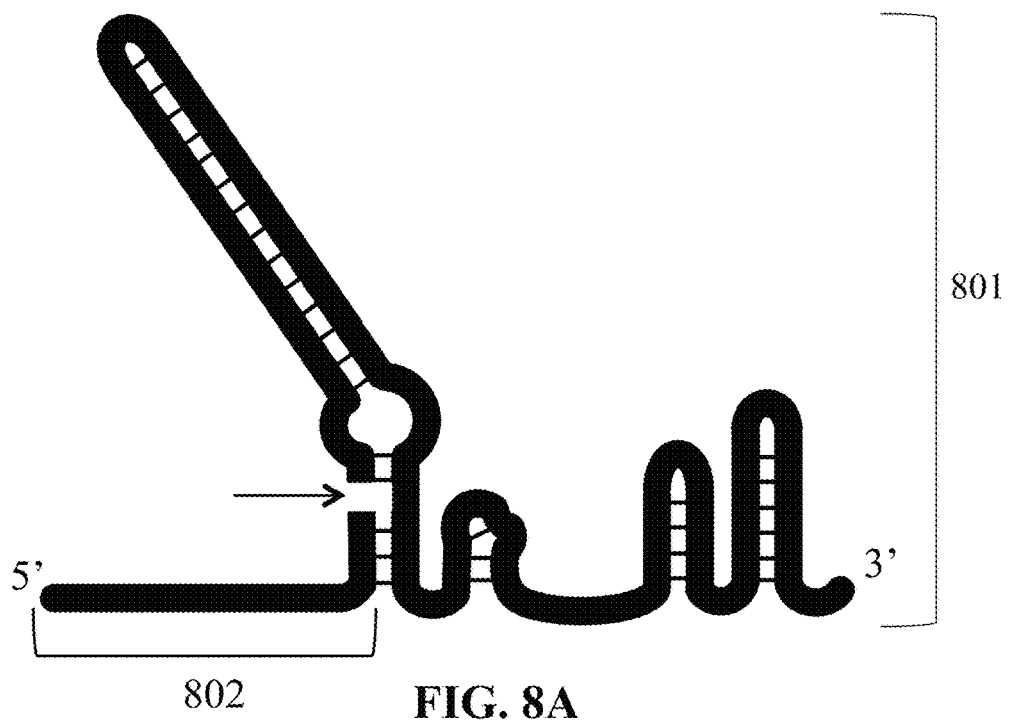
FIG. 8A illustrates an embodiment of the Class 2 Type II CRISPR-Cas9-associated discontinuous first-stem nucleic-acid targeting nucleic acid of the present invention.
Figure 8B:
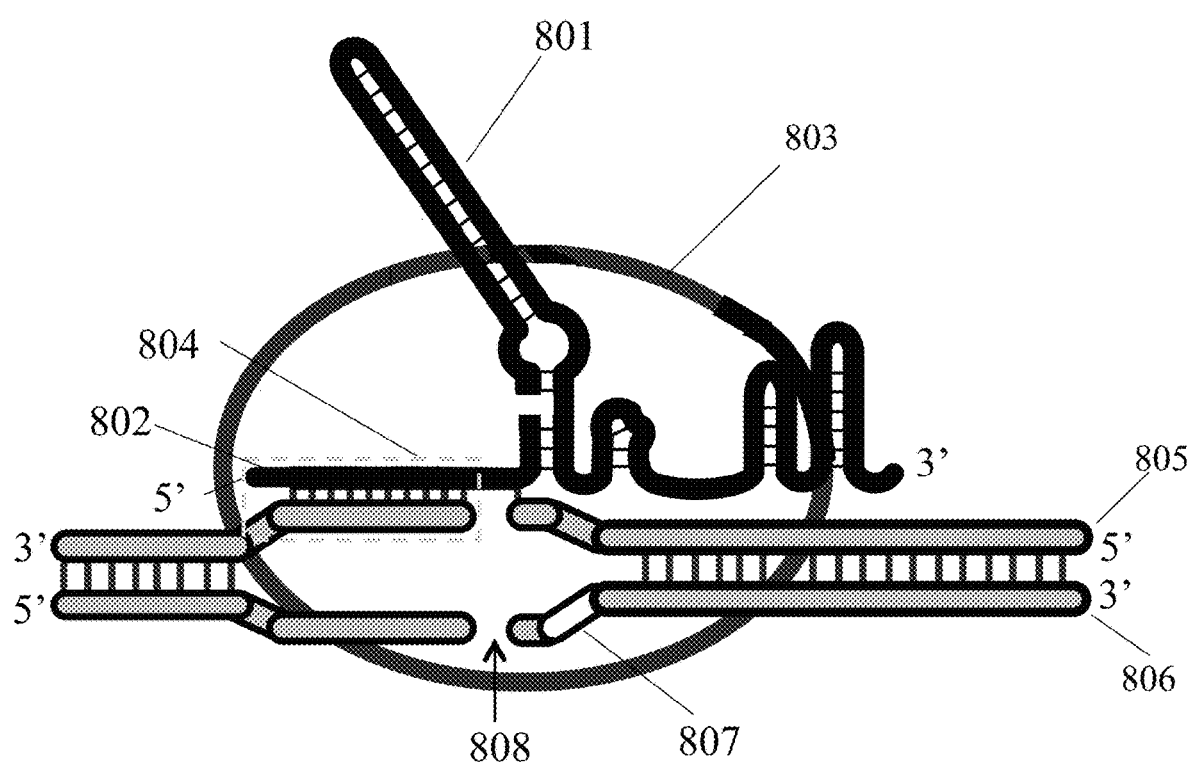
FIG. 8B illustrates an example of Class 2 Type II CRISPR-Cas9-associated discontinuous first-stem nucleic-acid targeting nucleic acid-Cas9 protein nucleoprotein complex of the present invention bound to a double-stranded DNA comprising a DNA target sequence.

An embodiment of a dfs-NATNA of the present invention is shown in FIG. 8A (compare FIG. 3B). A dfs2-PN is represented in FIG. 8A, 802, and a dfs1-PN is represented in FIG. 8A, 801. FIG. 8B illustrates a dfs-NATNA (FIG. 8B, 801, 802)/Cas9 protein nucleoprotein complex bound to a double-stranded DNA comprising a DNA target sequence, wherein the nucleoprotein complex has cut both strands of the double-stranded DNA target sequence. In FIG. 8B, a dfs1-PN (FIG. 8B, 801) and a dfs2-PN (FIG. 8B, 802) are complexed with a cognate Cas9 protein (FIG. 8B, 803). The box with dashed lines (FIG. 8B, 804) illustrates the dfs2-PN hybridized to the complementary DNA target sequence in the 3' to 5' DNA strand (FIG. 8B, 805). The location of the cut made by the Cas9 protein of the nucleoprotein complex is indicated by the arrow (FIG. 8B, 808). The PAM (FIG. 8B, 807) in the double-stranded DNA is present in the 5' to 3' DNA strand (FIG. 8B, 806).

In some embodiments of the present invention, affinity tags are introduced into one or more polynucleotides of a dfs-NATNA composition (e.g., dfs2-PN/dfs1-PN) and a cognate Cas protein, or into the dfs2-PN and the cognate Cas protein, or into the dfs1-PN and the cognate Cas protein. For example, a nucleic acid sequence within, or a nucleic acid sequence appended to, the dfs2-PN can be modified to comprise an affinity sequence. Such affinity sequences can comprise a MS2 binding sequence, a U1A binding sequence, a stem-loop sequence (e.g., a Cas6 protein binding sequence such as a Csy4 protein binding sequence), an eIF4A binding sequence, a Transcription Activator-Like Effector (TALE) binding sequence (see, e.g., Valton, J., et al., Journal of Biological Chemistry 287(46):38427-38432 (2012)), or a zinc finger (ZFN) domain binding sequence (see, e.g., Font, J., et al., Methods Molecular Biology 649:479-491 (2010); Isalan, M., et al., Nature Biotechnology 19(7):656-660 (2001)). In some embodiments, dfs1-PN can be similarly modified, or both the dfs1-PN and the dfs2-PN can be modified. The Cas protein coding sequence can then be modified to comprise a corresponding affinity tag: an MS2 coding sequence, a U1A coding sequence, stem-loop binding protein coding sequence (e.g., an enzymatically (riboendonuclease) inactive Csy4 protein that binds the Csy4 protein sequence), an eIF4A coding sequence, a TALE coding sequence, or a ZFN domain coding sequence, respectively. Typically, enzymatically inactive nucleic acid binding proteins that retain sequence specific nucleic acid binding are used (e.g., a riboendonuclease inactive Csy4 protein (dCsy4)); however, in some embodiments, enzymatically active nucleic acid binding proteins or nucleic acid proteins with altered enzymatic activity can be used. When both dfs1-PN and dfs2-PN are modified with an affinity sequence, preferably the two affinity sequences typically are not the same.

In some embodiments, the dfs2-PN is tethered to the Cas protein at a location to bring the dfs2-PN into proximity with the nucleic acid binding channel of the Cas protein. In other embodiments, the dfs2-PN is tethered to the Cas protein at a location to stabilize the dfs2-PN/Cas protein interaction.

Example 10 provides an example of the use of a Cas9-dCsy4 fusion protein, and a dfs2-PN comprising a nucleic acid target binding sequence that is modified to include the RNA binding sequence corresponding to the dCsy4 protein. This combination of a Cas9-dCsy4 fusion protein and attachment of the corresponding Csy4 protein binding sequence to a dfs2-PN illustrates a mechanism that can be used to bring the dfs2-PN comprising a nucleic acid target binding sequence into proximity with the nucleic acid binding channel of the Cas9 protein.

Figure 12:
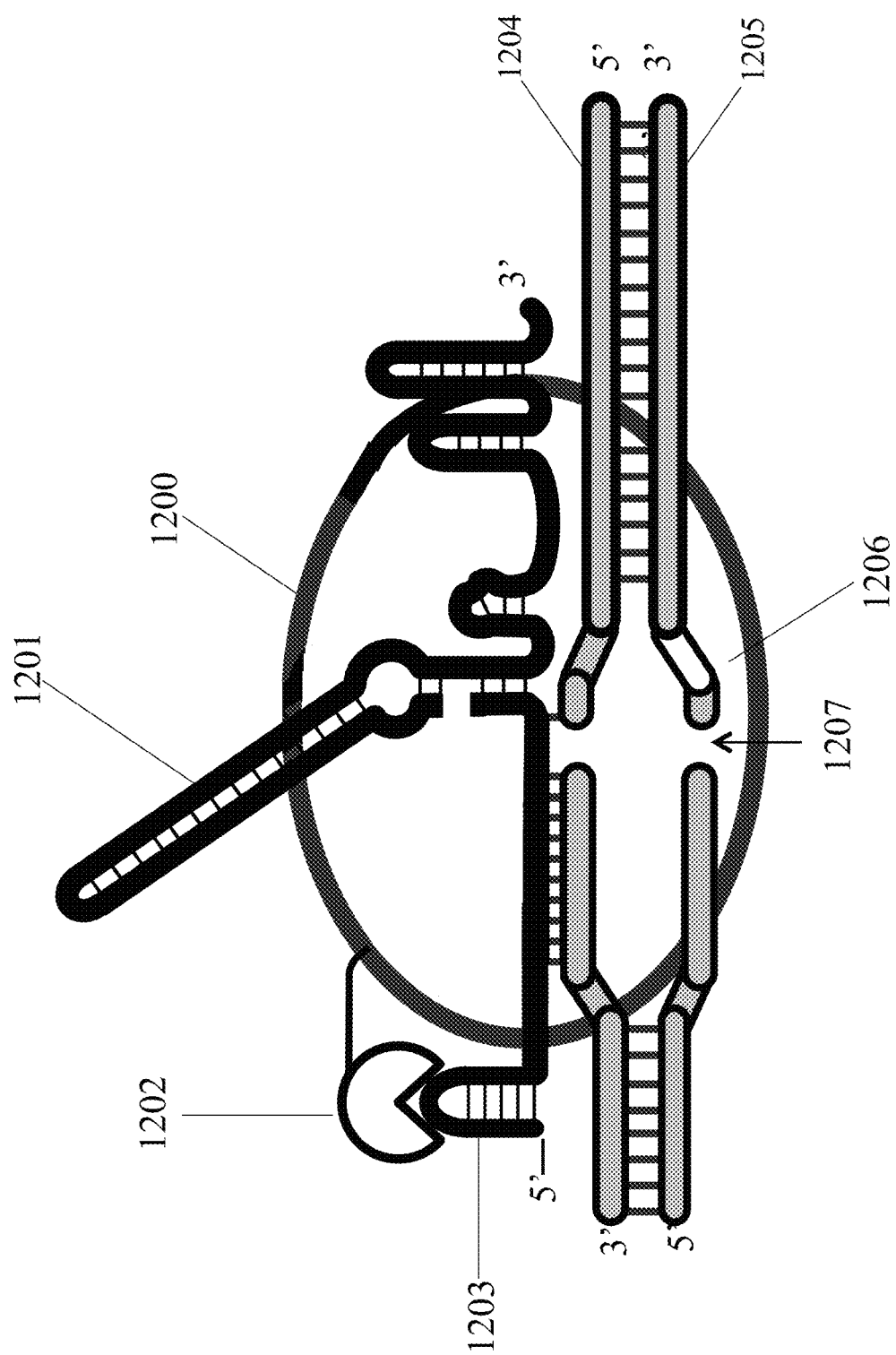
FIG. 12 illustrates an example of Class 2 Type II CRISPR-Cas9-associated discontinuous first-stem nucleic-acid targeting nucleic acid/Cas9 protein ribonucleoprotein complex of the present invention bound to a double-stranded DNA comprising a DNA target sequence.

FIG. 12 illustrates a dfs-NATNA/Cas9-dCsy4 fusion protein ribonucleoprotein complex bound to a double-stranded DNA comprising a DNA target sequence. The ribonucleoprotein complex has bound to and cut both strands of the double-stranded DNA target sequence. In FIG. 12, a dfs1-PN (FIG. 12, 1201) and a dfs2-PN (FIG. 12, 1203) comprising a Csy4 RNA binding sequence (which is illustrated as the hairpin in the 5'-end sequence of the dfs2-PN) form a ribonucleoprotein complex with cognate Cas9-dCsy4 fusion protein (FIG. 12, 1200, 1202). The Cas9 protein comprises a fusion protein comprising the Cas9 protein (FIG. 12, 1200) and a dCsy4 (enzymatically inactive Csy4) domain (FIG. 12, 1202) that binds the Csy4 RNA binding sequence of the dfs2-PN. The dfs2-PN is hybridized to the complementary DNA target sequence in the 3' to 5' DNA strand (FIG. 12, 1204). The location of the cut made by the Cas9 protein of the ribonucleoprotein complex is indicated by the arrow (FIG. 12, 1207). The PAM (FIG. 12, 1206) in the double-stranded DNA is present in the 5' to 3' DNA strand (FIG. 12, 1205). The binding of the dCsy4 domain of the fusion protein to the Csy4 RNA binding sequence shows an example of a method that can be used to bring the dfs2-PN into proximity with the nucleic acid binding channel of the Cas9 protein. In some embodiments, in addition to the RNA sequence comprising the Csy4 protein binding sequence, the dfs1-PN and/or dfs2-PN can further comprise RNA.

Examples of targets for cross-linking moieties include, but are not limited to, amines (e.g., lysines or a protein N-terminus), sulfhydryls (e.g., cysteines), carbohydrates (e.g., oxidized sugars), and carboxyls (e.g., protein or peptide C-terminus, aspartic acid, or glutamic acid).

Examples of chemical cross-linking moieties include, but are not limited to, carbodiimide, N-hydroxysuccinimide esters (NHS) ester, imidoesters, maleimides, haloacetyls, pyridyldisulfides, hydrazides, alkoxyamines, diazirines, aryl azides, and isocyanates.

A wide variety of nucleic acid/protein cross-linking moieties are commercially available, including, but not limited to thiols (e.g., 5' thiol C6, dithiol phosphoramidite (DTPA), and 3' thiol C3) (e.g., Integrated DNA Technologies, Inc., Coralville, Iowa; Thermo Fisher Scientific, South San Francisco, Calif.; ProteoChem, Loves Park, Ill.; BroadPharm, San Diego, Calif.).

Following the guidance of the present specification, one of ordinary skill in the art can modify one or more polynucleotides of a dfs-NATNA as well as a cognate Cas protein with cross-linking moieties using established chemical methods (e.g., Methods of Chemistry of Protein and Nucleic Acid Cross-Linking and Conjugation, Second Edition, Shan S. Wong and David M. Jameson, CRC Press, ISBN-13 978-0849374913 (2011); Bioconjugate Techniques, Third Edition, Greg T. Hermanson, Academic Press, ISBN-13 978-0123822390 (2013); Chemistry of Bioconjugates—Synthesis, Characterization, and Biomedical Applications, First Edition, Ravin Narain (Editor), Wiley, ISBN-13 978-1118359143 (2014); Bioconjugation Protocols—Strategies and Methods (Series: Methods in Molecular Biology (Book 751), Second Edition, Sonny S. Mark (Editor), Humana Press, ISBN-13 978-1617791505 (2011); Crosslinking Technical Handbook, Thermo Fisher Scientific, South San Francisco, Calif. (2009, 2012).

In some embodiments, the Cas protein primary sequence is engineered to comprise an amino acid residue at a particular residue position in the Cas protein (e.g., substitution or insertion of a Cys amino acid at a position that is not a Cys amino acid in the corresponding wild-type Cas protein) useful for cross linking to a cross-linking moiety present in one or more polynucleotides of a dfs-NATNA.

Example 11 describes the modification of dfs-NATNAs to include a cross-linking agent, as well as modification of selected amino acid residues in the Class 2 Type II CRISPR-Cas9 protein. This combination of a modified Cas9 protein and modified dfs-PNs illustrates another method that can be used to bring the nucleic acid target binding sequence of a dfs-PN into proximity with the nucleic acid binding channel of the Cas9 protein.

Figure 11:
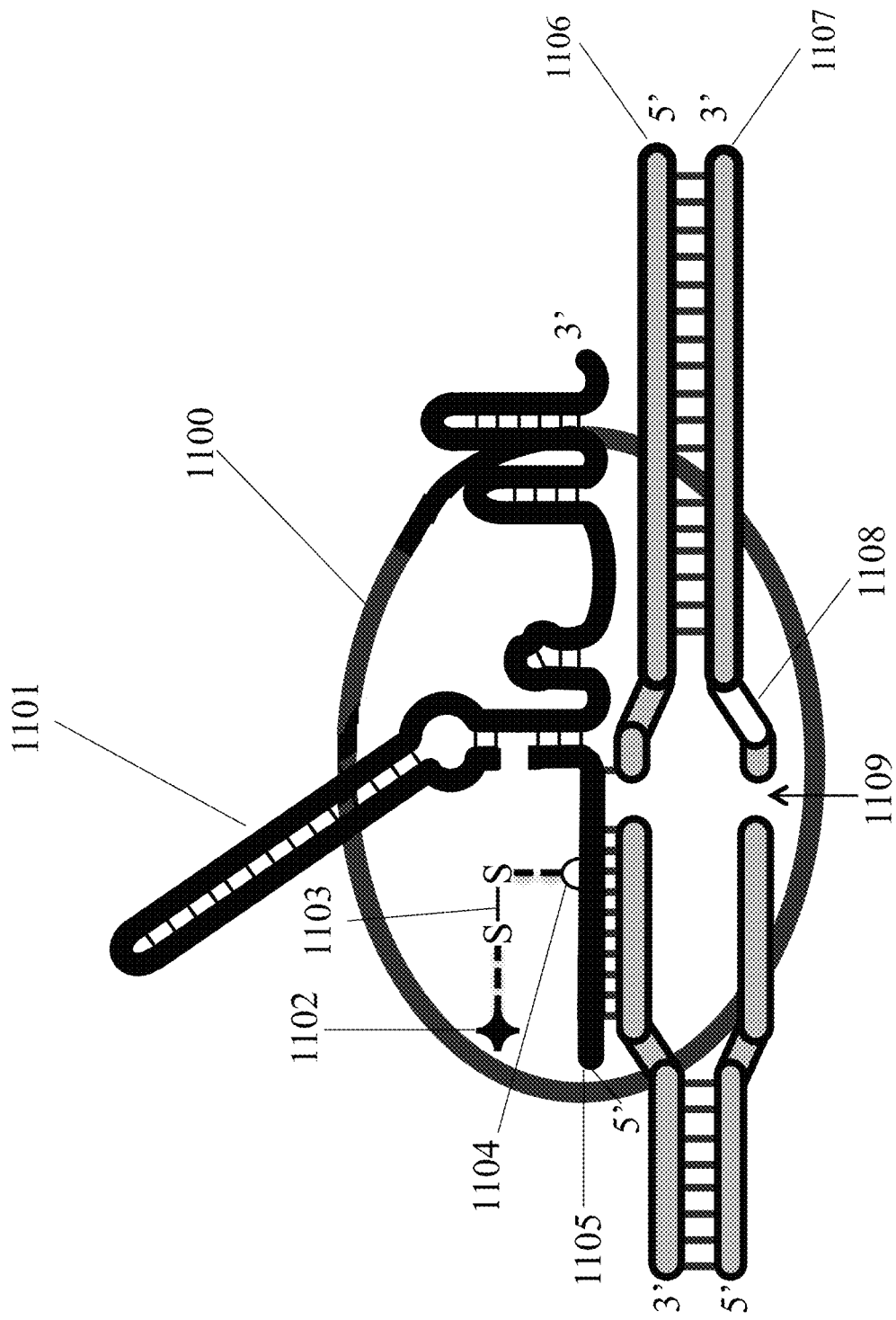
FIG. 11 illustrates an example of Class 2 Type II CRISPR-Cas9-associated discontinuous first-stem nucleic-acid targeting nucleic acid/Cas9 protein nucleoprotein complex of the present invention bound to a double-stranded DNA comprising a DNA target sequence.

FIG. 11 illustrates a thiolated dfs-NATNA/modified Cas9 protein nucleoprotein complex bound to a double-stranded DNA comprising a DNA target sequence. The nucleoprotein complex has bound to and cut both strands of the double-stranded DNA target sequence. In FIG. 11, a dfs1-PN (FIG. 11, 1101) and a thiolated dfs2-PN (FIG. 11, 1105) are complexed with a cognate modified-Cas9 protein (FIG. 11, 1100, 1102). The thiolated dfs2-PN is hybridized to the complementary DNA target sequence in the 3' to 5' DNA strand (FIG. 11, 1106). The location of the cut made by the Cas9 protein of the nucleoprotein complex is indicated by the arrow (FIG. 11, 1109). The PAM (FIG. 11, 1108) in the double-stranded DNA is present in the 5' to 3' DNA strand (FIG. 11, 1107). The modified Cas9 protein comprises an engineered Cas9 protein having a cysteine (Cys) substitution of a non-Cys amino acid residue (FIG. 11, 1102) and the thiolated dfs2-PN comprises a thiol cross-linking moiety (FIG. 11, 1104). The substituted Cys amino acid residue of the engineered Cas9 protein is covalently bound through the S—S bond (FIG. 11, 1103) to the dfs2-PN thiol cross-linking moiety. The S—S bond between the substituted Cys residue and the dfs2-PN thiol cross-linking moiety shows an example of a method that can be used to bring the dfs2-PN into proximity with the nucleic acid binding channel of the Cas9 protein.

A further application of a cross-linking moiety is to provide one or more photoactive nucleotide in one or more of the polynucleotides of a dfs-NATNA, wherein the photoactive nucleotide is positioned to maximize contact between the one or more photoactive nucleotides and one or more photoreactive amino acids. UV light can be used to induce cross linking between the one or more photoactive nucleotides and the one or more photoreactive amino acids. In one embodiment, a cross-linking moiety for use in the practice of the present invention is a cross-linkable polynucleotide comprising a contiguous run of uracil nucleotides (poly-U) or a run of uracil nucleotides alternating with other nucleotides. In another embodiment, a cross-linking moiety can be a cross-linkable polynucleotide comprising a contiguous run of thymidine nucleotides (poly-T) or a run of thymidine nucleotides alternating with other nucleotides. Such cross-linkable polynucleotides are, for example, positioned in one or more of the polynucleotides of a dfs-NATNA to maximize contact with one or more photoreactive amino acids of a Cas protein.

A large number of photoreactive amino acids can be added photochemically (e.g., 254 nm) to uracil (see, e.g., Smith, K. C., et al., "DNA-Protein Crosslinks," available at www.photobiology.info/Smith_Shetlar.html) including, but not limited to, glycine, serine, phenylalanine, tyrosine, tryptophan, cystine, cysteine, methionine, histidine, arginine and lysine. The most reactive amino acids are phenylalanine, tyrosine and cysteine. A number of photoreactive amino acids can be added photochemically to thymidine including, but not limited to, lysine, arginine, cysteine and cystine. Accordingly, regions of a Cas protein complex comprising one or more photoreactive amino acid can be evaluated for the ability to act as cross-linking moieties. Also, the Cas protein coding sequence can be modified to introduce a photoreactive amino acid (an affinity tag) in a position suitable to come into proximity of a photoactive nucleotide (an affinity tag) in an affinity sequence of one or more polynucleotides of a dfs-NATNA.

Further examples of photoreactive cross-linking moieties include, but are not limited to, photo reactive amino acid analogs (L-photo leucine, L-photo-methionine, p-benzoyl-L-phenylalanine) and photoactivatable ribonucleosides (halogenated and thione containing ribonucleoside analogues, such as 5-Bromo-dUTP, Azide-PEG4-aminoallyl-dUTP, 4-thiouridine, 6-thioguanosine, preferred reaction with tyrosines, phenylalanines and tryptophanes). General photoreactive cross-linking moieties include, but are not limited to, aryl azides, azido-methyl-coumarins, benzophenones, anthraquinones, certain diazo compounds, diazirines, and psoralen derivatives.

There are a number of photoreactive cross-linking analogs that serve as substrates for RNA polymerases for introduction into RNA molecules including, but not limited to, 4-thio-UTP, 5-azido-UTP, 5-bromo-UTP and 8-azido-ATP, 5-APAS-UTP, 5-APAS-CTP, 8-APAS-ATP, and 8-N(3)AMP (see, e.g., C. Costas, et al., Nucleic Acids Research 28(9): 1849-1858 (2000); Gaur R. K., Methods Molecular Biology 488:167-180 (2008)).

A variety of cross-linking methods and moieties are commercially available, for example, from TriLink Biotechnologies (San Diego, Calif.) including, for photocross-linking: RNA—4-Thiouridine, 5-Bromouridine-5'-Triphosphate, 5-Iodouridine-5'-Triphosphate, 4-Thiouridine-5'-Triphosphate/DNA—6-Thio-dG, and 4-Thiothymidine.

Examples of general cross-linking reagents include, but are not limited to, glutaraldehyde and formaldehyde. Furthermore, monofunctional (e.g., one-function cross-linking moieties, such as alkyl imidates) and bifunctional (two cross-linking moieties, such as disuccinimidyl suberate (DSS)) or trifunctional cross-linking moieties) can be used, as well as homobifunctional (DSS) and heterobifunctional (sulfosuccinimidyl-4-(N-maleimidomethyl) cyclohexane-1-carboxylate (Sulfo-SMCC)) cross-linking moieties. Additionally, cross-linking moieties can comprise different spacer lengths (C3, C6, PEG spacers, and others).

In some embodiments, a dfs2-PN is cross linked to a residue of the Cas protein at a location to bring the dfss2-PN into proximity with the nucleic acid binding channel of the Cas protein (e.g., Cas9 protein). In some embodiments, a dfs1-PN is tethered to a residue of the Cas protein at a location to stabilize the dfs1-PN/Cas protein interaction.

In another embodiment, a ligand-binding moiety is introduced into the Cas protein and one or more polynucleotides of a dfs-NATNA are modified to contain the ligand. A ligand/ligand-binding moiety useful in the practice of the present invention is avidin or streptavidin/Biotin (see, e.g., Livnah, O., et al., Proceedings of the National Academy of Sciences of the United States of America 90(11):5076-5080 (1993); Airenne, K. J., et al., Biomolecular Engineering 16(1-4):87-92 (1999)). One example of a Cas protein with a ligand-binding moiety is a Cas protein fused to a ligand avidin or streptavidin designed to bind one or more polynucleotides of a dfs-NATNA at a 5' or 3' terminus. Biotin is a high affinity and high specificity ligand for the avidin or streptavidin protein. By fusing an avidin or streptavidin polypeptide chain to a Cas protein, the Cas protein has a high affinity and specificity for one or more 5' or 3' biotinylated polynucleotide of a dfs-NATNA (e.g., a dfs2-PN).

For example, biotinylation is can be in close proximity to the 5' or 3' terminus of a dfs2-PN. The sequence of the dfs2-PN and location of the biotin can be provided to commercial manufacturers for synthesis of the dfs2-PN-biotin or can be added through the use of an artificial third-base pair (e.g., an unnatural base pair between 7-(2-thienyl)imidazo[4,5-b]pyridine (Ds) and pyrrole-2-carbaldehyde (Pa)) in an in vitro transcription reaction (see, e.g., Hirao, I., et al., Nature Methods 3(9):729-735 (2006)). dfs2-PNs can be similarly modified at 5'-end sequences, 3'-end sequences, or positions between the 5'-end and the 3'-end sequences. Changes to cleavage percentage and specificity of the ligand-binding modified Cas protein-ligand-binding moiety/dfs-NATNA-ligand moiety can be evaluated as described below in Example 3 and Example 4.

Examples of other ligand moieties and ligand-binding moieties that can be similarly used include, but are not limited to (ligand/ligand-binding pair): estradiol/estrogen receptor (see, e.g., Zuo, J., et al., Plant Journal 24(2):265-273 (2000)); and rapamycin/FKPB/FKBP12 and rapamycin/FK506/FKKBP (see, e.g., Setscrew, B., et al., Nature Biotechnology 33:139-142 (2015); Chiu M. I., et al., Proceedings of the National Academy of Sciences of the United States of America 91(26):12574-12578 (1994), respectively).

Another example of a ligand moiety and ligand-binding moiety (ligand/ligand-binding pair) is to provide one or more aptamer or modified aptamer in a polynucleotide sequence of one or more polynucleotides of a dfs-NATNA (e.g., a dfs1-PN and/or a dfs2-PN) that has a high affinity and binding specificity for a selected region of the dfs-NATNA/Cas protein complex or the Cas protein thereof. Furthermore, one or more polynucleotides of a dfs-NATNA can comprise one or more aptamers or modified aptamers that has a high affinity and binding specificity for a selected region of the cognate Cas protein for the one or more polynucleotides. In one embodiment, a ligand-binding moiety can be a polynucleotide comprising an aptamer (see, e.g., Navani, N. K., et al., Biosensors and Biodetection (Methods in Molecular Biology) 504:399-415 (2009); A. V. Kulbachinskiy, Biochemistry (Moscow) 72(13):1505-1518 (2007)). Aptamers are single-stranded functional nucleic acids (ligand-binding moieties) that possess recognition capability of a corresponding ligand moiety. Typically, the aptamer is located at 5'-end or 3'-end sequences of the one or more polynucleotides of a dfs-NATNA (e.g., dfs2-PN) or a position between the 5'-end and 3'-end sequences. One example of a ligand is a dfs2-PN/dfs1-PN/Cas protein (e.g., Cas9 protein) complex. Another example of a ligand is the Cas protein (e.g., Cas9 protein), portions thereof, or modified regions of a Cas fusion protein.

In another embodiment, a ligand-binding moiety comprises a modified polynucleotide wherein a non-native functional group is introduced at positions oriented away from the hydrogen bonding face of the bases of the modified polynucleotide, such as the 5-position of pyrimidines and the 8-position of purines, see, e.g., Rohloff, J. C., et al., Molecular Therapy Nucleic Acids 3:e201 (2014)). An aptamer with high specificity and affinity for a Cas protein (e.g., Cas9 protein) can be obtained by in vitro selection and screening of an aptamer library.

In yet another embodiment, an established aptamer binding sequence/aptamer is used by introducing the aptamer-binding region into the Cas protein (e.g., Cas9 protein). For example, a biotin-binding aptamer can be introduced 5' or 3' of the DNA-binding region of a dfs2-PN and the Cas protein can be selectively biotinylated to form a corresponding binding site for the biotin-binding aptamer.

The creation of a high affinity binding site for a selected ligand on a Cas protein (e.g., Cas9) can be achieved using several protein engineering methods known to those of ordinary skill in the art in view of the guidance of the present specification. Examples of such protein engineering methods include, but are not limited to, rational protein design, directed evolution using different selection and screening methods for the library (e.g., phage display, ribosome display, yeast display, RNA display), DNA shuffling, computational methods (e.g., ROSETTA, www.rosettacommons.org/software), and introduction of a known high affinity ligand into a Cas protein. Libraries obtained by these methods can be screened to select for a Cas protein high affinity binders using, for example, a phage display assay, a cell survival assay, or a binding assay.

In some embodiments, two or more different types of affinity tags can be introduced into one or more dfs-NATNA polynucleotides, a Cas protein, a dfs2-PN, a dfs1-PN, or combinations thereof. For example, a dfs2-PN can be cross linked to a Cas protein comprising a fusion to a RNA binding protein, and a dfs1-PN can comprise the RNA binding protein binding site for the RNA binding protein. As another example, a dfs2-PN can comprise a ligand moiety, a Cas protein can comprise a ligand-binding moiety that binds a dfs2-PN ligand, and a dfs1-PN can be cross linked to the Cas protein using a photoactive cross-linking moiety. Typically, if both a dfs2-PN and a dfs1-PN are tethered to a Cas protein, the affinity tags for the dfs2-PN and the dfs1-PN are different to maintain specificity of the site to which they are each tethered on the Cas protein.

In a third aspect, the present invention relates to nucleic acid sequences encoding one or more dfs-NATNA polypeptides (e.g., comprising a dfs2-PN and a dfs1-PN), as well as expression cassettes, vectors, and recombinant cells comprising nucleic acid sequences encoding dfs-NATNAs. Some embodiments of the third aspect of the invention include a nucleic acid coding sequence for a cognate Cas protein (e.g., a Cas9 protein) with which the dfs-NATNA is capable of forming a complex. Such embodiments include, but are not limited to expression cassettes, vectors, and recombinant cells.

In one embodiment, the present invention relates to one or more expression cassettes comprising one or more nucleic acid sequences encoding one or more dfs-NATNA polynucleotides, and optionally one or more nucleic acid sequences encoding a cognate Cas protein (e.g., Cas9 protein) with which the dfs-NATNA is capable of forming a complex. Expression cassettes typically comprise a regulatory sequence involved in one or more of the following: regulation of transcription, post-transcriptional regulation, or regulation of translation. Expression cassettes can be introduced into a wide variety of organisms including, but not limited to, bacterial cells, yeast cells, plant cells, and mammalian cells. Expression cassettes typically comprise functional regulatory sequences corresponding to the organism(s) into which they are being introduced.

A further embodiment of the present invention relates to vectors, including expression vectors, comprising one or more nucleic acid sequences encoding one or more dfs-NATNA polynucleotides, and optionally one or more nucleic acid sequences encoding a cognate Cas protein (e.g., Cas9 protein) with which the dfs-NATNA is capable of forming a complex. Vectors can also include sequences encoding selectable or screenable markers. Furthermore, nuclear targeting sequences can also be added, for example, to the Cas protein. Vectors can also include polynucleotides encoding protein tags (e.g., poly-His tags, hemagglutinin tags, fluorescent protein tags, and bioluminescent tags). The coding sequences for such protein tags can be fused to, for example, one or more nucleic acid sequences encoding a Cas protein.

General methods for construction of expression vectors are known in the art. Expression vectors for host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, and viral vectors (including lentivirus, retrovirus, adenovirus, herpes simplex virus I or II, parvovirus, reticuloendotheliosis virus, and adeno-associated virus (AAV) vectors) for cell transformation and gene expression and methods to easily allow cloning of such polynucleotides. Illustrative plant transformation vectors include those derived from a Ti plasmid of *Agrobacterium tumefaciens* (Lee, L. Y., al., Plant Physiology 146(2): 325-332 (2008)). Also useful and known in the art are *Agrobacterium rhizogenes* plasmids. For example, SNAPGENE™ (GSL Biotech LLC, Chicago, Ill.; snapgene.com/resources/plasmid_files/your_time_is_valuable/) provides an extensive list of vectors, individual vector sequences, and vector maps, as well as commercial sources for many of the vectors.

Lentiviral vectors are examples of vectors useful for introduction into mammalian cells of one or more nucleic acid sequences encoding one or more dfs-NATNA polynucleotides, and optionally one or more nucleic acid sequences encoding a Cas protein (e.g., Cas9 protein) with which the dfs-NATNA is capable of forming a complex. *Lentivirus* is a member of the Retroviridae family and is a single-stranded RNA virus, which can infect both dividing and non-dividing cells as well as provide stable expression through integration into the genome. To increase the safety of lentiviral vectors, components necessary to produce a viral vector are split across multiple plasmids. Transfer vectors are typically replication incompetent and may additionally contain a deletion in the 3'LTR, which renders the virus self-inactivating after integration. Packaging and envelope plasmids are typically used in combination with a transfer vector. For example, a packaging plasmid can encode combinations of the Gag, Pol, Rev, and Tat genes. A transfer plasmid can comprise viral LTRs and the psi packaging signal. The envelope plasmid usually comprises an envelope protein (usually vesicular stomatitis virus glycoprotein, VSV-GP, because of its wide infectivity range).

Lentiviral vectors based on human immunodeficiency virus type-1 (HIV-1) have additional accessory proteins that facilitate integration in the absence of cell division. HIV-1 vectors have been designed to address a number of safety concerns, including separate expression of the viral genes in trans to prevent recombination events leading to the generation of replication-competent viruses. Furthermore, the development of self-inactivating vectors reduces the potential for transactivation of neighboring genes and allows for the incorporation of regulatory elements to target gene expression to particular cell types (see, e.g., Cooray, S., et al., Methods in Enzymology 507:29-57 (2012)).

Transformed host cells (or recombinant cells) or the progeny of cells that have been transformed or transfected using recombinant DNA techniques can comprise one or more nucleic acid sequences encoding one or more dfs-NATNA polynucleotides, and optionally one or more nucleic acid sequences encoding a Cas protein (e.g., a Cas9 protein) with which the dfs-NATNA is capable of forming a complex. Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, microprojectile bombardment, direct microinjection, and nanoparticle-mediated delivery.

As an alternative to expressing one or more nucleic acid sequences encoding one or more dfs-NATNA polynucleotides (optionally one or more nucleic acid sequences encoding a Cas protein with which the dfs-NATNA is capable of forming a complex), a dfs-NATNA, cognate Cas protein (e.g., a Cas9 protein), or a dfs-NATNA/Cas protein complex can be directly introduced into a cell. Or one or more of these nucleic acid sequences can be expressed by a cell and the other component(s) of a dfs-NATNA/Cas protein complex can be directly introduced. Methods to introduce the components into a cell include electroporation, lipofection, particle gun technology, and microprojectile bombardment.

A variety of exemplary host cells disclosed herein can be used to produce recombinant cells using a dfs-NATNA/Cas protein complex. Such host cells include, but are not limited to, a plant cell, a yeast cell, a bacterial cell, an insect cell, an algal cell, and a mammalian cell.

Methods of introducing polynucleotides (e.g., an expression vector) into host cells to produce recombinant cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, direct microinjection, and nanoparticle-mediated delivery. For ease of discussion, "transfection" is used below to refer to any method of introducing polynucleotides into a host cell.

Preferred methods for introducing polynucleotides plant cells include microprojectile bombardment and *Agrobacterium*-mediated transformation. Alternatively, other non-*Agrobacterium* species (e.g., *Rhizobium*) and other prokaryotic cells that are able to infect plant cells and introduce heterologous polynucleotides into the genome of the infected plant cell can be used. Other methods include electroporation, liposome-mediated transfection, transformation using pollen or viruses, and chemicals that increase free DNA uptake, or free DNA delivery using microprojectile bombardment (see, e.g., Narusaka, Y., et al., Chapter 9, in Transgenic Plants—Advances and Limitations, edited by Yelda, O., ISBN 978-953-51-0181-9 (2012)).

In some embodiments, a host cell is transiently or non-transiently transfected with nucleic acid sequences encoding one or more component of a dfs-NATNA/Cas protein (e.g., a Cas9 protein) complex. In some embodiments, a cell is transfected as it naturally occurs in a subject. In some embodiments, a cell that is transfected is first removed from a subject, e.g., a primary cell or progenitor cell. In some embodiments, the primary cell or progenitor cell is cultured and/or is returned after ex vivo transfection to the same subject or to a different subject.

The dfs-NATNA/Cas protein (e.g., a Cas9 protein) complexes described herein can be used to generate non-human transgenic organisms by site specifically introducing a selected polynucleotide sequence (e.g., a portion of a donor polynucleotide) at a DNA target locus in the genome to generate a modification of the genomic DNA. The transgenic organism can be an animal or a plant.

A transgenic animal is typically generated by introducing dfs-NATNA/Cas protein (e.g., a Cas9 protein) complexes (or nucleic acid coding sequences for components thereof) into a zygote cell. A basic technique, described with reference to making transgenic mice (see, e.g., Cho, A., et al., "Generation of Transgenic Mice," Current Protocols in Cell Biology, CHAPTER. Unit-19.11 (2009)) involves five basic steps: first, preparation of a system, as described herein, including a suitable donor polynucleotide; second, harvesting of donor zygotes; third, microinjection of the system into the mouse zygote; fourth, implantation of microinjected zygotes into pseudo-pregnant recipient mice; and fifth, performing genotyping and analysis of the modification of the genomic DNA established in founder mice. The founder mice will pass the genetic modification to any progeny. The founder mice are typically heterozygous for the transgene. Mating between these mice will produce mice that are homozygous for the transgene 25% of the time.

Methods for generating transgenic plants are also well known and can be applied using dfs-NATNA/Cas protein (e.g., a Cas9 protein) complexes (or nucleic acid coding sequences for components thereof). A generated transgenic plant, for example using *Agrobacterium*-mediated transformation, typically contains one transgene inserted into one chromosome. It is possible to produce a transgenic plant that is homozygous with respect to a transgene by sexually mating (i.e., selfing) an independent segregant transgenic plant containing a single transgene to itself, for example an F0 plant, to produce an F1 seed. Plants formed by germinating F1 seeds can be tested for homozygosity. Typical zygosity assays include, but are not limited to, single nucleotide polymorphism assays and thermal amplification assays that distinguish between homozygotes and heterozygotes.

As an alternative to using a system described herein for the direct transformation of a plant, transgenic plants can be formed by crossing a first plant that has been transformed with a dfs-NATNA/Cas protein complex with a second plant that has never been exposed to the complex. For example, a first plant line containing a transgene can be crossed with a second plant line to introgress the transgene into the second plant line, thus forming a second transgenic plant line.

A fourth aspect of the present invention relates to methods of using dfs-NATNA/Cas protein (e.g., a Cas9 protein) complexes (or nucleic acid coding sequences for components thereof). Embodiments of dfs-NATNA compositions are described herein, for example, in the preceding second aspect of the invention.

In one embodiment, the present invention includes a method of binding a nucleic acid sequence (e.g., DNA) comprising contacting a nucleic acid target sequence in the nucleic acid sequence (e.g., DNA) with a dfs-NATNA/Cas protein (e.g., a Cas9 protein) complex, thereby facilitating binding of the dfs-NATNA/Cas protein complex to the nucleic acid target sequence in the nucleic acid sequence. In some embodiments the nucleic acid target sequence is DNA or genomic DNA. Such methods of binding a nucleic acid target sequence can be carried out in vitro (e.g., in cultured cells), in vivo (e.g., within cells), or ex vivo (e.g., cells removed from a subject).

A variety of methods are known in the art to evaluate and/or quantitate protein-nucleic acid interactions including, but not limited to, the following: immunoprecipitation (ChIP) assays, DNA electrophoretic mobility shift assays (EMSA), DNA pull-down assays, and microplate capture and detection assays. Commercial kits, materials, and reagents are available to practice many of these methods and, for example, can be obtained from the following suppliers: Thermo Scientific (Wilmington, Del.), Signosis (Santa Clara, Calif.), Bio-Rad (Hercules, Calif.), and Promega (Madison, Wis.)). A common approach to detect protein-nucleic acid interactions is EMSA (see, e.g., Hellman L. M., et al., Nature Protocols 2(8):1849-1861 (2007)).

In another embodiment, the present invention includes a method of cutting a nucleic acid sequence (e.g., DNA) comprising contacting a nucleic acid target sequence in the nucleic acid sequence (e.g., DNA) with a dfs-NATNA/Cas protein (e.g., a Cas9 protein) complex, thereby facilitating binding of the nucleic acid/protein composition to the nucleic acid target sequence in the nucleic acid sequence The bound dfs-NATNA/Cas protein complex results in cutting the nucleic acid target sequence. In some embodiments, the nucleic acid target sequence is DNA or genomic DNA. Such methods of cutting a nucleic acid target sequence can be carried out in vitro, in vivo, or ex vivo.

Methods of cutting a nucleic acid target sequence using a dfs-NATNA/Cas protein (e.g., a Cas9 protein) complex are illustrated in FIG. 8, FIG. 11, and FIG. 12.

In yet another embodiment, the present invention includes a method of modifying a nucleic acid target sequence in a cell comprising contacting a nucleic acid target sequence in a nucleic acid sequence with a dfs-NATNA/Cas (e.g., Cas9) protein composition. The dfs-NATNA comprises a nucleic acid targeting sequence that is complementary to the nucleic acid target sequence. The dfs-NATNA/Cas protein composition cuts the nucleic acid target sequence. In some embodiments, the nucleic acid target sequence is DNA or genomic DNA. The cell will repair the cut site through cell repair mechanisms such as HDR, NHEJ, or MMEJ. Such methods of modifying a nucleic acid target sequence can be carried out in vitro, in vivo, or ex vivo. The contacting step may further comprise a donor polynucleotide being present, wherein at least a portion of the donor polynucleotide is incorporated into the DNA.

In yet another embodiment, the present invention includes methods of modulating in vitro or in vivo transcription, for example, transcription of a gene comprising regulatory element sequences. The method comprises contacting a nucleic acid target sequence (e.g., double-stranded DNA) with a dfs-NATNA/Cas protein (e.g., a Cas9 protein) complex, thereby facilitating binding of the dfs-NATNA/Cas protein complex to the nucleic acid target sequence. In some embodiments, the Cas protein is a catalytically inactive nuclease protein (e.g., a dCas9 protein). In addition, the Cas protein can be a fusion protein, for example, dCas9 fused to a repressor or activator domain. The binding of the dfs-NANTA/Cas protein complex to the nucleic acid target sequence modulates transcription of the gene.

Any of the components of the dfs-NATNA/Cas protein (e.g., a Cas9 protein) compositions, as described above, can be incorporated into a kit, optionally including one or more reagents. In some embodiments, a kit includes a package with one or more containers holding the kit elements, as one or more separate compositions or, optionally if the compatibility of the components allows, as admixture. In some embodiments, kits also comprise one or more of the following: a buffer, a buffering agent, a salt, a sterile aqueous solution, a preservative, and combinations thereof. Illustrative kits can comprise a dfs1-PN, a dfs2-PN, a dfs1-PN and a dfs2-PN, and optionally a Cas (e.g., Cas9) protein; or one or more nucleic acid sequences encoding a dfs1-PN, a dfs2-PN, a dfs1-PN and a dfs2-PN, and optionally a Cas (e.g., Cas9) protein. Alternatively, one or more nucleic acid sequences encoding a Cas (e.g., Cas9) protein can be included rather than the Cas protein.

Furthermore, kits can further comprise instructions for using components of the dfs-NATNA/Cas protein (e.g., a Cas9 protein) compositions or nucleic acid sequences encoding such components. Instructions included in kits of the invention can be affixed to packaging material or can be included as a package insert. Although the instructions are typically written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. Instructions can also include the address of an Internet site that provides the instructions.

Another aspect of the invention relates to methods of making or manufacturing a dfs-NATNA/Cas protein (e.g., a Cas9 protein) composition or components thereof. In one embodiment, a method of making or manufacturing comprises chemically synthesizing one or more components of a dfs-NATNA/Cas protein (e.g., a Cas9 protein) composition. In some embodiments, one or more polynucleotides of a dfs-NATNA comprise RNA bases and can be generated from DNA templates using in vitro transcription.

A dfs-NATNA/Cas protein (e.g., a Cas9 protein) composition can further comprise a detectable label, such as a moiety that can provide a detectable signal. Examples of detectable labels include, but are not limited to, an enzyme, a radioisotope, a member of a specific binding pair, a fluorophore (FAM), a fluorescent protein (green fluorescent protein, red fluorescent protein, mCherry, tdTomato), an DNA or RNA aptamer together with a suitable fluorophore (enhanced GFP (EGFP), "Spinach"), a quantum dot, an antibody, and the like. A large number and variety of suitable detectable labels are well-known to one of ordinary skill in the art.

A dfs-NATNA/Cas protein (e.g., a Cas9 protein) composition or cells modified through the use of a dfs-NATNA/Cas protein composition or progeny of such cells can be used as pharmaceutical compositions formulated, for example, with a pharmaceutically acceptable excipient. Illustrative excipients include carriers, stabilizers, diluents, dispersing agents, suspending agents, thickening agents, and the like. The pharmaceutical compositions can facilitate administration of a dfs-NATNA/Cas protein composition to a subject. Pharmaceutical compositions can be administered in therapeutically effective amounts by various forms and routes including, for example, intravenous, subcutaneous, intramuscular, oral., aerosol, parenteral., ophthalmic, and pulmonary administration.

The Class 2 Type II CRISPR-Cas-associated discontinuous first-stem nucleic-acid targeting nucleic acid compositions described herein (e.g., dfs-NATNA/Cas9 protein compositions) provide a number of advantages including, but not limited to, the following:

Increased binding affinity of the dfs2-PN for a nucleic acid target sequence relative to affinity of dfs2-PN to dfs1-PN, which increases the likelihood of dfs2-PN disassociating from the dfs1-PN/Cas9 protein complex and remaining bound to the nucleic acid target sequence; thus altering repair outcomes from dfs-1-PN/dfs2-PN/Cas9 protein-induced nucleic acid target sequence cleavage. (For example, a donor polynucleotide connected to a dfs2-PN (dfs-PN-donor) can be brought into proximity of a double-strand break facilitated by a dfs1-PN/dfs2-PN-donor/Cas9 protein complex and remain in proximity of the site of the double-strand break after dissociation of the dfs1-PN/Cas9 protein complex.);

Modified binding affinity of a dfs-NATNA/Cas9 protein complex for a nucleic acid target sequence;

Increased binding affinity of one or more polynucleotides of a dfs-NATNA composition (e.g., a dfs1-PN and/or a dfs2-PN) to a Cas protein (e.g., Cas9 protein) using covalent cross linking or tethering of the one or more polynucleotides of a dfs-NATNA composition to a Cas protein versus employing a dual-guide RNA or sgRNA charge-based interaction with a Cas protein;

Provision of an activatable system (e.g., when dfs2-PN or dfs1-PN comprises UV cross-linking or thiol cross-linking moieties, or the Csy4 RNA hairpin comprises a riboswitch activatable by, for example, a small molecule);

Resistance to RNase degradation provided by modified thiol-linkages of one or more polynucleotides of a dfs-NATNA composition (e.g., a dfs1-PN and/or a dfs2-PN);

Fast generation of screening, e.g., screens can be developed by creating a Csy4-dfs2-PN library and pairing each dfs2-PN of the library with the same dfs1-PN and (dCsy4)-Cas protein for screening; and Improved cell delivery of dfs2-PNs into cells expressing dfs1-PNs and Cas protein versus delivery of a similarly targeted crRNA into cells expressing tracrRNA and Cas protein, due to the smaller size of the dfs2-PNs.

EXPERIMENTAL

Aspects of the present invention are illustrated in the following Examples. Efforts have been made to ensure accuracy with respect to numbers used (e.g., amounts, concentrations, percent changes, and the like) but some experimental errors and deviations should be accounted for. Unless indicated otherwise, temperature is in degrees Centigrade and pressure is at or near atmospheric. It should be understood that these Examples are given by way of illustration only and are not intended to limit the scope of what the inventors regard as various aspects of the present invention.

Example 1

Component Production of Discontinuous First-Stem Nucleic-Acid Targeting Nucleic Acids This Example describes production of polynucleotide components of engineered Class 2 Type II CRISPR-Cas9-associated discontinuous first-stem nucleic-acid targeting nucleic acid (dfs-NATNA) compositions, for example, as illustrated in FIG. 3A and FIG. 3B. Components of the dfs-NATNA compositions were assembled by PCR using 3' overlapping primers containing DNA sequences corresponding to each dfs-NATNA component.

In these dfs-NATNA compositions, the lower stem nucleotide sequence II comprised, in a 5' to 3' direction: a fragment nucleotide sequence 2 comprising at least one nucleotide and the 3' terminus of the dfs2-PN, and a fragment nucleotide sequence 1 comprising the 5' terminus of the dfs1-PN and at least one nucleotide; wherein the lower stem element nucleotide sequence I and the lower stem element nucleotide sequence II formed a stem element comprising at least 2 pairs of hydrogen-bonded nucleotides (see FIG. 3A, FIG. 3B, and Table 1).

A. Production of dfs1-PN Components

Several first Class 2 Type II CRISPR-Cas9-associated discontinuous first-stem polynucleotides (dfs1-PNs), for example, dfs1-PNs as illustrated in FIG. 3A, 300, and FIG. 3B, 300, were produced as follows.

The dfs1-PNs, comprising RNA (dfs1-RNA), each comprised a fragment nucleotide sequence 1 comprising, in a 5' to 3' direction, the 5' terminus of the dfs1-PN and a nucleotide sequence, wherein each dfs1-RNA has a nucleotide sequence of a different length. In each of these dfs1-RNAs, the lower stem element nucleotide sequence II is discontinuous.

RNA components were produced by in vitro transcription (e.g., T7 Quick High Yield RNA Synthesis Kit; New England Biolabs, Ipswich, Mass.) from a double-stranded DNA template incorporating a T7 promoter at the 5'-end sequences of the DNA.

The double-stranded DNA template for each dfs1-RNA (e.g., dfs1-RNA$_1$) component was assembled by PCR using 3' overlapping primers containing DNA sequences corresponding to the dfs1-RNA component. The oligonucleotides used in the assembly are presented in Table 8.

TABLE 8

Overlapping Primers for Generation of dfs1-RNA-encoding Templates

| dfs1-RNA | Overlapping primers |
| --- | --- |
| dfs1-RNA$_1$ | SEQ ID NO. 1, 3, 4, 2 |
| dfs1-RNA$_2$ | SEQ ID NO. 1, 5, 6, 2 |
| dfs1-RNA$_3$ | SEQ ID NO. 1, 7, 8, 2 |
| dfs1-RNA$_4$ | SEQ ID NO. 1, 9, 10, 2 |

The DNA primers were present at a concentration of 2 nM each. One DNA primer corresponded to the T7 promoter (SEQ ID NO. 1) and the other to the 3' terminus of the RNA sequence (SEQ ID NO. 2). The DNA primers were used at a concentration of 640 nM to drive the amplification reaction. PCR reactions were performed using Q5 Hot Start High-Fidelity 2× Master Mix (New England Biolabs, Ipswich, Mass.) following the manufacturer's instructions. PCR assembly reactions were carried out using the following thermal cycling conditions: 98° C. for 2 minutes, 35 cycles of 15 seconds at 98° C., 15 seconds at 60° C., 15 seconds at 72° C., and a final extension at 72° C. for 2 minutes. DNA product quality was evaluated after the PCR reaction by agarose gel electrophoresis (1.5%, SYBR® Safe; Life Technologies, Grand Island, N.Y.).

Between 0.25-0.5 μg of the DNA template for each dfs1-RNA component was used as a template for transcription using T7 High Yield RNA Synthesis Kit (New England Biolabs, Ipswich, Mass.) for approximately 16 hours at 37° C. Transcription reactions were treated with DNase I (New England Biolabs, Ipswich, Mass.) and purified using GeneJet RNA Cleanup and Concentration Kit (Life Technologies, Grand Island, N.Y.). RNA yield was quantified using the Nanodrop™ 2000 System (Thermo Scientific, Wilmington, Del.). The quality of the transcribed RNA was checked by agarose gel electrophoresis (2%, SYBR® Safe; Life Technologies, Grand Island, N.Y.). The dfs1-RNA sequences are shown in Table 9.

TABLE 9

| SEQ ID NO. | Name | Length | Sequence |
| --- | --- | --- | --- |
| SEQ ID NO. 17 | dfs1-RNA$_1$ | 97 | GCUCAGAGCUAUGCUGUCCUGAAAGCAGG ACAGCAUAGCAAGUUGAGCUAAGGCUAGU CCGUUAUCAACUUGAAAAAGUGGCACCGA GUCGGUGCUU |
| SEQ ID NO. 18 | dfs1-RNA$_2$ | 96 | GUCAGAGCUAUGCUGUCCUGAAAGCAGGA CAGCAUAGCAAGUUGACAUAAGGCUAGUC CGUUAUCAACUUGAAAAAGUGGCACCGAG UCGGUGCUU |
| SEQ ID NO. 19 | dfs1-RNA$_3$ | 95 | GCAGAGCUAUGCUGUCCUGAAAGCAGGAC AGCAUAGCAAGUUGCGAUAAGGCUAGUCC GUUAUCAACUUGAAAAAGUGGCACCGAGU CGGUGCUU |
| SEQ ID NO. 20 | dfs1-RNA$_4$ | 94 | GAGAGCUAUGCUGUCCUGAAAGCAGGACA GCAUAGCAAGUUCAGAUAAGGCUAGUCCG UUAUCAACUUGAAAAAGUGGCACCGAGUC GGUGCUU |

This method for production of dfs1-RNAs can be applied to the production of other dfs-NATNAs described herein.

B. Production of dfs2-PN Components

Several second Class 2 Type II CRISPR-Cas9-associated discontinuous first-stem single-strand polynucleotides (dfs2-PNs), for example, dfs2-PNs as illustrated in FIG. 3A, 301, and FIG. 3B, 301, were produced as follows.

The dfs2-PNs, comprising RNA (dfs2-RNA), each comprised a fragment nucleotide sequence 2 comprising, in a 5' to 3' direction, a nucleotide sequence and the 3' terminus of the dfs2-PN, wherein each dfs2-RNA has a nucleotide sequence of a different length. In each of these dfs2-RNAs, the lower stem element nucleotide sequence II is discontinuous.

The dfs2-RNAs were designed to comprise a DNA target binding sequence targeting the adeno-associated virus integration site 1 (AAVS-1) from the human genome. The DNA target sequence selected for targeting is shown in Table 10.

TABLE 10

AAVS-1 Target Sequences

| SEQ ID NO. | Sequence | hg38 co-ordinates |
| --- | --- | --- |
| SEQ ID NO. 21 | GGGGCCACTAGGGACAGGAT | chr19: 55627120-55627139 |

Four dfs2-RNAs were engineered to incorporate a nucleic acid target binding sequence corresponding to the DNA target sequence. The RNA sequences for the dfs2-RNAs were provided to a commercial manufacturer for synthesis. The sequences of the dfs2-RNAs are shown in Table 11.

TABLE 11 dfs2-RNA Sequences

| SEQ ID NO. | Name | Length | Sequence* |
| --- | --- | --- | --- |
| SEQ ID NO. 11 | dfs2-RNA$_1$ | 21 | GGGGCCACUAGGGACAGGAUG |
| SEQ ID NO. 12 | dfs2-RNA$_2$ | 22 | GGGGCCACUAGGGACAGGAUGU |
| SEQ ID NO. 13 | dfs2-RNA$_3$ | 23 | GGGGCCACUAGGGACAGGAUGUC |
| SEQ ID NO. 14 | dfs2-RNA$_4$ | 24 | GGGGCCACUAGGGACAGGAUGUCU |

*AAVS-1 target sequence is underlined

This method for the design of dfs2-RNAs can be applied to the design of other dfs2-RNAs as described herein. Alternatively, dfs2-RNAs can be produced by in vitro transcription in a manner similar to the method described above.

Example 2

Production of Double-Stranded DNA Target Sequences for Use in Cleavage Assays

Double-stranded DNA target sequences for use in in vitro Cas protein cleavage assays were produced using PCR amplification of selected nucleic acid target sequences from genomic human DNA.

Double-stranded DNA target sequences for genomic human DNA Adeno-associated virus integration site 1 (AAVS-1) for biochemical assays were amplified by PCR by phenol-chloroform preparation from human cell line K562 (American Type Culture Collection (ATCC), Manassas, Va.) genomic DNA (gDNA). PCR reactions were carried out with Q5 Hot Start High-Fidelity 2× Master Mix (New England Biolabs, Ipswich, Mass.) following the manufacturer's instructions. 20 ng/μL gDNA in a final volume of 25 μl were used to amplify the selected nucleic acid target sequence under the following conditions: 98° C. for 2 minutes, 35 cycles of 20 seconds at 98° C., 20 seconds at 60° C., 20 seconds at 72° C., and a final extension at 72° C. for 2 minutes. PCR products were purified using Spin Smart™ PCR purification tubes (Denville Scientific, South Plainfield, N.J.) and quantified using a Nanodrop™ 2000 UV-Vis spectrophotometer (Thermo Scientific, Wilmington, Del.).

The forward and reverse primers used for amplification of the selected DNA target sequences from gDNA are presented in Table 12.

TABLE 12

Double-stranded DNA Target Sequence Primer Sequences

| SEQ ID NO. | Sequence |
|---|---|
| SEQ ID NO. 15 | CCCCGTTCTCCTGTGGATTC |
| SEQ ID NO. 16 | ATCCTCTCTGGCTCCATCGT |

The AAVS-1 DNA target sequences were amplified using SEQ ID NO. 15 and SEQ ID NO. 16, yielding a 495 bp double-stranded DNA target sequence.

Other suitable double-stranded DNA target sequences can be obtained using essentially the same method. For non-human nucleic acid target sequences, genomic DNA from the selected organism (e.g., plant, bacteria, yeast, algae, and the like) can be used instead of DNA derived from human cells. Furthermore, polynucleotide sources other than genomic DNA can be used (e.g., vectors and gel isolated DNA fragments).

Example 3

Cas Cleavage Assays

This Example illustrates the use of dfs-NATNA/Cas9 protein complexes in cleavage assays. dfs2-PN/dfs1-PN/Cas9 protein complexes were used in in vitro Cas9 cleavage assays to evaluate and compare the percent cleavage of selected dfs2-PN/dfs1-PN/Cas9 protein complexes relative to selected double-stranded DNA target sequences set forth in Example 2.

S. pyogenes Cas9 was recombinantly expressed in E. coli and purified for use in an in vitro biochemical cleavage assay.

Corresponding pairs of dfs2-RNA/dfs1-RNA components (as produced in Example 1B (dfs2-$RNA_1$) and Example 1A (dfs1-$RNA_1$)) were diluted to a suitable working concentration, assembled in a single tube to a final concentration of 500 nM each, incubated in a thermocycler for 2 minutes at 95° C., removed from the thermocycler, and allowed to equilibrate to room temperature. The corresponding dfs2-RNA/dfs1-RNA pairs are shown in Table 13.

TABLE 13

Biochemical Cleavage of DNA Target Sequences with dfs2-RNA/dfs1-RNA/Cas9 Protein Complexes

| dfs-NATNAs | Number of lower stem base-pair interactions | SEQ ID NOs. |
|---|---|---|
| dfs2-RNA-1/dfs1-$RNA_1$ | 1 | SEQ ID NO. 17/ SEQ ID NO. 11 |
| dfs2-RNA-2/dfs1-$RNA_2$ | 2 | SEQ ID NO. 18/ SEQ ID NO. 12 |
| dfs2-RNA-3/dfs1-$RNA_3$ | 3 | SEQ ID NO. 19/ SEQ ID NO. 13 |
| dfs2-RNA-4/dfs1-$RNA_4$ | 4 | SEQ ID NO. 20/ SEQ ID NO. 14 | dfs2-RNA and dfs1-RNA pairs were added to a Cas9 reaction mix. The Cas9 reaction mix comprised Cas9 protein diluted to a final concentration of 200 nM in reaction buffer (20 mM HEPES, 100 mM KCl, 5 mM $MgCl_2$, 1 mM DTT, and 5% glycerol at pH 7.4). Each reaction mix was incubated at 37° C. for 10 minutes. The cleavage reaction was initiated by the addition of the DNA target sequence to a final concentration of 15 nM. Samples were mixed and centrifuged briefly before being incubated for 15 minutes at 37° C. Cleavage reactions were terminated by the addition of Proteinase K (Denville Scientific, South Plainfield, N.J.) at a final concentration of 0.2 µg/µL and 0.44 mg/µL RNase A Solution (SigmaAldrich, St. Louis, Mo.). Samples were then incubated for 25 minutes at 37° C. and 25 minutes at 55° C. For each sample, 12 µL of the total reaction were evaluated for cleavage activity by agarose gel electrophoresis (2%, SYBR® Gold; Life Technologies, Grand Island, N.Y.). For the Cas9 cleavage of the AAVS-1 double-stranded DNA target sequence, the appearance of DNA bands at approximately 316 bp and approximately 189 bp indicated that cleavage of the DNA target sequence had occurred. Cleavage percentages were calculated using area under the curve (AUC) values as calculated by FIJI (ImageJ; an open source Java image processing program) for each cleavage fragment and the parent DNA target sequence, and then dividing the sum of the cleavage fragments by the sum of both the cleavage fragments and the parent DNA target sequences.

Table 14 presents the results of the Cas9 cleavage assays using AAVS-1 double-stranded DNA target sequences.

TABLE 14

Biochemical Cleavage of DNA Target Sequence with dfs2-RNA/dfs1-RNA/Cas9 Protein Complexes

| dfs-NATNAs | Percent cleavage |
|---|---|
| dfs2-$RNA_1$/dfs1-$RNA_1$ | L.O.D.* |
| dfs2-$RNA_2$/dfs1-$RNA_2$ | 1.3% |
| dfs2-$RNA_3$/dfs1-$RNA_3$ | 6.9% |
| dfs2-$RNA_4$/dfs1-$RNA_4$ | 34.6% |

*L.O.D. indicates cleavage values below the limit of detection

The data presented in Table 14 demonstrate that the dfs-NATNAs of the present invention facilitated Cas protein mediated site-specific cleavage of double-stranded DNA target sequences.

Following the guidance of the present specification and Examples, the biochemical cleavage assay described in this Example can be practiced by one of ordinary skill in the art with other dfs-NATNAs and their cognate Cas9 proteins.

Example 4

Deep Sequencing Analysis for Detection of Nucleic Acid Target Sequence Modifications in Eukaryotic Cells This Example illustrates how one of ordinary skill in the art can use deep sequencing analysis to evaluate and compare the percent cleavage in cells of dfs-NATNA/Cas protein complexes relative to selected double-stranded DNA target sequences.

A. dfs-NATNA (dfs2-RNA/dfs1-RNA Pairs) RNA for Sequence Specific modification of nucleic acid target sequences in the human genomic DNA dfs2-RNA/dfs1-RNA to target the human AAVS-1 genomic DNA target can be produced as described in Example 1.

RNA sequences for exemplary dfs1-RNA and dfs2-RNA are shown in Table 9 and Table 11, respectively.

Following the guidance of the present specification and Examples, additional dfs-NATNAs can be designed by one of ordinary skill in the art.

B. Formation of dfs2-RNA/dfs1-RNA/Cas9 Protein Complexes

S. pyogenes Cas9 is tagged at the C-terminus with two nuclear localization sequences (NLS), and can be recombinantly expressed in E. coli and purified using chromatographic methods. Ribonucleoprotein complexes can be formed at a concentration of 40 pmol Cas9 protein:120 pmol dfs2-RNA/dfs1-RNA. Prior to assembly with Cas9, each of the 120 pmol dfs2-RNA and 120 pmol dfs1-RNA can be diluted to the desired total concentration (120 pmol) in a final volume of 2 µL, incubated for 2 minutes at 95° C., removed from a thermocycler, and allowed to equilibrate to room temperature. Cas9 protein can be diluted to an appropriate concentration in binding buffer (20 mM HEPES, 100 mM KCl, 5 mM $MgCl_2$, 1 mM DTT, and 5% glycerol at pH 7.4) to a final volume of 3 µL and mixed with the 2 µL of dfs2-RNA/dfs1-RNA followed by incubation at 37° C. for 30 minutes.

C. Cell Transfections Using dfs2-RNA/dfs1-RNA/Cas9 dfs2-RNA/dfs1-RNA/Cas9 protein complexes can be transfected into HEK293 cells (ATCC, Manassas Va.), using the Nucleofector® 96-well Shuttle System (Lonza, Allendale, N.J.) and the following protocol: The complexes can be dispensed in a 5 µL final volume into individual wells of a 96-well plate. The cell culture medium can be removed from the HEK293 cell culture plate and the cells detached with TrypLE™ (Thermo Scientific, Wilmington, Del.). Suspended HEK293 cells can be pelleted by centrifugation for 3 minutes at 200×g, TrypLE reagents aspirated, and cells washed with calcium and magnesium-free phosphate buffered saline (PBS). Cells can be pelleted by centrifugation for 3 minutes at 200×g, the PBS aspirated, and the cell pellet re-suspended in 10 mL of calcium and magnesium-free PBS.

The cells can be counted using the Countess® II Automated Cell Counter (Life Technologies; Grand Island, N.Y.). $2.2 \times 10^7$ cells can be transferred to a 1.5 ml microfuge tube and pelleted. The PBS can be aspirated and the cells re-suspended in Nucleofector™ SF (Lonza, Allendale, N.J.) solution to a density of $1 \times 10^7$ cells/m. 20 µL of the cell suspension can be then added to each individual well containing 5 µL of ribonucleoprotein complexes, and the entire volume from each well can be transferred to a well of a 96-well Nucleocuvette™ Plate (Lonza, Allendale, N.J.). The plate can be loaded onto the Nucleofector™ 96-well Shuttle™ (Lonza, Allendale, N.J.) and cells nucleofected using the 96-CM-130 Nucleofector™ program (Lonza, Allendale, N.J.). Post-nucleofection, 70 µL Dulbecco's Modified Eagle Medium (DMEM; Thermo Fisher Scientific, Wilmington, Del.), supplemented with 10% Fetal Bovine Serum (FBS; Thermo Scientific, Wilmington, Del.), penicillin and streptomycin (Life Technologies, Grand Island, N.Y.) can be added to each well, and 50 µL of the cell suspension can be transferred to a 96-well cell culture plate containing 150 µL pre-warmed DMEM complete culture medium. The plate can be transferred to a tissue culture incubator and maintained at 37° C. in 5% $CO_2$ for 48 hours.

D. Double-Stranded DNA Target Sequence Generation for Deep Sequencing gDNA can be isolated from the HEK293 cells 48 hours after transfection using the complexes and 50 µL QuickExtract DNA Extraction solution (Epicentre, Madison, Wis.) per well, followed by incubation at 37° C. for 10 minutes, 65° C. for 6 minutes and 95° C. for 3 minutes to stop the reaction. The isolated gDNA can be diluted with 50 µL sterile water and samples are stored at −80° C.

Using the isolated gDNA, a first PCR can be performed using Q5 Hot Start High-Fidelity 2× Master Mix (New England Biolabs, Ipswich, Mass.) at 1× concentration, primers at 0.5 µM each (SEQ ID NO. 22 and SEQ ID NO. 23), 3.75 µL of gDNA in a final volume of 10 µL and amplification at 98° C. for 1 minute, 35 cycles of 10 s at 98° C., 20 seconds at 60° C., 30 seconds at 72° C., and a final extension at 72° C. for 2 minutes. Primers can be designed to amplify the region of the genome targeted by the dfs-NATNA. The PCR reaction can be diluted 1:100 in water.

A unique set of index primers for a "barcoding" PCR can be used to facilitate multiplex sequencing for each sample. Exemplary primer pairs are shown in Table 15.

TABLE 15

Exemplary Barcoding Primers

| ID | Sample | Primers |
|---|---|---|
| BARCODING PRIMER set-1 | dfs2-$RNA_1$/dfs1-$PN_1$ | SEQ ID NO. 24, 25 |
| BARCODING PRIMER set-2 | dfs2-$RNA_2$/dfs1-$PN_2$ | SEQ ID NO. 24, 26 |
| BARCODING PRIMER set-3 | dfs2-$RNA_3$/dfs1-$PN_3$ | SEQ ID NO. 24, 27 |
| BARCODING PRIMER set-4 | dfs2-$RNA_4$/dfs1-$PN_4$ | SEQ ID NO. 24, 28 |

Barcoding PCR can be performed using a reaction mix comprising Q5 Hot Start High-Fidelity 2× Master Mix (New England Biolabs, Ipswich, Mass.) at 1× concentration, primers at 0.5 µM each (Table 15), and 1 µL of 1:100 diluted first PCR in a final volume of 10 µL. The reaction mix can be amplified as follows: 98° C. for 1 minute; followed 12 cycles of 10 s at 98° C., 20 seconds at 60° C., and 30 seconds at 72° C.; with a final extension reaction at 72° C. for 2 minutes.

E. SPRIselect Clean-Up

The PCR reactions can be pooled and transferred into a single microfuge tube for SPRIselect (Beckman Coulter, Pasadena, Calif.) bead-based cleanup of amplicons for sequencing.

To the amplicon, 0.9× volumes of SPRIselect beads can be added, mixed, and incubated at room temperature for 10 minutes. The microfuge tube can be placed on magnetic tube stand (Beckman Coulter, Pasadena, Calif.) until the solution clears. Supernatant can be removed and discarded, and the residual beads washed with 1 volume of 85% ethanol, and incubated at room temperature for 30 seconds. After incubation, ethanol can be aspirated and beads air dried at room temperature for 10 minutes. The microfuge tube can be removed from the magnetic stand and 0.25× volumes of Qiagen EB buffer (Qiagen, Venlo, Netherlands) added to the beads, mixed vigorously, and incubated for 2 minutes at room temperature. The microfuge tube can be returned to the magnet, incubated until the solution has cleared, and supernatant containing the purified amplicons dispensed into a clean microfuge tube. The purified amplicon can be quantified using the Nanodrop™ 2000 System (Thermo Scientific, Wilmington Del.) and library quality analyzed using the Fragment Analyzer™ System (Advanced Analytical Technologies, Ames, Iowa) and the DNF-910 Double-stranded DNA Reagent Kit (Advanced Analytical Technologies, Ames, Iowa).

F. Deep Sequencing Set-Up

The pooled amplicons can be normalized to a 4 nM concentration as calculated from the Nanodrop™ 2000 System values and the average size of the amplicons. The library can be analyzed on MiSeq Sequencer (Illumina, San Diego, Calif.) with MiSeq Reagent Kit v2 (Illumina, San Diego, Calif.) for 300 cycles with two 151-cycle paired-end runs plus two 8-cycle index reads.

G. Deep Sequencing Data Analysis

The identities of products in the sequencing data can be determined based on the index barcode sequences adapted onto the amplicons in the barcoding PCR. A computational script can be used to process the MiSeq data that executes, for example, the following tasks:

Reads can be aligned to the human genome (build GRCh38/38) using Bowtie (bowtie-bio.sourceforge.net/index.shtml) software.

Aligned reads can be compared to the expected wild-type AAVS-1 locus sequence, and reads not aligning to any part of the AAVS-1 locus discarded.

Reads matching wild-type AAVS-1 sequence can be tallied.

Reads with indels (insertion or deletion of bases) can be categorized by indel type and tallied.

Total indel reads can be divided by the sum of wild-type reads and indel reads to give percent-mutated reads.

Through the identification of indel sequences at regions targeted by the AAVS-1-dfs-NATNAs/Cas9 protein ribonucleoprotein complexes, sequence-specific targeting in a human cell line can be determined.

Following the guidance of the present specification and Examples, the in cell editing of a genomic sequence can be practiced by one of ordinary skill in the art with other Cas9 proteins and their cognate dfs-NATNAs.

Example 5

Identification and Screening of crRNAs

This Example describes a method to identify Class 2 crRNAs in different bacterial species. The method presented here is adapted from Chylinski, K., et al., RNA Biology 10(5):726-737 (2013). Not all of the following steps are required for screening nor must the order of the steps be as presented.

A. Identify a Species Containing a Class 2 CRISPR Locus

Using the Basic Local Alignment Search Tool (BLAST, blast.ncbi.nlm.nih.gov/Blast.cgi), a search of the genomes of various species can be conducted to identify Class 2 CRISPR Cas nucleases (e.g., Cas9 proteins). Class 2 CRISPR systems exhibit a high diversity in sequence across species; however Class 2 CRISPR nuclease orthologs have conserved domains, for example, an HNH endonuclease domain and/or a RuvC./RNase H domain. Primary BLAST results can be filtered for identified domains, incomplete or truncated sequences discarded, and species having Class 2 CRISPR nuclease orthologs identified.

If a Class 2 CRISPR nuclease ortholog is identified in a species, sequences adjacent to the Cas protein ortholog coding sequence (e.g., a Cas9 protein) can be probed for other Cas proteins and an associated repeat-spacer array to identify all sequences belonging to the CRISPR-Cas locus can be used. This may be done by alignment to other known Class 2 CRISPR loci.

Once the sequence of the Class 2 CRISPR locus for the nuclease ortholog is identified for the species, in silico predictive screening can be used to extract the crRNA sequence. The crRNA sequence is contained within CRISPR repeat array and can be identified by its hallmark repeating sequences interspaced by foreign spacer sequences.

B. Preparation of RNA-Seq Library

The putative CRISPR array containing the individual crRNA identified in silico can be further validated using RNA sequencing (RNA-seq).

Cells from species identified as comprising putative crRNA can be procured from a commercial repository (e.g., ATCC, Manassas, Va.; German Collection of Microorganisms and Cell Cultures GmbH (DSMZ), Braunschweig, Germany).

Cells can be grown to mid-log phase and total RNA prepped using Trizol reagent (SigmaAldrich, St. Louis, Mo.) and treated with DNaseI (Fermentas, Vilnius, Lithuania).

10 µg of the total RNA can be treated with Ribo-Zero rRNA Removal Kit (Illumina, San Diego, Calif.) and the remaining RNA purified using RNA Clean and Concentrators (Zymo Research, Irvine, Calif.).

A library can be prepared using a TruSeq Small RNA Library Preparation Kit (Illumina, San Diego, Calif.), following the manufacturer's instructions. This will result in cDNAs having adapter sequences.

The resulting cDNA library can be sequenced using MiSeq Sequencer (Illumina, San Diego, Calif.).

C. Processing of Sequencing Data

Sequencing reads of the cDNA library can be processed, for example, using the following method.

Adapter sequences can be removed using cutadapt 1.1 (pypi.python.org/pypi/cutadapt/1.1) and about 15 nt trimmed from the 3' end of the read to improve read quality.

Reads can be aligned to the genome of the respective species (i.e., from which the putative crRNA is to be identified) using Bowtie 2 (http://bowtie-bio.sourceforge.net/bowtie2/index.shtml). The Sequence Alignment/Map (SAM) file, which is generated by Bowtie 2, can be converted into a Binary Alignment/Map (BAM) file using SAMTools (http://samtools.sourceforge.net/) for subsequent sequencing analysis steps.

Read coverage mapping to the CRISPR locus or loci can be calculated from the BAM file using BedTools (bedtools.readthedocs.org/en/latest/).

The BED file, as generated in the previous step, can be loaded into Integrative Genomics Viewer (IGV; www.broadinstitute.org/igv/) to visualize the sequencing read pileup. Read pile can be used to identify the 5' and 3' termini of the transcribed putative crRNA sequence.

The RNA-seq data can be used to validate that a putative crRNA element is actively transcribed in vivo. Confirmed hits from comparison of the in silico and RNA-seq screens can be validated for functional ability to support Class 2 CRISPR nuclease cleavage of double-stranded DNA target nucleic acid sequences using the methods outline herein (e.g., Examples 1, 2, and 3).

Following the guidance of the present specification and Examples, the identification of novel crRNA sequences associated with Cas9 proteins can be practiced by one of ordinary skill in the art.

Example 6

Identification and Screening of tracrRNAs

This Example illustrates a method by which tracrRNAs of species having, for example, a Class 2 Type II CRISPR-Cas9 system can be identified. This is adapted from Chylinski, K., et al., RNA Biology 10(5):726-737 (2013). Not all of the following steps are required for screening nor must the order of the steps be as presented.

A. Identification of a Species Containing a Type II CRISPR-Cas9 System

Using the Basic Local Alignment Search Tool (BLAST, blast.ncbi.nlm.nih.gov/Blast.cgi), a search of the genomes of various species can be conducted to identify a Cas9 protein. Class 2 Type II CRISPR-Cas9 systems exhibit a high diversity in sequence across species, however Cas9 orthologs exhibit conserved domain architectures of a central HNH endonuclease domain and a split RuvC./RNase domain. Primary BLAST results can be filtered for identified domains; incomplete or truncated sequences discarded and Cas9 orthologs identified.

If a Cas9 ortholog is identified in a species, sequences adjacent to the Cas9 ortholog-coding sequence can be probed for other Cas proteins and a Cas-associated repeat-spacer array to identify all sequences belonging to the CRISPR-Cas9 locus. This may be done by alignment to other known Class 2 Type II CRISPR-Cas9 loci, with the knowledge that closely related species exhibit similar CRISPR-Cas9 locus architecture (e.g., Cas protein composition, size, orientation, location of array, location of tracrRNA, and the like). The tracrRNA element is typically contained within the Class 2 Type II CRISPR-Cas9 locus and can be readily identified by its sequence complementarity to the repeat elements in the repeat-spacer array. It should be noted that the tracrRNA sequences complementary to the repeat elements are called the tracrRNA "anti-repeat sequences."

Once the sequence of the CRISPR-Cas9 locus corresponding to the Cas9 ortholog is identified for a species, in silico predictive screening can be used to extract the tracr anti-repeat sequence to identify the associated tracrRNA. Putative anti-repeats can be screened, for example, as follows.

If the repeat sequence is from a known species, the repeat sequence can be identified in, and retrieved from, the CRISPRdb database (crispr.u-psud.fr/crispr/). If the repeat sequence is not from a known species, the repeat sequence can be predicted employing CRISPRfinder software (crispr.u-psud.fr/Server/) using the Class 2 Type II CRISPR-Cas9 locus for the species, as described above.

The identified repeat sequence for the species can be used to probe the CRISPR-Cas9 locus for the anti-repeat sequence (e.g., using the BLASTp algorithm or the like). The search is typically restricted to intergenic regions of the CRISPR-Cas9 locus.

An identified tracr anti-repeat region can be validated for complementarity to the identified repeat sequence.

A putative anti-repeat region can be analyzed in the regions 5' and 3' of the putative anti-repeat region for a Rho-independent transcriptional terminator (TransTerm HP, transterm.cbcb.umd.edu/).

By combining the identified sequence comprising the anti-repeat element and the Rho-independent transcriptional terminator, the sequence can be determined to be the putative tracrRNA of the given species.

B. Preparation of RNA-Seq Library

The in silico identified, putative tracrRNA can be further validated using RNA sequencing (RNA-seq).

Cells from species comprising the putative tracrRNA can be procured from a commercial repository (e.g., ATCC, Manassas Va.; DSMZ, Braunschweig, Germany).

Cells can be grown to mid-log phase and total RNA prepared using Trizol reagent (SigmaAldrich, St. Louis, Mo.) and treated with DNaseI (Fermentas, Vilnius, Lithuania).

10 μg of the total RNA can be treated using a Ribo-Zero rRNA Removal Kit (Illumina, San Diego, Calif.) and the remaining RNA purified using RNA Clean and Concentrators (Zymo Research, Irvine, Calif.).

A library can be prepared using a TruSeq Small RNA Library Preparation Kit (Illumina, San Diego, Calif.) following the manufacturer's instructions. This will result in cDNAs having adapter sequences.

The resulting cDNA library can be sequenced using a MiSeq Sequencer (Illumina, San Diego, Calif.).

C. Processing of Sequencing Data

Sequencing reads of the cDNA library can be processed, for example, using the following method.

Adapter sequences can be removed using cutadapt 1.1 (pypi.python.org/pypi/cutadapt/1.1) and about 15 nt trimmed from the 3' end of the read to improve read quality.

Reads can be aligned to the genome of the respective species (i.e., from which the putative crRNA is identified) using Bowtie 2 (http://bowtie-bio.sourceforge.net/bowtie2/index.shtml). The Sequence Alignment/Map (SAM) file, generated by Bowtie 2, can be converted into a Binary Alignment/Map (BAM) file using SAMTools (http://samtools.sourceforge.net/) for subsequent sequencing analysis steps.

Read coverage mapping to the CRISPR locus or loci can be calculated from the BAM file using BedTools (bedtools.readthedocs.org/en/latest/).

The BED file, generated in the previous step, can be loaded into Integrative Genomics Viewer (IGV; www.broadinstitute.org/igv/) to visualize the sequencing read pileup. Read pile can be used to identify the 5' and 3' termini of the transcribed putative tracrRNA sequence.

The RNA-seq data can be used to validate that a putative tracrRNA element is actively transcribed in vivo. Confirmed hits from the comparison of the in silico and RNA-seq screens can be validated for functional ability of the identified tracrRNA sequence and its cognate crRNA to support Cas9-mediated cleavage of a double-stranded DNA target sequence using methods outline herein (e.g., Examples 1, 2, and 3).

Following the guidance of the present specification and Examples, the identification of novel tracrRNA sequences related to Cas9 proteins can be accomplished by one of ordinary skill in the art.

Example 7

T7E1 Assay for Detection of Nucleic Acid Target Sequence Modifications in Eukaryotic Cells This Example illustrates the use of T7E1 assays to evaluate and compare the percent cleavage in vivo of dfs-NATNA/Cas9 protein complexes relative to selected double-stranded DNA target sequences.

A. Cell Transfections Using Cas Polynucleotide Components

The dfs-NATNAs can be transfected into HEK293 cells constitutively expressing *S. pyogenes* Cas9 using the Nucleofector® 96-well Shuttle System (Lonza, Allendale, N.J.) and the following protocol. dfs2-PN/dfs1-PN pairs can be diluted to appropriate concentration (e.g., 120 pmol) and incubated for 2 minutes at 95° C., removed from a thermocycler, allowed to equilibrate to room temperature, and dispensed in a 5 µL final volume in a 96-well plate. Culture medium can be aspirated from HEK293-Cas9 cells, the cells washed once with calcium and magnesium-free PBS, and trypsinized by the addition of TrypLE (Life Technologies, Grand Island, N.Y.), followed by incubation at 37° C. for 3-5 minutes. Trypsinized cells can be gently pipetted up and down to form a single-cell suspension and added to DMEM complete culture medium composed of DMEM culture medium (Life Technologies, Grand Island, N.Y.) containing 10% Fetal Bovine Serum (FBS; Thermo Scientific, Wilmington, Del.) and supplemented with penicillin and streptomycin (Life Technologies, Grand Island, N.Y.).

The cells can be then pelleted by centrifugation for 3 minutes at 200×g, the culture medium aspirated, and cells re-suspended in PBS. The cells can be counted using the Countess® II Automated Cell Counter (Life Technologies, Grand Island, N.Y.). $2.2 \times 10^7$ cells can be transferred to a 1.5 ml microfuge tube and pelleted. The PBS can be aspirated and the cells re-suspended in Nucleofector™ SF (Lonza, Allendale, N.J.) solution to a density of $1 \times 10^7$ cells/mL. 20 µL of the cell suspension can be added to individual wells containing 5 uL of the dfs2-PN/dfs1-PN and the entire volume transferred to the wells of a 96-well Nucleocuvette™ Plate (Lonza, Allendale, N.J.). The plate can be loaded onto the Nucleofector™ 96-well Shuttle™ (Lonza, Allendale, N.J.) and cells nucleofected using the 96-CM-130 Nucleofector™ program (Lonza, Allendale, N.J.). Post-nucleofection, 70 µL DMEM complete culture medium can be added to each well, and 50 µL of the cell suspension transferred to a collagen-coated 96-well cell culture plate containing 150 µl pre-warmed DMEM complete culture medium. The plate can be transferred to a tissue culture incubator and maintained at 37° C. in 5% $CO_2$ for 48 hours.

B. Double-Stranded DNA Target Sequence Generation for T7E1 Assay gDNA can be isolated from HEK293-Cas9 cells 48 hours after transfection of the dfs2-PN/dfs1-PN using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. gDNA can be then diluted with 150 µL water and samples stored at −80° C.

DNA for T7E1 can be generated by PCR amplification of double-stranded DNA target sequences (e.g., AAVS-1) from isolated gDNA. PCR reactions can be set up using 8 µL gDNA as template with KAPA HiFi Hot Start polymerase and 0.5 U of polymerase, 1× reaction buffer, 0.4 mM dNTPs and 300 nM forward and reverse primers directed to the double-stranded DNA target sequence (e.g., Example 2, Table 12; SEQ ID NO. 15 and SEQ ID NO. 16) in a total volume of 25 µL. The DNA target sequence can be amplified using the following conditions: 95° C. for 5 minutes, 4 cycles of 20 seconds at 98° C., 20 seconds at 70° C., minus 2° C./cycle, 30 seconds at 72° C., followed by 30 cycles of 15 seconds at 98° C., 20 seconds at 62° C., 20 seconds at 72° C., and a final extension at 72° C. for 1 minute.

C. T7E1 Assay

PCR-amplified double-stranded DNA target sequences for T7E1 assays can be denatured at 95° C. for 10 minutes and then allowed to re-anneal by cooling to 25° C. at −0.5° C./s in a thermal cycler. The re-annealed DNA can be incubated with 0.5 µL T7 Endonuclease I in 1× NEBuffer 2 buffer (New England Biolabs, Ipswich, Mass.) in a total volume of 154, for 25 minutes at 37° C. T7E1 reactions can be analyzed using the Fragment Analyzer™ System (Advanced Analytical Technologies, Ames, Iowa) and the DNF-910 Double-stranded DNA Reagent Kit (Advanced Analytical Technologies, Ames, Iowa). The Fragment Analyzer™ System will provide the concentration of each cleavage fragment and of the double-stranded DNA target sequence that remains after cleavage.

Cleavage percentages of the double-stranded DNA target sequences can be calculated from the concentration of each cleavage fragment and the double stranded DNA target sequence that remains after cleavage has taken place, using the following formula:

$$\% \text{ cleavage} = \left(1 - \sqrt{\left(1 - \frac{(frag1 + frag2)}{(frag1 + frag2 + \text{parent})}\right)}\right) \quad \text{EQUATION 1}$$

In Equation 1, frag1 and frag2 concentrations correspond to the concentration of Cas9 cleavage fragments of the double-stranded DNA target sequence and parent corresponds to the double-stranded DNA target sequence that remains after cleavage has taken place.

The T7E1 assay for detection of target sequence modifications in eukaryotic cells will provide data demonstrating that the dfs2-PN/dfs1-PN/Cas9 protein complexes described herein facilitate Cas9-mediated site-specific in vivo cleavage of multiple double-stranded DNA target sequences. sgRNA, crRNA and/or tracrRNA/crRNA polynucleotides having the same DNA target binding sequence as the dfs2-PN/dfs1-PN can also be included in the assay to compare the Cas9-mediated site-specific cleavage percentages between the constructs.

Following the guidance of the present specification and Examples, the T7E1 assay described in this Example can be practiced by one of ordinary skill in the art with other Type II CRISPR Cas9 proteins and their cognate dfs-NATNAs.

Example 8

Probing for Sites Tolerant of Modification in Class 2 Type II Cas9 Guide RNA Backbones This Example describes methods for the generation and testing of engineered dfs-NATNAs.

Breaks can be introduced into the RNA backbone of Class 2 Type II CRISPR guide RNAs (e.g., sgRNAs or dual-guide RNAs) to identify locations for engineering non-native termini in the nucleic acid sequences. The method described below is adapted from Briner, A., et al., Molecular Cell 56(2):333-339 (2014). Not all of the following steps are required for screening nor must the order of the steps be as presented.

A guide RNA from a Class 2 Type II CRISPR system (e.g., a sgRNA, a crRNA, or a tracrRNA) can be selected for engineering. The guide RNA sequence can be modified in silico to introduce breaks in the RNA backbone 3' of the nucleic acid target binding sequence and 5' of the nexus element. Typically, the region(s) are selected from one or more of the following: the lower stem, bulge, or upper stem. Furthermore, after introduction of a break into the RNA backbone, bases can be serially deleted 5' and/or 3' of the break to determine the effects of removal of multiple bases. Breaks in the nucleic acid backbone can also be used to introduce bases that form novel hydrogen base-pair interactions within the guide RNA backbone (e.g., within the bulge sequence).

The introduction of a break into the nucleotide sequences of the first stem element in a Class 2 Type II CRISPR sgRNA as described herein can result in a dfs2-RNA and a dfs1-RNA (see, e.g., FIG. 3A to FIG. 3H). The introduction of a break into the nucleotide sequences of the first stem element in a Class 2 Type II CRISPR dual-guide RNA as described herein can result in dfs2-RNA, a dfs3-RNA, and a dfs1-RNA (see, e.g., FIG. 5A and FIG. 5C).

In silico designed dfs-NATNA RNA sequences can be provided to a commercial manufacturer for synthesis.

Engineered dfs-NATNA RNAs can be evaluated for their ability to support cleavage of a double-stranded DNA target sequence mediated by their cognate Cas9 protein. Amplification of double-stranded DNA target sequences and biochemical cleavage assay can be carried out in a manner similar to those described in Example 2 and Example 3. dfs-NATNA that are capable of mediating cleavage of a DNA target sequence with their cognate Cas9 protein can be validated for activity in cells using the method described in Example 4.

Following the guidance of the present specification and Examples, the modification of a Cas9 guide RNA(s) (e.g., introduction of breaks in the nucleic acid backbone) can be used to design dfs-NATNAs.

Example 9

Screening of dfs-NATNAs Comprising DNA Target Binding Sequences

This Example illustrates the use of dfs-NATNAs of the present invention to modify DNA target sequences present in human genomic DNA and to measure the level of cleavage activity at those sites.

Target sites (DNA target sequences) can be first selected from genomic DNA. dfs-NATNAs can be designed to target the selected sequences. Assays (e.g., as described in Example 3) can be performed to determine the level of DNA target sequence cleavage.

Not all of the following steps are required for every screening nor must the order of the steps be as presented, and the screening can be coupled to other experiments or can form part of a larger experiment.

A. Selecting DNA Target Sequences From Genomic DNA

PAM sequences (e.g., NGG) for a Cas9 protein (e.g., *S. pyogenes* Cas9) can be identified within the selected genomic region.

One or more Cas9 DNA target sequences, 20 nucleotides in length, that are 5' adjacent to a NGG PAM sequence can be identified and selected.

Criteria for selection of nucleic acid target sequences can include, but are not limited to, the following: homology to other regions in the genome; percent G-C content; melting temperature; presences of homopolymer within the spacer; distance between the two sequences; and other criteria known to one skilled in the art.

A DNA target binding sequence that hybridizes to the Cas9 DNA target sequence can be incorporated into a dfs-NATNA (e.g., a dfs1-PN/dfs2-PN). The nucleic acid sequence of a dfs-NATNA construct is typically provided to and synthesized by a commercial manufacturer. Alternatively, the dfs-NATNA construct can be produced as described in Example 1 by in vitro transcription.

A dfs-NATNA, as described herein, can be used with cognate Class 2 Type II CRISPR Cas9 protein to form dfs-NATNA/Cas9 protein complexes.

B. Determination of Cleavage Percentages and Specificity

In vitro cleavage percentages and specificity (i.e., the amount of off-target binding) related to a dfs-NATNA can be determined, for example, using the cleavage assays described in Example 3, and compared as follows:

(1) If only a single pair of DNA target sequences is identified or selected for a dfs-NATNA, the cleavage percentage and specificity for each of the DNA target sequences can be determined. If so desired, cleavage percentage and/or specificity can be altered in further experiments using methods including, but not limited to, modifying the dfs-NATNA, or introducing effector proteins/effector protein-binding sequences to modify the dfs-NATNA or the Cas9 protein, or ligand/ligand-binding moieties to modify the dfs-NATNA or the Cas9 protein.

(2) If multiple pairs of DNA target sequences are identified or selected for a dfs-NATNA, the percentage cleavage data and site-specificity data obtained from the cleavage assays can be compared between different DNAs comprising the target binding sequence to identify the DNA target sequences having the desired cleavage percentage and specificity. Cleavage percentage data and specificity data provide criteria on which to base choices for a variety of applications. For example, in some situations the activity of the dfs-NATNA may be the most important factor. In other situations, the specificity of the cleavage site may be relatively more important than the cleavage percentage. If so desired, cleavage percentage and/or specificity can be altered in further experiments using methods including, but not limited to, modifying the dfs-NATNA, introducing effector proteins/effector protein-binding sequences to modify the dfs-NATNA or the Cas9 protein, or adding ligand/ligand-binding moieties to modify the dfs-NATNA or the Cas9 protein.

Alternatively, or in addition to the in vitro analysis, in cell cleavage percentages and specificities of dfs-NATNAs can be obtained using, for example, the method described in Example 4, and compared as follows:

(1) If only a single pair of DNA target sequences is identified or selected for a dfs-NATNA, the cleavage percentage and specificity for each of the DNA target sequences can be determined. If so desired, cleavage percentage and/or specificity can be altered in further experiments using methods including, but not limited to, modifying the dfs-NATNA, introducing effector proteins/effector protein-binding sequences to modify the dfs-NATNA or the Cas9 protein, or adding ligand/ligand-binding moieties to modify the dfs-NATNA or the Cas9 protein.

(2) If multiple pairs of DNA target sequences are identified or selected for a dfs-NATNA, the percentage cleavage data and site-specificity data obtained from the cleavage assays can be compared between different DNAs comprising the target binding sequences to identify the DNA target sequences having the desired cleavage percentage and specificity. Cleavage percentage data and specificity data provide criteria on which to base choices for a variety of applications. For example, in some situations the activity of the dfs-NATNA may be the most important factor. In other situations, the specificity of the cleavage site may be relatively more important than the cleavage percentage. If so desired, cleavage percentage and/or specificity can be altered in further experiments using methods including, but not limited to, modifying the dfs-NATNA, introducing effector proteins/effector protein-binding sequences to modify the dfs-NATNA or the Cas9 protein, or adding ligand/ligand-binding moieties to modify the dfs-NATNA or the Cas9 protein.

Following the guidance of the present specification and Examples, the screening described in this Example can be practiced by one of ordinary skill in the art with other dfs-NATNAs for use with cognate Class 2 Type II CRISPR Cas9 proteins.

Example 10

Cas9-dCsy4 Fusion Proteins and dfs-NATNAs Comprising a Nucleic Acid Target Binding Sequence and a dCsy4 Binding Domain This example describes the use of a Cas9 fusion with the RNA binding protein dCsy4 (an enzymatically inactive variant of the *Pseudomonas aeruginosa* Csy4 (strain UCBPP-PA14)) and a dfs2-PN comprising a nucleic acid target binding sequence that is modified to include the RNA binding sequence, corresponding to the dCsy4 protein, in the 5'-end sequences of the dfs2-PN comprising a nucleic acid target binding sequence. This combination of a Cas9 fusion to an RNA binding protein and attachment of the corresponding RNA binding protein binding sequence to a dfs2-PN comprising a nucleic acid target binding sequence illustrates another mechanism that can be used to bring the dfs2-PN comprising a nucleic acid target binding sequence into proximity with the nucleic acid binding channel of the Cas protein.

Cas9 protein can be fused at its N-terminal end with the C-terminal end of the dCsy4 protein RNA binding domain or Cas9 protein can be fused at its C-terminal end with the N-terminal end of the dCsy4 RNA binding domain (dCsy4-Cas9 and Cas9-dCsy4, respectively, herein referred to together as (dCsy4)Cas9). The dfs2-PN comprising a nucleic acid target binding sequence can be designed to include a Csy4 hairpin RNA (i.e., the Csy4 binding sequence) in the 5'-end sequences. The Csy4 hairpin can be connected with RNA linkers of various lengths (e.g., 10-40 bases) to dfs2-PNs comprising nucleic acid target binding sequences to produce Csy4-dfs2-PNs comprising nucleic acid target binding sequences.

For a biochemical cleavage reaction, the (dCsy4)Cas9 fusion proteins can be each incubated with a Csy4-dfs2-PN comprising a nucleic acid target binding sequence. The resulting (dCsy4)Cas9/Csy4-dfs2-PN comprising a nucleic acid target binding sequence complexes can be incubated with the other components of the dfs-NATNA (e.g., a dfs2-PN comprising a nucleic acid target binding sequence as shown in FIG. 3A, 322-323, and/or the other dfs1-PN component shown in FIG. 3A, 300) to form a (dCsy4)Cas9/Csy4-dfs2-PN comprising a nucleic acid target binding sequence/dfs1-PN complex.

The (dCsy4)Cas9/Csy4-dfs-PN comprising a nucleic acid target binding sequence/dfs-PN ribonucleoprotein complex constructs as described herein can facilitate Cas9 protein mediated site-specific cleavage of target double-stranded DNA.

Following the guidance of the present specification and examples, the Cas cleavage assay described in this example can be practiced by one of ordinary skill in the art using other CRISPR-Cas9 protein variants (e.g., (dCsy4)Cas variants), including those where the protein domains are introduced in sequences in the middle of the protein.

Example 11

Cross Linking of Cas9 Proteins and dfs-PNs

This example describes the modification of dfs-NATNAs of the present invention to include a cross-linking agent, as well as modification of selected amino acid residues in the Class 2 Type II CRISPR-Cas9 protein. This combination of a modified Cas9 protein and modified dfs-PNs illustrates another mechanism that can be used to bring the nucleic acid target binding sequence of a dfs2-PN (e.g., FIG. 3A, 301; FIG. 5A, 501) into proximity with the nucleic acid binding channel of the Cas9 protein.

A. Cas9 Protein Modifications

Figure 9:
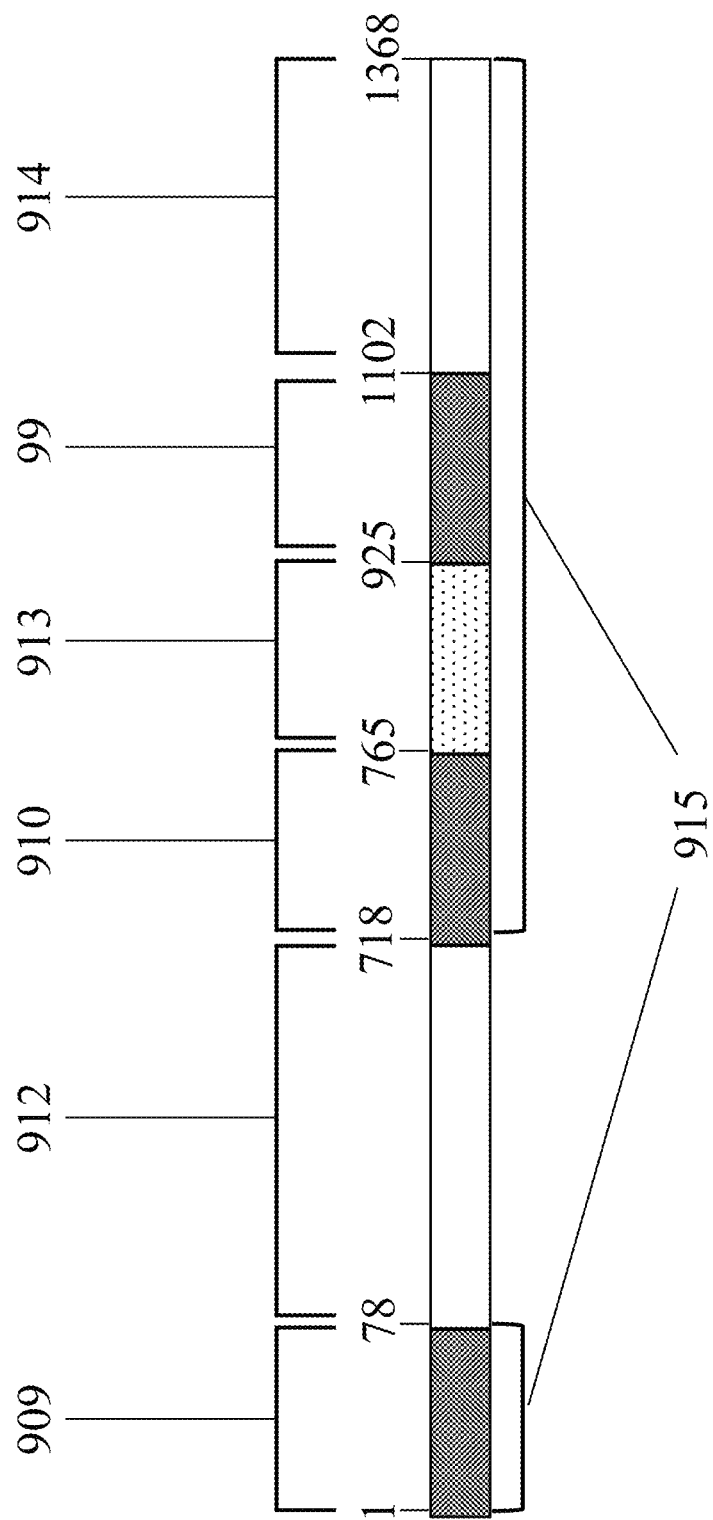
FIG. 9 presents a model of the domain arrangement of *S. pyogenes* Cas9 relative to its primary sequence structure.

FIG. 9 presents a model of the domain arrangement of *S. pyogenes* Cas9 relative to its primary sequence structure. In FIG. 9, three regions of the primary sequence correspond to the RuvC domain (FIG. 9, 909, RuvC-I (amino acids 1-78); FIG. 9, 910, RuvC-II (amino acids 719-765); and FIG. 9, 911, RuvC-III (amino acids 926-1102)). One region corresponds to the helical domain (FIG. 9, 912; helical domain (amino acids 79-718)). One region corresponds to the HNH domain (FIG. 9, 913; HNH (amino acids 766-925)). One region corresponds to the CTD domain (FIG. 9, 914; CTD (amino acids 1103-1368)). In FIG. 9, the regions of the primary sequence corresponding to the alpha-helical lobe (FIG. 9, 912; alpha-helical lobe) and the nuclease domain lobe (FIG. 9, 915; nuclease domain lobe) are indicated with brackets.

The two cysteine (Cys, C) residues present in wild-type SpyCas9 (*Streptococcus pyogenes* serotype M1, UniProtKB-Q99ZW2 (CAS9_STRP1), GenBank: AAK33936.1: SEQ ID NO. 29) can be mutated to serine residues (Ser, S) (C80S, C574S). Single Cys point mutations can be introduced as described in Spanggord, R. J., et al., Nucleic Acids Res 28:1899-1905 (2000).

Briefly, the nucleic acid coding sequence of SpyCas9 can be produced with a substitution of a codon coding for cysteine (TGC) for the original wild-type codon to create the desired introduction of cysteine at discrete positions along the nucleic acid binding channel of the encoded Cas9 protein. The Cas9 nucleic acid (e.g., RNA/DNA) binding channel is described in Jiang, F., et al., Science 351(6275): 867-871 (2016) and Nishimasu, H., et al., Cell 156(5):935-949 (2014).

The amino acid position corresponding to the introduction of Cys codon can be designed to be an optimal distance to the thiol of the thiolated dfs-PN comprising a nucleic acid target binding sequence for S—S cross linking. Distances can be chosen according to the predicted length of the carbon chain linkages in the thiol moiety used in the dfs2-PN comprising a nucleic acid target binding sequence (example lengths for C3 and C6 linkages range between 7 and 10 Å, as discussed in Green, N. S., et al., Protein Science, 10:1293-1304 (2001)). Examples of modified Cas9-Cys protein variants are presented in Table 2. The SpyCas9-Cys protein can be then expressed and purified as described in Jinek, M., et al., Science 337:816-821 (2012)) and concentrated to 1mg/ml.

B. Modification of dfs2-PN Comprising a Nucleic Acid Target Binding Sequence

Figure 10A:
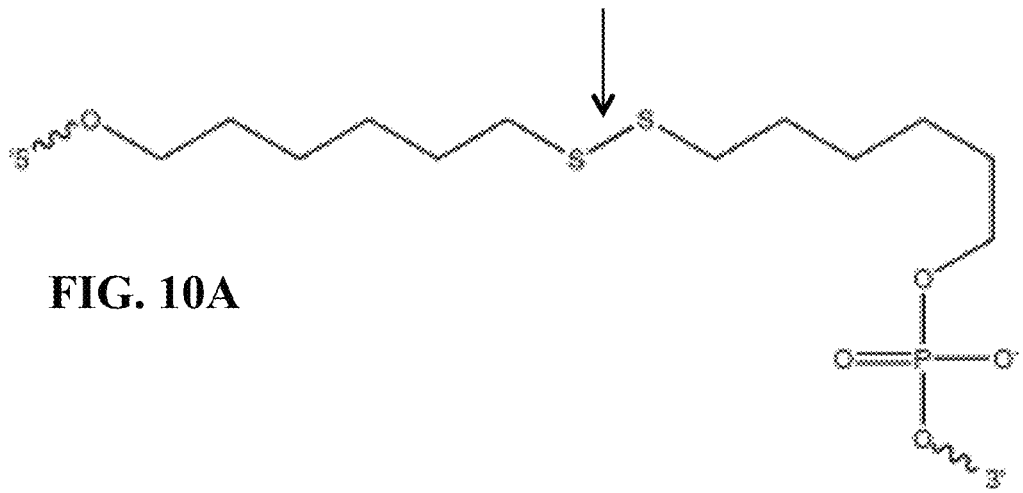
FIG. 10A, FIG. 10B, and FIG. 10C present exemplary thiol functionalities.
Figure 10B:
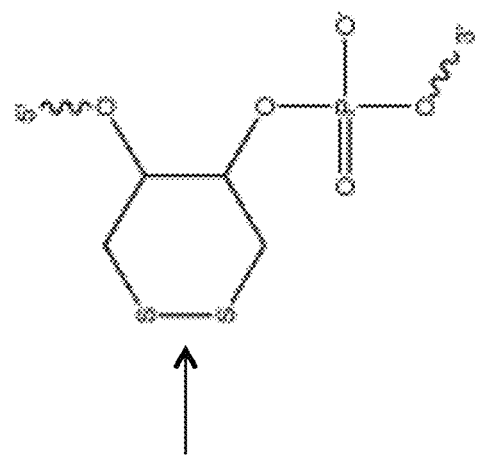
Figure 10C:
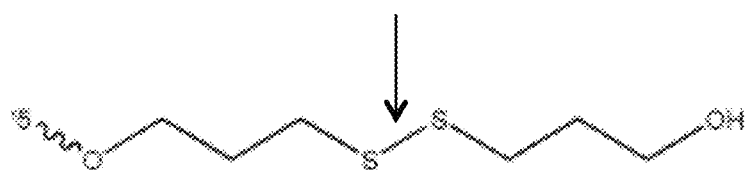

A spacer can be selected to target an AAVS-1 DNA sequence, for example, GGGGCCACUA GGGACAGGAU (SEQ ID NO. 30). Thiol functionalities can be designed along the length of the dfs2-PN comprising a nucleic acid target binding sequence at positions predicted to be at an accessible distance (preferably an optimal distance) to promote S—S formation between the dfs2-PN comprising a nucleic acid target binding sequence and the Cys residue of the modified Cas9-Cys protein variants. A variety of thiol functionalities can be incorporated into thiolated dfs2-PNs including, but not limited to, those shown in FIG. 10A (Thiol C6), FIG. 10B (Dithiol Phosphoramidite, DTPA), and FIG. 10C (Thiol C3). In the figures, arrows indicate the sites of reduction of disulfide bonds. Examples of thiol positions for each of the thiolated dfs2-PN comprising a nucleic acid target binding sequence and the Cas9-Cys protein variants are presented in Table 16.

TABLE 16

Design for Cas9-Cys Protein Variant/Thiolated dfs2-
PNs comprising Nucleic Acid Target Binding Sequences

| Dfs2-PNs | Thiol position | Cas9-Cys variants | | | | | |
|---|---|---|---|---|---|---|---|
| RNA-A | none-WT | | | | | | |
| RNA-B | 1[ThiolC6] | V922C | T924C | E1007C | F1008C | V1009C | Y1010C |
| RNA-C | 5[DTPA] | K510C | R586C | N588C | | | |
| RNA-D | 6[DTPA] | K510C | R586C | N588C | | | |
| RNA-E | 8[DTPA] | K890C | T893C | Q894C | R895C | | |
| RNA-F | 9[DTPA] | K890C | T893C | Q894C | R895C | | |
| RNA-G | 10[DTPA] | E779C | | | | | |
| RNA-H | 13[DTPA] | R494C | M495C | | | | |
| RNA-I | 14[DTPA] | R494C | M495C | | | | |
| RNA-J | 15[DTPA] | Y450C | I448C | | | | |
| RNA-K | 16[DTPA] | R447C | I448C | | | | |
| RNA-L | 17[DTPA] | R447C | I448C | | | | |
| RNA-M | 19[DTPA] | Y72C | R403C | T404C | F405C | D406C | N407C | F164C |
| RNA-N | 20[ThiolC3] | Y72C | R403C | T404C | F405C | D406C | N407C | F164C |

For biochemical cleavage, Cas9-Cys proteins and thiolated dfs2-PN comprising a nucleic acid target binding sequence can each be reduced with 100× molar excess of Tris (2-carboxyethyl) phosphine (TCEP) reagent at room temperature for 2 hours in reaction buffer (20 mM HEPES, 100 mM KCl, 5 mM MgCl$_2$, and 5% glycerol at pH 7.4) following the manufacturer's protocol (Integrated DNA Technologies; Coralville, Iowa). To cross link, the reduced Cas9-Cys proteins and the reduced thiolated dfs-PNs comprising nucleic acid target binding sequences or a control can be incubated together at room temperature for 2 hours in the reaction buffer.

The other dfs2-PN components of the dfs-NATNAs (e.g., a thiolated dfs2-PN comprising a nucleic acid target binding sequence can be as shown in FIG. 3A 323, and the other dfs1-PN will be the component shown in FIG. 3A, 300) can be added to the Cas9-Cys/thiolated dfs-PN comprising a nucleic acid target binding sequence adduct to form the Cas9-Cys/thiolated dfs2-PN comprising a nucleic acid target binding sequence/dfs1-PN ribonucleoprotein complex. The biochemical cleavage reaction can be performed as described in Example 3, but without the addition of DTT. The cleavage reactions can be evaluated for cleavage activity by agarose gel electrophoresis and cleavage percentages calculated as described in Example 3.

The biochemical cleavage data for the Cas9-Cys/thiolated dfs2-PN comprising a nucleic acid target binding sequence/dfs1-PN ribonucleoprotein complexes can be used to demonstrate that the Cas9-Cys/thiolated dfs2-PN comprising a nucleic acid target binding sequence/dfs1-PN constructs as described herein will facilitate Cas9 protein mediated site-specific cleavage of target double-stranded DNA.

Following the guidance of the present specification and examples, the Cas cleavage assay described in this example can be practiced by one of ordinary skill in the art with other CRISPR-Cas9 protein variants (e.g., Cas-Cys variants).

As is apparent to one of skill in the art, various modification and variations of the above embodiments can be made without departing from the spirit and scope of this invention. Such modifications and variations are within the scope of this invention.

The invention claimed is:

1. A method of binding a nucleic acid target sequence, comprising:
   contacting the nucleic acid target sequence with a Class 2 Type II CRISPR-Cas9-nucleoprotein composition comprising,
      a CRISPR Type II Cas9 protein, and
      a Class 2 Type II CRISPR-Cas9-associated discontinuous first-stem nucleic-acid targeting nucleic acid (dfs-NATNA) composition, comprising,
         a first Class 2 Type II CRISPR-Cas9-associated discontinuous first-stem single-strand polynucleotide (dfs1-PN) comprising, in a 5' to 3' direction,
            a fragment nucleotide sequence 1 comprising a 5' terminus of the dfs1-PN and at least 2 nucleotides,
            a bulge element nucleotide sequence II,
            an upper stem element nucleotide sequence II,
            a first linker nucleotide sequence,
            an upper stem element nucleotide sequence I,
            a bulge element nucleotide sequence I,
            a lower stem element nucleotide sequence I,
            a second linker nucleotide sequence,
            a nexus nucleotide sequence,
            a third linker nucleotide sequence, and
            a 3' hairpin element; and
         a second Class 2 Type II CRISPR-Cas9-associated discontinuous first-stem single-strand polynucleotide (dfs2-PN) comprising, in a 5' to 3' direction,
            a nucleic acid target binding sequence, and
            a fragment nucleotide sequence 2 comprising at least 2 nucleotides and a 3' terminus of the dfs2-PN,
      wherein the upper stem element nucleotide sequence I and the upper stem element nucleotide sequence II base-pair hydrogen bond to form an upper stem element;

wherein the bulge element nucleotide sequence I and the bulge element nucleotide sequence II form a bulge element; and wherein at least 2 nucleotides of the fragment nucleotide sequence 1 form 2 pairs of hydrogen-bonded nucleotides with the lower stem element nucleotide sequence I and at least 2 nucleotides of the fragment nucleotide sequence 2 form 2 pairs of hydrogen-bonded nucleotides with the lower stem element nucleotide sequence I to form a lower stem element;

or a first Class 2 Type II CRISPR-Cas9-associated discontinuous first-stem single-strand polynucleotide (dfs1-PN) comprising, in a 5' to 3' direction,
a fragment nucleotide sequence 1 comprising a 5' terminus of the dfs1-PN and at least 2 nucleotides,
a first linker nucleotide sequence,
a nexus nucleotide sequence,
a second linker nucleotide sequence, and
a 3' hairpin element; and a second Class 2 Type II CRISPR-Cas9-associated discontinuous first-stem single-strand polynucleotide (dfs2-PN) comprising, in a 5' to 3' direction,
a nucleic acid target binding sequence,
a lower stem element nucleotide sequence II,
a bulge element nucleotide sequence II,
an upper stem element nucleotide sequence II,
a third linker nucleotide sequence,
an upper stem element nucleotide sequence I,
a bulge element nucleotide sequence I, and
a fragment nucleotide sequence 2 comprising at least 2 nucleotides and a 3' terminus of the dfs2-PN, wherein the upper stem element nucleotide sequence I and the upper stem element nucleotide sequence II base-pair hydrogen bond to form an upper stem element;

wherein the bulge element nucleotide sequence I and the bulge element nucleotide sequence II form a bulge element; and wherein at least 2 nucleotides of the fragment nucleotide sequence 1 form 2 pairs of hydrogen-bonded nucleotides with the lower stem element nucleotide sequence II and at least 2 nucleotides of the fragment nucleotide sequence 2 form 2 pairs of hydrogen-bonded nucleotides with the lower stem element nucleotide sequence II to form a lower stem element;

thereby facilitating binding of the Class2 Type II CRISPR-Cas9 nucleoprotein composition to the nucleic acid target sequence.

2. The method of claim 1, wherein the lower stem element nucleotide sequence I is up to 10 nucleotides.

3. The method of claim 1, wherein the lower stem element nucleotide sequence II is up to 10 nucleotides.

4. The method of claim 1, wherein the lower stem element nucleotide sequence I is 9 nucleotides, the bulge element nucleotide sequence I is 3 nucleotides, the bulge element nucleotide sequence II is 1 nucleotide, and the upper stem element nucleotide sequence I and the upper stem element nucleotide sequence II are each between 3-20 nucleotides.

5. The method of claim 1, wherein the lower stem element nucleotide sequence I is 6 nucleotides, the bulge element nucleotide sequence I is 4 nucleotides, the bulge element nucleotide sequence II is 2 nucleotides, and the upper stem element nucleotide sequence I and the upper stem element nucleotide sequence II are each between 4-20 nucleotides.

6. The method of claim 1, wherein the upper stem nucleotide sequence I and the upper stem element nucleotide sequence II are each between 2 and 22 nucleotides.

7. The method of claim 1, wherein the dfs1-PN further comprises an additional hairpin element 3' of the 3' hairpin element.

8. The method of claim 1, wherein dfs1-PN comprises DNA, RNA, or DNA and RNA, and dfs2-PN comprises DNA, RNA, or DNA and RNA.

9. The method of claim 1, wherein dfs1-PN, dfs2-PN, or dfs1-PN and dfs2-PN comprise a thiol moiety.

10. The method of claim 1, wherein
a pair of hydrogen-bonded nucleotides at the 5' terminus of the dfs1-PN is a pair of Watson-Crick-hydrogen-bonded nucleotides or wobble-hydrogen-bonded nucleotides, and
a pair of hydrogen-bonded nucleotides at the 3' terminus of the dfs2-PN is a pair of Watson-Crick-hydrogen-bonded nucleotides or wobble-hydrogen-bonded nucleotides.

11. The method of claim 10, wherein the pair of hydrogen-bonded nucleotides at the 3' terminus of the dfs2-PN is a pair of Watson-Crick-hydrogen-bonded nucleotides.

12. The method of claim 1, wherein the nucleic acid target sequence is a double-stranded DNA target sequence.

13. The method of claim 12, wherein the binding of the Class 2 Type II CRISPR-Cas9 nucleoprotein composition to the double-stranded DNA target sequence facilitates cleavage of the double-stranded DNA target sequence.

14. The method of claim 13, wherein the method of binding a double-stranded DNA target sequence is carried out in a eukaryotic cell.

15. The method of claim 14, wherein the method of binding a double-stranded DNA target sequence in a eukaryotic cell further comprises providing a donor polynucleotide to the eukaryotic cell, thereby facilitating incorporation of at least a portion of the donor polynucleotide into genomic DNA of the eukaryotic cell.

16. The method of claim 14, wherein the eukaryotic cell is one or more cell selected from the group consisting of a cell of a single-cell eukaryotic organism, a protozoa cell, a cell from a plant, an algal cell, a fungal cell a cell from an invertebrate animal, a cell from a vertebrate animal, and a cell from a mammal.

17. The method of claim 1, wherein the lower stem element nucleotide sequence II is 9 nucleotides, the bulge element nucleotide sequence I is 3 nucleotides, the bulge element nucleotide sequence II is 1 nucleotide, and the upper stem element nucleotide sequence I and the upper stem element nucleotide sequence II are each between 3 and 20 nucleotides.

18. The method of claim 1, wherein the lower stem element nucleotide sequence II is 6 nucleotides, the bulge element nucleotide sequence I is 4 nucleotides, the bulge element nucleotide sequence II is 2 nucleotides, and the upper stem element nucleotide sequence I and the upper stem element nucleotide sequence II are each between 4 and 20 nucleotides.

19. The method of claim 10, wherein the pair of hydrogen-bonded nucleotides at the 5' terminus of the dfs1-PN is a pair of Watson-Crick-hydrogen-bonded nucleotides.

20. The method of claim 1, wherein the CRISPR Type II Cas9 protein is catalytically inactive.

* * * * *

UNITED STATES PATENT AND TRADEMARK OFFICE
CERTIFICATE OF CORRECTION

Page 1 of 1

PATENT NO. : 10,590,415 B2
APPLICATION NO. : 15/787630
DATED : March 17, 2020
INVENTOR(S) : Paul Daniel Donohoue and Andrew Paul May It is certified that error appears in the above-identified patent and that said Letters Patent is hereby corrected as shown below:

On the Title Page
Item [73], delete "Ceribou Biosciences, Inc." and insert --Caribou Biosciences, Inc.--

In the Specification
Column 8, Line 11, delete "FIG. 31I" and insert --FIG. 3H--

In the Claims
Claim 1, Column 83, Line 51, delete "Class2" and insert --Class 2--
Claim 4, Column 83, Line 63, delete "3-20" and insert --3 and 20--
Claim 5, Column 84, Line 2, delete "4-20" and insert --4 and 20--
Claim 16, Column 84, Line 44, delete "a fungal cell a cell from" and insert --a fungal cell, a cell from--

Signed and Sealed this
Fifth Day of May, 2020

Andrei Iancu
*Director of the United States Patent and Trademark Office*

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
agtaataata cgactcacta tag                                           23

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aagcaccgac tcggtgccac                                               20
```

```
<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
taatacgact cactatagct cagagctatg ctgtcctga                    39

<210> SEQ ID NO 4
<211> LENGTH: 97
<212> TYPE: DNA
<213> ORGANISM: Artificial Sequence
<220> FEATURE:
<223> OTHER INFORMATION: Primer

<400> SEQUENCE: 4
gctcagagct atgctgtcct gaaagcagga cagcatagca agttgagcta aggctagtcc    60
gttatcaact tgaaaaagtg gcaccgagtc ggtgctt                            97

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
taatacgact cactatagtc agagctatgc tgtcctgaa                    39

<210> SEQ ID NO 6
<211> LENGTH: 96
<212> TYPE: DNA
<213> ORGANISM: Artificial Sequence
<220> FEATURE:
<223> OTHER INFORMATION: Primer

<400> SEQUENCE: 6
gtcagagcta tgctgtcctg aaagcaggac agcatagcaa gttgacataa ggctagtccg    60
ttatcaactt gaaaaagtgg caccgagtcg gtgctt                             96

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
taatacgact cactatagca gagctatgct gtcctgaaa                    39

<210> SEQ ID NO 8
<211> LENGTH: 95
<212> TYPE: DNA
<213> ORGANISM: Artificial Sequence
<220> FEATURE:
<223> OTHER INFORMATION: Primer

<400> SEQUENCE: 8
gcagagctat gctgtcctga aagcaggaca gcatagcaag ttgcgataag gctagtccgt    60
tatcaacttg aaaaagtggc accgagtcgg tgctt                              95

<210> SEQ ID NO 9
```

```
<211> LENGTH: 39
<212> TYPE: DNA
<213> ORGANISM: Artificial Sequence
<220> FEATURE:
<223> OTHER INFORMATION: Primer

<400> SEQUENCE: 9
taatacgact cactatagag agctatgctg tcctgaaag                              39

<210> SEQ ID NO 10
<211> LENGTH: 94
<212> TYPE: DNA
<213> ORGANISM: Artificial Sequence
<220> FEATURE:
<223> OTHER INFORMATION: Primer

<400> SEQUENCE: 10
gagagctatg ctgtcctgaa agcaggacag catagcaagt tcagataagg ctagtccgtt       60
atcaacttga aaaagtggca ccgagtcggt gctt                                  94

<210> SEQ ID NO 11
<211> LENGTH: 21
<212> TYPE: RNA
<213> ORGANISM: Artificial Sequence
<220> FEATURE:
<223> OTHER INFORMATION: : dfs-casRNA

<400> SEQUENCE: 11
ggggccacua gggacaggau g                                                21

<210> SEQ ID NO 12
<211> LENGTH: 22
<212> TYPE: RNA
<213> ORGANISM: Artificial Sequence
<220> FEATURE:
<223> OTHER INFORMATION: dfs-casRNA

<400> SEQUENCE: 12
ggggccacua gggacaggau gu                                               22

<210> SEQ ID NO 13
<211> LENGTH: 23
<212> TYPE: RNA
<213> ORGANISM: Artificial Sequence
<220> FEATURE:
<223> OTHER INFORMATION: dfs-casRNA

<400> SEQUENCE: 13
ggggccacua gggacaggau guc                                              23

<210> SEQ ID NO 14
<211> LENGTH: 24
<212> TYPE: RNA
<213> ORGANISM: Artificial Sequence
<220> FEATURE:
<223> OTHER INFORMATION: dfs-casRNA

<400> SEQUENCE: 14
ggggccacua gggacaggau gucu                                             24

<210> SEQ ID NO 15
<211> LENGTH: 20
<212> TYPE: DNA
<213> ORGANISM: Artificial Sequence
<220> FEATURE:
<223> OTHER INFORMATION: Primer
```

```
<400> SEQUENCE: 15
ccccgttctc ctgtggattc                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
atcctctctg gctccatcgt                                              20

<210> SEQ ID NO 17
<211> LENGTH: 97
<212> TYPE: RNA
<213> ORGANISM: Artificial Sequence
<220> FEATURE:
<223> OTHER INFORMATION: dfs-casRNA

<400> SEQUENCE: 17
gcucagagcu augcuguccu gaaagcagga cagcauagca aguugagcua aggcuagucc   60
guuaucaacu ugaaaaagug gcaccgaguc ggugcuu                           97

<210> SEQ ID NO 18
<211> LENGTH: 96
<212> TYPE: RNA
<213> ORGANISM: Artificial Sequence
<220> FEATURE:
<223> OTHER INFORMATION: dfs-casRNA

<400> SEQUENCE: 18
gucagagcua ugcuguccug aaagcaggac agcauagcaa guugacauaa ggcuaguccg   60
uuaucaacuu gaaaaagugg caccgagucg gugcuu                            96

<210> SEQ ID NO 19
<211> LENGTH: 95
<212> TYPE: RNA
<213> ORGANISM: Artificial Sequence
<220> FEATURE:
<223> OTHER INFORMATION: dfs-casRNA

<400> SEQUENCE: 19
gcagagcuau gcuguccuga aagcaggaca gcauagcaag uugcgauaag gcuaguccgu   60
uaucaacuug aaaaaguggc accgagucgg ugcuu                             95

<210> SEQ ID NO 20
<211> LENGTH: 94
<212> TYPE: RNA
<213> ORGANISM: Artificial Sequence
<220> FEATURE:
<223> OTHER INFORMATION: dfs-casRNA

<400> SEQUENCE: 20
gagagcuaug cuguccugaa agcaggacag cauagcaagu ucagauaagg cuaguccguu   60
aucaacuuga aaaaguggca ccgagucggu gcuu                              94

<210> SEQ ID NO 21
<211> LENGTH: 20
<212> TYPE: DNA
<213> ORGANISM: Artificial Sequence
<220> FEATURE:
```

<223> OTHER INFORMATION: oligonucleotide

<400> SEQUENCE: 21
ggggccacta gggacaggat    20

<210> SEQ ID NO 22
<211> LENGTH: 52
<212> TYPE: DNA
<213> ORGANISM: Artificial Sequence
<220> FEATURE:
<223> OTHER INFORMATION: Primer

<400> SEQUENCE: 22
cactctttcc ctacacgacg ctcttccgat cttctggcaa ggagagagat gg    52

<210> SEQ ID NO 23
<211> LENGTH: 48
<212> TYPE: DNA
<213> ORGANISM: Artificial Sequence
<220> FEATURE:
<223> OTHER INFORMATION: Primer

<400> SEQUENCE: 23
ggagttcaga cgtgtgctct tccgatctta tattcccagg gccggtta    48

<210> SEQ ID NO 24
<211> LENGTH: 57
<212> TYPE: DNA
<213> ORGANISM: Artificial Sequence
<220> FEATURE:
<223> OTHER INFORMATION: Primer

<400> SEQUENCE: 24
caagcagaag acggcatacg agattacgtg atgtgactgg agttcagacg tgtgctc    57

<210> SEQ ID NO 25
<211> LENGTH: 58
<212> TYPE: DNA
<213> ORGANISM: Artificial Sequence
<220> FEATURE:
<223> OTHER INFORMATION: Primer

<400> SEQUENCE: 25
aatgatacgg cgaccaccga gatctacacc gtctaataca ctctttccct acacgacg    58

<210> SEQ ID NO 26
<211> LENGTH: 58
<212> TYPE: DNA
<213> ORGANISM: Artificial Sequence
<220> FEATURE:
<223> OTHER INFORMATION: Primer

<400> SEQUENCE: 26
aatgatacgg cgaccaccga gatctacact ctctccgaca ctctttccct acacgacg    58

<210> SEQ ID NO 27
<211> LENGTH: 58
<212> TYPE: DNA
<213> ORGANISM: Artificial Sequence
<220> FEATURE:
<223> OTHER INFORMATION: Primer

<400> SEQUENCE: 27
aatgatacgg cgaccaccga gatctacact cgactagaca ctctttccct acacgacg    58

-continued

<210> SEQ ID NO 28
<211> LENGTH: 58
<212> TYPE: DNA
<213> ORGANISM: Artificial Sequence
<220> FEATURE:
<223> OTHER INFORMATION: Primer

<400> SEQUENCE: 28
aatgatacgg cgaccaccga gatctacact tctagctaca ctctttccct acacgacg       58

<210> SEQ ID NO 29
<211> LENGTH: 1368
<212> TYPE: PRT
<213> ORGANISM: Streptococcus pyogenes

<400> SEQUENCE: 29

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
    675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly

```
                740                 745                 750
Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775             780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935             940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155
```

```
Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

<210> SEQ ID NO 30
<211> LENGTH: 20
<212> TYPE: RNA
<213> ORGANISM: Artificial Sequence
<220> FEATURE:
<223> OTHER INFORMATION: oligonucleotide

<400> SEQUENCE: 30
ggggccacua gggacaggau                                              20
```